United States Patent [19]

O'Neal et al.

[11] 4,367,339

[45] Jan. 4, 1983

[54] SUBSTITUTED N-NITROANILINE COMPOUNDS AND INORGANIC AND ORGANIC SALTS THEREOF USEFUL FOR ENHANCING AUXILIARY BRANCHING, CANOPY FLOWERING AND CROP YIELD OF PLANT AND AS LODGING INHIBITORS THEREFOR

[75] Inventors: Thomas D. O'Neal, Princeton; Prithvi R. Bhalla, Hightstown; Barrington Cross, Rocky Hill, all of N.J.

[73] Assignee: American Cyanamid Company, Stamford, Conn.

[21] Appl. No.: 179,335

[22] Filed: Aug. 18, 1980

[51] Int. Cl.$^3$ .......................................... C07D 231/10
[52] U.S. Cl. ........................................ 548/378; 71/76; 71/88; 71/90; 71/92; 71/94; 71/95; 71/98; 71/103; 71/105; 71/111; 71/115; 71/118; 71/121; 71/123; 544/159; 544/165; 544/392; 544/395; 546/172; 546/176; 546/211; 546/334; 548/252; 548/254; 548/341; 548/342; 548/375; 548/377; 549/29; 260/465 E
[58] Field of Search ............... 564/107; 548/378, 375, 548/377; 71/121, 92, 76

[56] References Cited

U.S. PATENT DOCUMENTS

| | | | |
|---|---|---|---|
| 3,567,421 | 3/1971 | Pape et al. | 71/76 |
| 3,844,762 | 10/1974 | Cross et al. | 71/121 |
| 3,857,692 | 12/1974 | Feeny | 548/373 |
| 3,867,403 | 2/1975 | Feeny | 71/92 |
| 3,891,706 | 6/1975 | Wilcox | 71/121 |
| 4,130,645 | 12/1978 | Cross et al. | 564/107 |
| 4,162,913 | 7/1979 | Feeny | 71/92 |

OTHER PUBLICATIONS

Kovacs, "Weed Control in Winter Wheat, etc.," (1974) CA 85, No. 1127 p. (1976).

*Primary Examiner*—Glennon H. Hollrah
*Attorney, Agent, or Firm*—Thomas J. Monahan

[57] ABSTRACT

There are provided di- tri- and tetrasubstituted N-nitroaniline compounds and inorganic and organic salts thereof which are effective for increasing axillary branching, improving canopy and enhancing flowering of herbaceous ornamental plants and graminaceous crops, leguminous crops, cotton and sunflowers. The salts are also effective as yield enhancing agents and lodging inhibitors for the crops.

12 Claims, No Drawings

SUBSTITUTED N-NITROANILINE COMPOUNDS AND INORGANIC AND ORGANIC SALTS THEREOF USEFUL FOR ENHANCING AUXILIARY BRANCHING, CANOPY FLOWERING AND CROP YIELD OF PLANT AND AS LODGING INHIBITORS THEREFOR

The invention is the use of plant regulating substituted N-nitroanilines represented by formulae (I) and (Ia) below:

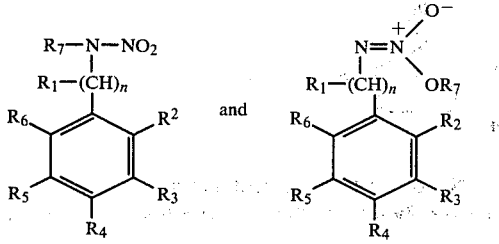

wherein n is an integer of 0 or 1; $R_1$ is hydrogen, $C_1$–$C_3$ alkyl, $C_1$–$C_3$ haloalkyl, CN, halogen, $NO_2$, $SO_2R_8$, $COR_9$, phenyl or substituted phenyl and the substituents are $CH_3$, $CF_3$, $CH_3O$, halogen, $NO_2$ or $OCH_2$—$CO_2C_2H_5$; $R_2$ and $R_6$ are hydrogen, halogen, $C_1$–$C_4$ alkyl, $C_1$–$C_4$ haloalkyl, $C_1$–$C_4$ haloalkoxy, $SO_2R_8$, $SR_8$ or $COR_{10}$; $R_3$ is hydrogen, $C_1$–$C_4$ alkyl, $C_1$–$C_4$ alkoxy, $NH_2$, NH—$COCH_3$, halogen, $NO_2$, $SO_2R_8$, CN or $CO_2CH_3$; $R_4$ is hydrogen, halogen, $C_1$–$C_2$ alkyl, $SO_2R_8$, $SR_8$, $OCF_3$, $COR_9$, CN, NH—$COCH_3$, $SO_2NR_{10}R_{11}$,

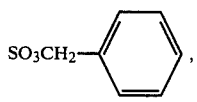

phenoxy or substituted phenoxy and the substituents are $CH_3$, $CF_3$, $CH_3O$, halogen, $NO_2$ or $OCH_2CO_2C_2H_5$; $R_5$ is hydrogen, $C_1$–$C_3$ alkyl or halogen; $R_7$ is hydrogen, $C_1$–$C_{12}$ alkyl optionally substituted with halogen or CN, $C_3$–$C_4$ alkenyl, $C_3$–$C_4$ alkynyl, the methyl esters of lower alkanoic acids or the moiety

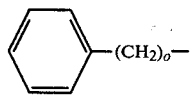

wherein o is an integer of 0, 1, 2 or 3, and the moiety may optionally be substituted with halogen, $C_1$–$C_2$ alkyl, $C_1$–$C_2$ alkoxy, $(C_1$–$C_3$ alkyl$)_3$ $SiCH_2$— or $NO_2$; $R_8$ is $C_1$–$C_6$ alkyl, phenyl or benzyl; $R_9$ is hydrogen, hydroxyl, $C_1$–$C_3$ alkyl, $C_1$–$C_3$ alkoxy or phenyl; $R_{10}$ and $R_{11}$ each are hydrogen, $C_1$–$C_4$ alkyl or phenyl; with the proviso that not less than two and not more than four of $R_2$ to $R_6$ are to be substituted with groups other than hydrogen in any one of the compounds represented by formulae (I) and (Ia) and mixtures thereof; and when $R_7$ is hydrogen, the above compounds of formulae (I) and (Ia) may form inorganic or organic salts, the salt being represented by formula (II) below:

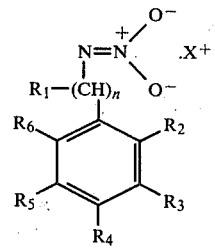

When X is inorganic, it is alkali metals, alkaline earth metals, Co, Ni, Cu, Zn, or Ag.

When the cation $X^+$ is organic, $X^+$ is represented by formula IIIa $$N^+R_aR_bR_cR_d \quad (IIIa)$$

wherein $R_a$ is hydrogen, $C_1$–$C_{30}$ alkyl straight chain or branched [optionally mono- or disubstituted with HO—, $CH_3O_2C$—, $CH_3S$—, $C_3$–$C_{18}$ alkenylaminoalkylene ($C_1$–$C_3$), $H_2N$—, $(CH_3)_2N$—,

$C_3$–$C_6$ alkenyl, $C_3$–$C_6$ alkynyl, $C_3$–$C_6$ cycloalkyl,

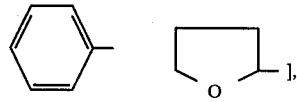

wherein $R_e$ and $R_f$ each may be H, $CH_3$ or n-$C_{16}H_{33}SO_2$—; $R_b$ is hydrogen, $C_1$–$C_{30}$ alkyl straight chain or branched [optionally mono- or disubstituted with HO— or

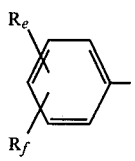

$R_c$ is hydrogen, $C_1$–$C_{30}$ alkyl straight chain or branched [optionally mono- or disubstituted with HO— or

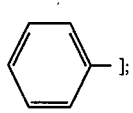

$R_d$ is hydrogen, $C_1$–$C_{30}$ alkyl straight chain or branched [optionally substituted with HO—, Cl— or

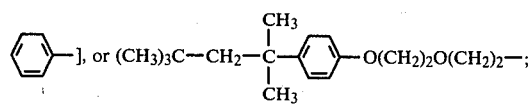

and when $R_a$ and $R_b$ are taken together with the nitrogen they are attached to they represent a moiety of

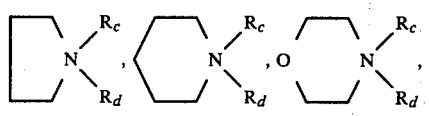

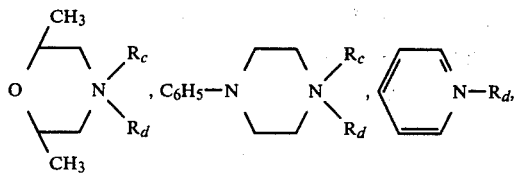

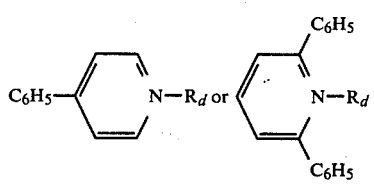

wherein $R_c$ and $R_d$ are defined as above.

The organic cation $X^+$ may also be imidazolium, pyridinium, quinolinium, dithiolium, tetrazolium or be represented by formula IIIb

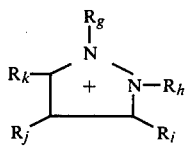

(IIIb)

wherein $R_g$ and $R_h$ each are $C_1$–$C_3$ alkyl; $R_j$ is hydrogen, halogen, $C_1$–$C_3$ alkyl or $C_1$–$C_3$ alkoxy; $R_i$ and $R_k$ each are hydrogen $C_1$–$C_6$ alkyl straight chain or branched; $C_3$–$C_6$ cycloalkyl,

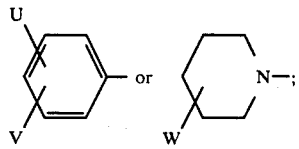

wherein U and V each are hydrogen, halogen, $C_1$–$C_3$ alkyl, $C_1$–$C_3$ alkoxy, CN or $CF_3$; W is hydrogen or $C_1$–$C_3$ alkyl; and each ≡≡≡ symbol represents a single or double bond, wherein if both are single bonds then the cations are pyrazolidium cations represented by formula (IIIc)

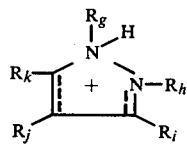

(IIIc)

wherein $R_g$ to $R_k$ are as defined above; and when one of the ≡≡≡ symbols represents a double bond then the cations are pyrazolinium cations represented by formula (IIId)

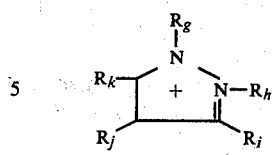

(IIId)

wherein $R_g$ to $R_k$ are as defined above; and when both ≡≡≡ symbols represent double bonds, then the cations are pyrazolium cations represented by formula (IIIe)

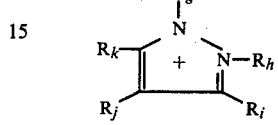

(IIIe)

wherein $R_g$ to $R_k$ are as defined above.

X may also be represented by Formulae IIIf and IIIg $$R_1\text{-}P^+(R_m)_3 \quad \text{(IIIf)}$$

wherein $R_1$ is $C_1$–$C_6$ alkyl,

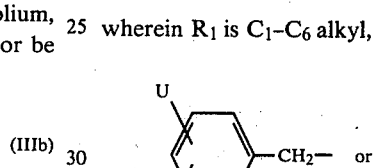

wherein U and V are as hereinabove defined; $R_m$ is $C_1$–$C_6$ alkyl or

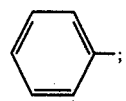

$SR_a^+R_bR_c$ (IIIg); and $I^+R_aR_b$ (IIIh).

A group of compounds represented by formula IV when n is 0, of particular interest for use in the invention, are graphically illustrated and described as follows:

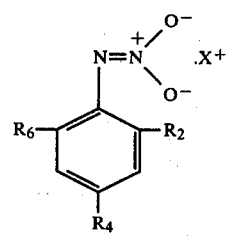

IV wherein $R_2$ is Br, Cl, F, I, $C_1$–$C_4$ alkyl, $OCHF_2$, $CF_3$, $SR_8$, $SO_2R_8$, or $COR_9$; $R_4$ is Br, Cl, F, I, $CH_3$, $OCF_3$, $NHCO$—$CH_3$, CN, $SR_8$, $SO_2R_8$, $COR_9$, phenoxy or substituted phenoxy wherein the substituents are selected from the group described above; $R_6$ is Br, Cl, F, I or $C_1$–$C_4$ alkyl; $R_8$ and $R_9$ are as hereinabove defined; and cation $X^+$ is as hereinabove defined.

A second group of compounds represented by formula (IV) above and of interest are those wherein $R_2$, $R_4$ and $R_6$ are each bromine; $X^+$ is $R_aNH_3^+$, wherein $R_a$ is H, $CH_3$, $C_2H_5$, n-$C_3H_7$, i-$C_3H_7$, n-$C_4H_9$, sec-$C_4H_9$, i-$C_4H_9$, t-$C_4H_9$, n-$C_5H_{11}$, n-$C_6H_{13}$, n-$C_8H_{17}$, n-$C_{12}H_{25}$, $C_{18}H_{35}$, n-$C_{18}H_{37}$, n-$C_{20}H_{41}$, $H_2C=CH-CH_2-$, $HC\equiv C-CH_2-$, $HOCH_2CH_2-$, $(CH_3)_2CHCH_2-\overset{|}{\underset{CO_2CH_3}{CH}}-$, $CH_3S(CH_2)_3$, $C_8H_{17}CH=CH-C_8H_{16}-NH-C_3H_6-$,

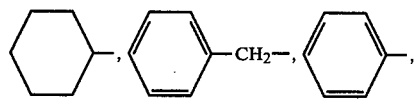

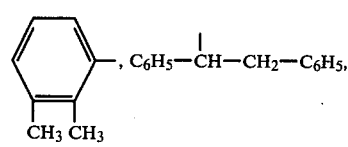

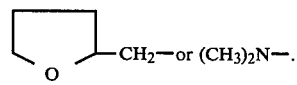

A third group of compounds represented by formula IV, above, of interest are those wherein $R_2$, $R_4$ and $R_6$ each are bromine and $X^+$ is $(CH_2)_2\overset{+}{N}H_2$, $(C_2H_5)_2\overset{+}{N}H_2$, (n-$C_3H_7)_2\overset{+}{N}H_2$, $[(CH_3)_2CH]_2\overset{+}{N}H_2$, (n-$C_4H_9)_2\overset{+}{N}H_2$, $(C_{18}H_{37})_2\overset{+}{N}H_2$, $(HOCH_2CH_2)_2\overset{+}{N}H_2$,

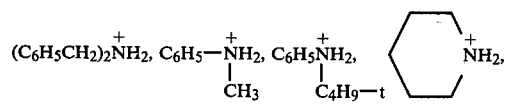

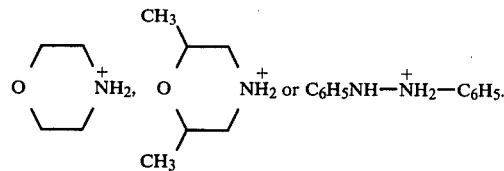

A fourth group of compounds represented by formula IV, above are those wherein $R_2$, $R_4$ and $R_6$ each are bromine and $X^+$ is $(CH_3)_3\overset{+}{N}H$, $(C_2H_5)_3\overset{+}{N}H$, (n-$C_3H_7)_3\overset{+}{N}H$, $(HOCH_2CH_2)_3\overset{+}{N}H$

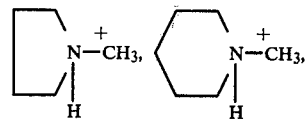

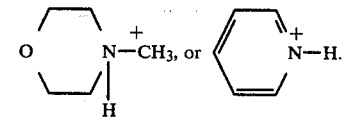

A fifth group of compounds of interest and represented by formula IV above are those wherein $R_2$, $R_4$ and $R_6$ each are bromine and $X^+$ is $(CH_3)_4\overset{+}{N}$, $(C_2H_5)_4\overset{+}{N}$, (n-$C_3H_7)_4\overset{+}{N}$, (n-$C_4H_9)_4\overset{+}{N}$, (n-$C_{10}H_{23})_3\overset{+}{N}CH_3$, n-$C_{16}H_{33}\overset{+}{N}(CH_3)_3$, $Cl-CH_2CH_2\overset{+}{N}(CH_3)_3$, $HOCH_2CH_2\overset{+}{N}(CH_3)_3$,

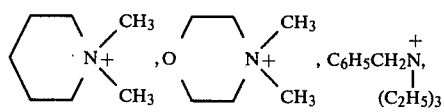

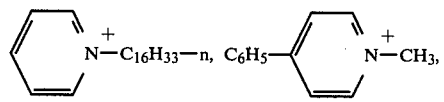

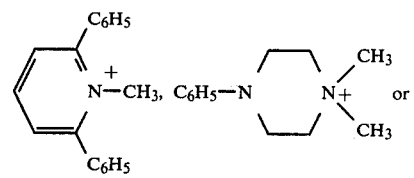

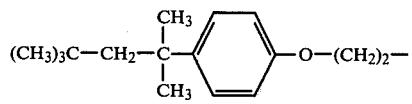

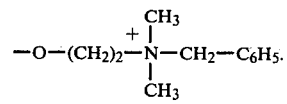

Another, important group of plant regulating compounds represented by formula II above, are those wherein the cation $X^+$ is pyrazolium, pyrazolinium or pyrazolidinium moieties as represented by structural formula IV and discussed and described in detail as follows:

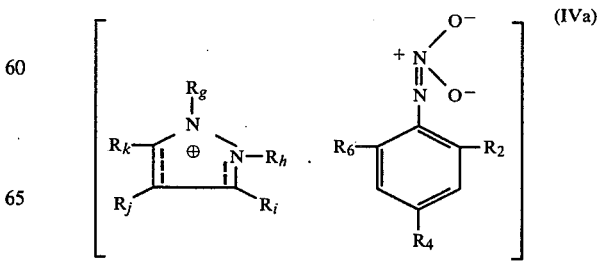

(IVa)

comprising a cation of formula (IIIb)

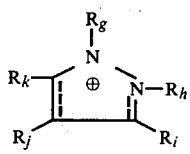
(IIIb)

wherein $R_g$ and $R_h$ each are methyl or ethyl; $R_j$ is hydrogen, bromine, chlorine, fluorine, methyl or methoxy; $R_i$ and $R_k$ each are hydrogen, cyclohexyl,

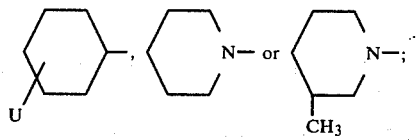

U is hydrogen, $CF_3$, methyl, methoxy, chlorine, bromine or fluorine; and a phenylnitramine anion of formula (IV)

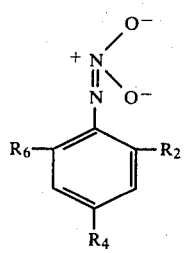
(IV)

wherein $R_2$, $R_4$ and $R_6$ each are bromine, chlorine, iodine, methyl or trifluoromethyl; and ≡≡≡ represents a single or double bond.

A preferred group of salts useful in the invention are represented by formula (IVa) above are those wherein each of the ≡≡≡ represent double bonds; $R_g$ and $R_h$ each are methyl; $R_j$ is hydrogen; $R_i$ and $R_k$ each are cyclohexyl,

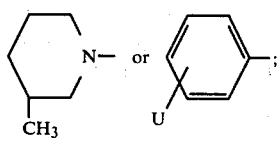

U is hydrogen, methyl, methoxy, chlorine, fluorine or trifluoromethyl.

The most preferred compounds useful in the invention are represented by formula (IVa) are those, wherein $R_2$, $R_4$, $R_6$ each are trifluoromethyl, bromine or iodine; $R_k$ and $R_i$ each are phenyl.

Of special interest are formula IV salts represented by the structures shown below:

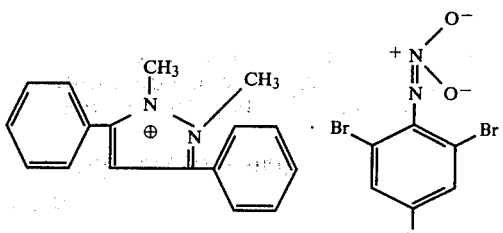

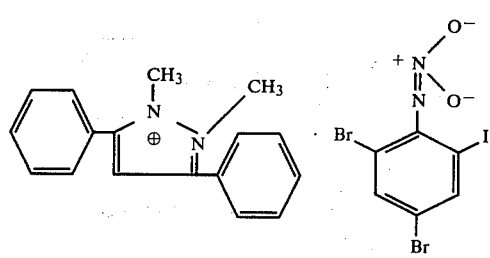

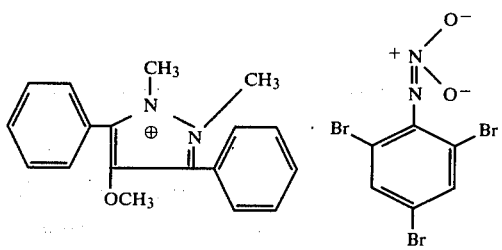

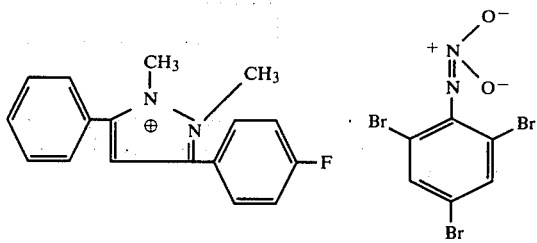

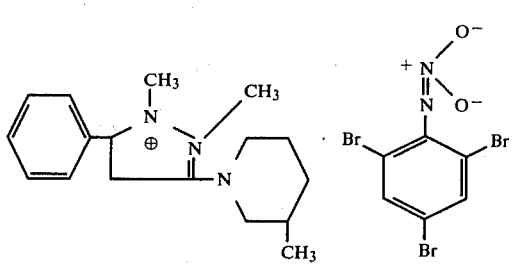

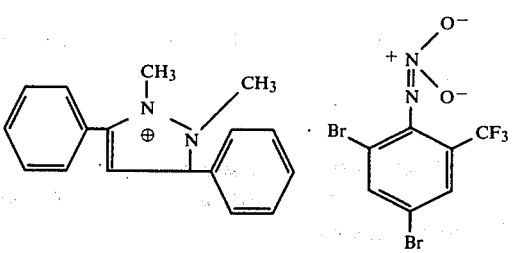

Other compounds of formula II useful in the invention are compounds wherein the anion has the structure (V)

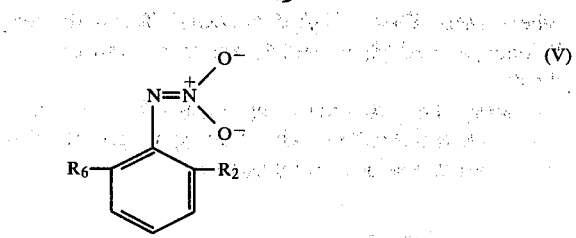 (V)

and $R_2$ and $R_6$ each are halogen, $C_1$-$C_4$ alkyl or $C_1$-$C_3$ haloalkyl; cation $X^+$ is as hereinabove defined. Among the compounds described above, preferred are those wherein $R_2$ and $R_6$ each are bromine, chlorine, iodine or $CF_3$; and cation $X^+$ is $C_{18}H_{35}N^+H_3$ or is the pyrazolium cation of formula

wherein $R_h$ is $C_1$-$C_2$ alkyl; $R_i$ is phenyl; $R_j$ is hydrogen, halogen or methyl.

Also useful in the invention are compounds formula II salts wherein the anion is represented by structure (VI)

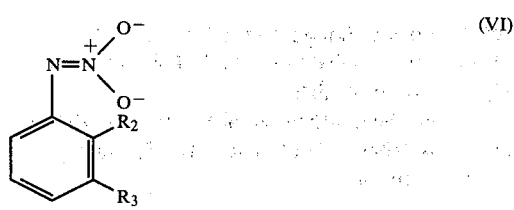 (VI)

$R_2$ and $R_3$ each are halogen or $C_1$-$C_4$ alkyl; cation $X^+$ is as hereinabove defined. Of particular interest are those salts wherein $R_2$ and $R_3$ each are bromine or chlorine; cation $X^+$ is $C_{18}H_{35}N^+H_3$ or the pyrazolium cation of formula

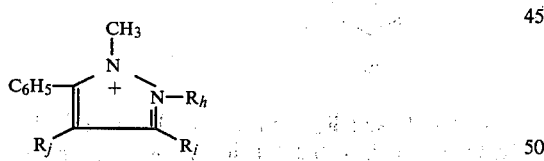

wherein $R_h$ is $C_1$-$C_2$ alkyl; $R_i$ is phenyl; $R_j$ is hydrogen, halogen or methyl.

Among the trisubstituted salts of formula II useful in the invention the following are of interest:

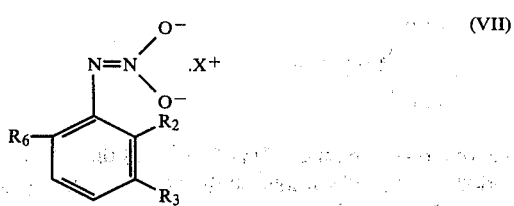 (VII)

wherein $R_2$, $R_3$ and $R_6$ each are halogen, alkyl $C_1$-$C_4$ or haloalkyl $C_1$-$C_4$; cation $X^+$ is as hereinabove defined; and especially those wherein $R_2$, $R_3$ and $R_6$ each are Br, Cl or I and when $R_2$ and $R_3$ are Cl the $R_6$ is Br, or if one is $CF_3$, the other two have to be Br or I; and cation $X^+$ is $C_{18}H_{35}N^+H_3$ or is the moiety

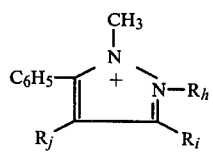

$R_h$ is $C_1$-$C_2$ alkyl; $R_i$ is phenyl; $R_j$ is hydrogen, halogen or methyl.

Further compounds useful in the invention are of the structure:

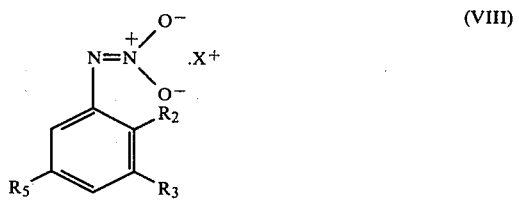 (VIII)

wherein $R_2$, $R_3$ and $R_5$ each are Br, Cl, I, F or $C_1$-$C_4$ alkyl; the cation especially those wherein $X^+$ is as hereinabove defined, and is preferably $R_2$, $R_3$ and $R_5$ all are Br or I, and cation $X^+$ is $C_{18}H_{35}N^+H_3$ or a pyrazolium cation of formula:

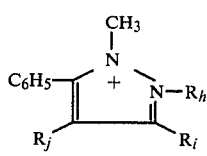

wherein $R_h$ is $C_1$-$C_2$ alkyl; $R_i$ is phenyl; $R_j$ is hydrogen, halogen or methyl.

A further trisubstituted salt useful in the invention is the structure:

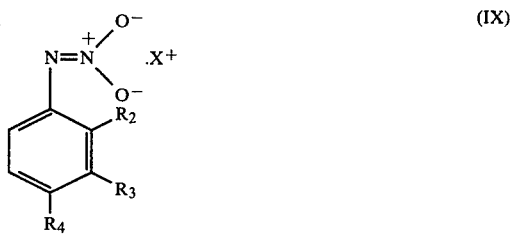 (IX)

wherein $R_2$, $R_3$ and $R_4$ are Br, Cl, I or $C_1$-$C_2$ alkyl; cation $X^+$ is as hereinabove defined, preferentially $C_{18}H_{35}N^+H_3$ or the moiety

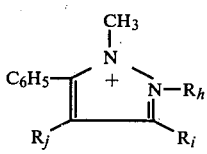

wherein $R_h$ is $C_1$-$C_2$ alkyl; $R_i$ is phenyl; $R_j$ is hydrogen, halogen or methyl.

Among the tetrasubstituted salts of formula II useful in the invention are of the formula:

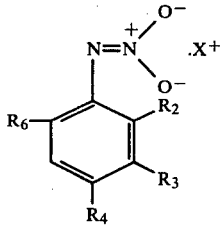

wherein $R_2$ and $R_6$ each are $C_1$-$C_4$ alkyl, Br, Cl, F or $CF_3$; $R_3$ is $CH_3$, $CH_3O$, $CO_2CH_3$, $SO_2CH_3$, $NH_2$, $NHCOCH_3$, CN, $NO_2$, Cl or F; $R_4$ is $C_1$-$C_2$ alkyl, Br, Cl or F; cation $X^+$ is as hereinabove defined. Of particular interest are those compounds wherein substituents $R_2$ to $R_6$ are in the combinations given below:

| $R_2$ | $R_3$ | $R_4$ | $R_6$ |
|---|---|---|---|
| $CH_3$ | Cl | Br | Br |
| Br | Cl | Br | Cl |
| Br | Cl | $CH_3$ | Br |
| Br | F | Br | Br |
| Br | $SO_2CH_3$ | Br | Br |
| Br | $NHCOCH_3$ | Br | Br | and cation $X^+$ is $C_{18}H_{35}N^+H_3$ or a pyrazolium cation of formula

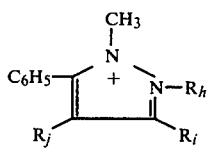

wherein $R_h$ is $C_1$-$C_2$ alkyl; $R_i$ is phenyl; $R_j$ is hydrogen, halogen or methyl.

Among the formula II salts wherein n is 1, the following are useful in the invention:

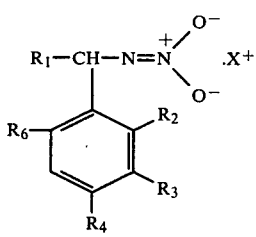

wherein $R_1$ is hydrogen, $C_1$-$C_3$ alkyl, $C_1$-$C_3$ haloalkyl, CN, halogen, $NO_2$, $SO_2R_8$, $COR_9$, phenyl or substituted phenyl and the substituents are $CH_3$, $CF_3$, $CH_3O$, $NO_2$, Br, Cl, F or $OCH_2CO_2C_2H_5$; $R_2$, $R_3$ and $R_6$ each are hydrogen, $C_1$-$C_4$ alkyl, Br, Cl, F or $CF_3$; $R_4$ is hydrogen, $C_1$-$C_2$ alkyl, Br, Cl or F; cation $X^+$ is as hereinabove defined; but is preferably $Na^+$, $C_{18}H_{35}N^+H_3$ or a pyrazolium cation of formula

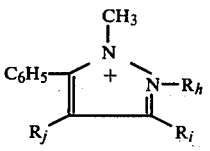

wherein $R_h$ is $C_1$-$C_2$ alkyl; $R_i$ is phenyl; $R_j$ is hydrogen, halogen or methyl; $R_8$ and $R_9$ are as hereinabove defined.

Among the compounds represented by formula I wherein n is 0 and $R_7$ is other than hydrogen, the following are of useful in the invention:

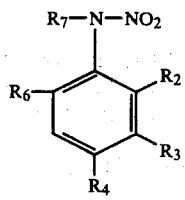

wherein $R_2$ and $R_6$ each are Cl, Br, I, $NO_2$; $R_3$ is hydrogen or $C_1$-$C_2$ alkyl; $R_4$ is hydrogen, halogen or $C_1$-$C_3$ alkyl; $R_7$ is $C_1$-$C_{12}$ alkyl optionally substituted with halogen or CN, $C_3$-$C_4$ alkenyl, $C_3$-$C_4$ alkynyl, ($C_1$-$C_3$ alkyl)$_3$SiCH$_2$—, the methyl esters of lower alkanoic acids or the moiety

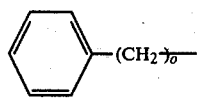

wherein o is an integer of 0,1,2 or 3 and the moiety may optionally be substituted with halogen, $C_1$-$C_2$ alkyl, $C_1$-$C_2$ alkoxy or nitro.

Among the compounds of formula Ia wherein n is 0 and $R_7$ is other than hydrogen the following are useful in the invention:

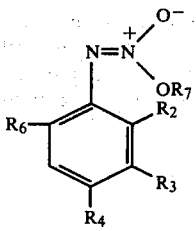

wherein $R_2$ and $R_6$ each are Cl, Br, I or $NO_2$; $R_3$ is hydrogen or $C_1$-$C_2$ alkyl; $R_4$ is hydrogen, halogen or $C_1$-$C_3$ alkyl; $R_7$ is $C_1$-$C_{12}$ alkyl optionally substituted with halogen or CN, $C_3$-$C_4$ alkenyl, $C_3$-$C_4$ alkynyl, ($C_1$-$C_3$ alkyl)$_3$SiCH$_2$—, the methyl esters of lower alkanoic acids or the moiety

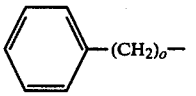

wherein o is an integer of 0,1,2 or 3 and the moiety may optionally be substituted with halogen, $C_1$-$C_2$ alkyl, $C_1$-$C_2$ alkoxy or $NO_2$.

Among the compounds of the invention the following compounds represented by formulae (I) and (Ia) are novel:

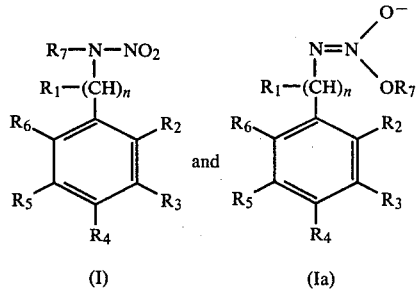

(I)  (Ia)

wherein n is an integer of 0 or 1; $R_1$ is hydrogen, $C_1-C_3$ alkyl, $C_1-C_3$ haloalkyl, CN, halogen, $NO_2$, $SO_2R_8$, $COR_9$, phenyl or substituted phenyl and the substituents are $CH_3$, $CF_3$, $CH_3O$, halogen, $NO_2$ or $OCH_2CO_2C_2H_5$; $R_2$ and $R_6$ are hydrogen, halogen, $C_1-C_4$ alkyl, $C_1-C_4$ haloalkyl, $C_1-C_4$ haloalkoxy, $SO_2R_8$, $SR_8$ or $COR_{10}$; $R_3$ is hydrogen, $C_1-C_4$ alkyl, $C_1-C_4$ alkoxy, $NH_2$, $NHCOCH_3$, halogen, $NO_2$, $SO_2R_8$, CN or $CO_2CH_3$; $R_4$ is hydrogen, halogen, $C_1-C_2$ alkyl, $SO_2R_8$, $COR_9$, CN, $NHCOCH_3$, $SO_2NR_{10}R_{11}$,

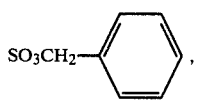

phenoxy or substituted phenoxy and the substituents are $CH_3$, $CF_3$, $OCF_3$, $CH_3O$, halogen, $NO_2$ or $OCH_2CO_2C_2H_5$; $R_5$ is hydrogen, $C_1-C_3$ alkyl or halogen; $R_7$ is hydrogen, $C_1-C_{12}$ alkyl optionally substituted with halogen or CN, $C_3-C_4$ alkenyl, $C_3-C_4$ alkynyl, the methyl esters of lower alkanoic acids or the moiety

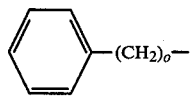

wherein o is an integer of 0,1,2 or 3, and the moiety may optionally be substituted with halogen, $C_1-C_2$ alkyl, $C_1-C_2$ alkoxy, $(C_1-C_3$ alkyl$)_3SiCH_2$— or $NO_2$; $R_8$ is $C_1-C_6$ alkyl, phenyl or benzyl; $R_9$ is hydrogen, hydroxyl, $C_1-C_3$ alkyl, $C_1-C_3$ alkoxy or phenyl; $R_{10}$ and $R_{11}$ each are hydrogen, $C_1-C_4$ alkyl or phenyl; with the proviso that not less than two and not more than four of $R_2$ to $R_6$ are to be substituted with groups other than hydrogen in any one of the compounds of formulae I and Ia and mixtures thereof; and with the additional proviso that when $R_1$, $R_5$ and $R_7$ are hydrogen and n is 0 then:

a if only $R_2$ and $R_3$ are substituted, they cannot be both $CH_3$ or Cl or combinations thereof;

b if only $R_2$ and $R_6$ are substituted they cannot be both $CH_3$, $C_2H_5$, $C_3H_7$, Br or Cl or combinations thereof;

c if $R_2$, $R_4$ and $R_6$ are substituted they cannot be all Br, Cl, $CH_3$ or combinations thereof and if $R_2$ and $R_6$ are both Br then $R_4$ cannot be CN;

d if $R_3$ is $NO_2$ then $R_2$, $R_4$ and $R_6$ cannot be all Br.

A group of novel compounds represented by formula Ib, and of particular interest are graphically illustrated and described as follows:

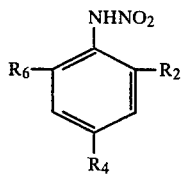

wherein $R_2$ is Br, Cl, F, I, $C_1-C_4$ alkyl, $OCHF_2$, $CF_3$, $SR_8$, $SO_2R_8$ or $COR_9$; $R_4$ is Br, Cl, F, I, $CH_3$, $OCF_3$, $NHCOCH_3$, CN, $SR_8$, $SO_2R_8$, $COR_9$, phenoxy or substituted phenoxy wherein the substituents are $CH_3$, $CF_3$, $CH_3O$, halogen, $NO_2$ or $OCH_2CO_2C_2H_5$; $R_6$ is Br, Cl, F, I or $C_1-C_4$ alkyl; $R_8$ is $C_1-C_6$ alkyl, phenyl or benzyl; $R_9$ is hydrogen, hydroxyl, $C_1-C_3$ alkyl, $C_1-C_3$ alkoxy or phenyl; with the proviso that $R_2$, $R_4$ and $R_6$ cannot be all Br, Cl, $CH_3$ or combinations thereof and with the further proviso that if $R_2$ and $R_6$ are both Br then $R_4$ cannot be CN.

Another group of novel compounds represented by formula Ic and of interest are illustrated and described as follows:

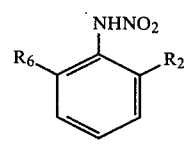

wherein $R_2$ and $R_6$ each are Br, Cl, F, I, $C_1-C_4$ alkyl, $C_1-C_4$ haloalkyl, $C_1-C_4$ haloalkoxy, $SR_8$, $SO_2R_8$ or $COR_{10}$; $R_8$ is $C_1-C_6$ alkyl, phenyl or benzyl; $R_{10}$ is hydrogen, $C_1-C_4$ alkyl or phenyl; with the proviso that $R_2$ and $R_6$ cannot be both $CH_3$, $C_2H_5$, $C_3H_7$, Br or Cl or combinations thereof.

The following group of novel compounds of formula (Id) and of interest are graphically illustrated and described as follows:

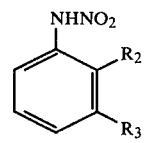

wherein $R_2$ is Br, Cl, F, I, $C_1-C_4$ alkyl, $C_1-C_4$ haloalkyl, $C_1-C_4$ haloalkoxy, $SR_8$, $SO_2R_8$ or $COR_{10}$; $R_3$ is Br, Cl, F, I, $C_1-C_4$ alkyl, $C_1-C_4$ alkoxy, $NH_2$, $NHCOCH_3$, $NO_2$, $SO_2R_8$, CN or $CO_2CH_3$; $R_8$ is $C_1-C_6$ alkyl, phenyl or benzyl; $R_{10}$ is hydrogen, $C_1-C_4$ alkyl or phenyl; with the proviso that $R_2$ and $R_3$ cannot be both $CH_3$ or Cl or combinations thereof.

Another group of novel compounds of formula (Ie) and of interest are graphically illustrated and described as follows:

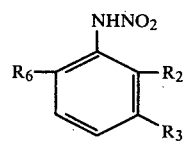

wherein $R_2$ and $R_6$ are Br, Cl, F, I, $C_1-C_4$ alkyl, $C_1-C_4$ haloalkyl, $C_1-C_4$ haloalkoxy, $SO_2R_8$, $SR_8$ or $COR_{10}$; $R_3$ is Br, Cl, F, I, $C_1-C_4$ alkyl, $C_1-C_4$ alkoxy, $NH_2$, NHCOCH₃, NO₂, SO₂R₈, CN or CO₂CH₃; R₈ is C₁-C₆ alkyl, phenyl or benzyl, R₁₀ is hydrogen, C₁-C₄ alkyl or phenyl.

A group of novel compounds represented by formula If and useful in the invention are graphically illustrated and described as follows:

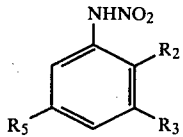 (If)

wherein R₂ is Br, Cl, F, I, C₁-C₄ alkyl, C₁-C₄ haloalkyl, C₁-C₄ haloalkoxy, SR₈, SO₂R₈ or COR₁₀; R₃ is Br, Cl, F, I, C₁-C₄ alkyl, C₁-C₄ alkoxy, NH₂, NHCOCH₃, NO₂, SO₂R₈, CN or CO₂CH₃; R₅ is Br, Cl, F, I, or C₁-C₃ alkyl; R₈ is C₁-C₆ alkyl, phenyl or benzyl; R₁₀ is hydrogen, C₁-C₄ alkyl or phenyl.

Still another group of novel compounds represented by formula Ig, and of interest are graphically illustrated and described as follows:

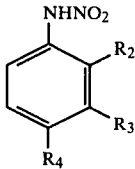 (Ig)

wherein R₂ is Br, Cl, F, I, C₁-C₄ alkyl, C₁-C₄ haloalkyl, C₁-C₄ haloalkoxy, SO₂R₈, SR₈ or COR₁₀; R₃ is Br, Cl, F, I, C₁-C₄ alkyl, C₁-C₄ alkoxy, NH₂, NHCOCH₃, NO₂, SO₂R₈, CN or CO₂CH₃; R₄ is Br, Cl, F, I, C₁-C₂ alkyl, SO₂R₈, COR₉, CN, NHCOCH₃, SO₂NR₁₀R₁₁,

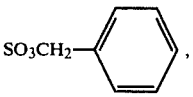

phenoxy or substituted phenoxy and the substituents are CH₃, CF₃, CH₃O, Br, Cl, F, I, NO₂ or OCH₂CO₂C₂H₅; R₈ is C₁-C₆ alkyl, phenyl or benzyl; R₉ is hydrogen, hydroxyl, C₁-C₃ alkyl, C₁-C₃ alkoxy or phenyl; R₁₀ and R₁₁ each are hydrogen, C₁-C₄ alkyl or phenyl.

A group of novel compounds represented by formula Ih and useful in the invention are graphically illustrated and described as follows:

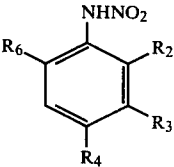 (Ih)

wherein R₂ and R₆ are Br, Cl, F, I, C₁-C₄ alkyl, C₁-C₄ haloalkyl, C₁-C₄ haloalkoxy, SO₂R₈, SR₈ or COR₁₀; R₃ is C₁-C₄ alkyl, C₁-C₄ alkoxy, NH₂, NHCOCH₃, Br, Cl, F, I, NO₂, SO₂R₈, CN or CO₂CH₃; R₄ is Br, Cl, F, I, C₁-C₂ alkyl, SO₂R₈, COR₉, CN, NHCOCH₃, SO₂NR₁₀R₁₁,

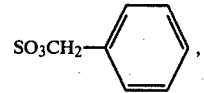

phenoxy or substituted phenoxy and the substituents are CH₃, CF₃, CH₃O, Br, Cl, F, I, NO₂ or OCH₂CO₂—C₂H₅; R₈ is C₁-C₆ alkyl, phenyl or benzyl; R₉ is hydrogen, hydroxyl, C₁-C₃ alkyl, C₁-C₃ alkoxy or phenyl; R₁₀ and R₁₁ are hydrogen, C₁-C₄ alkyl or phenyl; with the proviso that when R₃ is NO₂, then R₂, R₄ and R₆ cannot be all Br.

A group of novel compounds represented by formula Ii and of interest are graphically illustrated and described as follows:

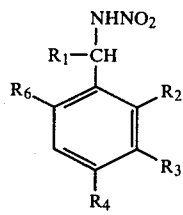 (Ii)

wherein R₁ is hydrogen, C₁-C₃ alkyl, C₁-C₃ haloalkyl, CN, Br, Cl, F, I, NO₂, SO₂R₈, COR₉, phenyl or substituted phenyl and the substituents are CH₃, CF₃, CH₃O, NO₂ or OCH₂CO₂C₂H₅; R₂ and R₆ are hydrogen, Br, Cl, F, I, C₁-C₄ alkyl, C₁-C₄ haloalkyl, C₁-C₄ haloalkoxy, SO₂R₈, SR₈ or COR₁₀; R₃ is hydrogen, C₁-C₄ alkyl, C₁-C₄ alkoxy, NH₂, NHCOCH₃, Br, Cl, F, I, NO₂, SO₂R₈, CN or CO₂CH₃; R₄ is hydrogen, Br, Cl, F, I, C₁-C₂ alkyl, SO₂R₈, COR₉, CN, NHCOCH₃, SO₂NR₁₀R₁₁,

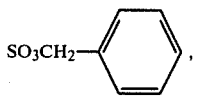

phenoxy or substituted phenoxy and the substituents are CH₃, CF₃, CH₃O, Br, Cl, F, I, NO₂ or OCH₂CO₂C₂H₅; R₈ is C₁-C₆ alkyl, phenyl or benzyl; R₉ is hydrogen, hydroxyl, C₁-C₃ alkyl, C₁-C₃ alkoxy or phenyl; R₁₀ and R₁₁ are hydrogen, C₁-C₄ alkyl or phenyl; with the proviso that not less than two of R₂ to R₆ are to be substituted with groups other than hydrogen.

Still another group of novel compounds of formula Ij useful in the invention are graphically illustrated and described as follows:

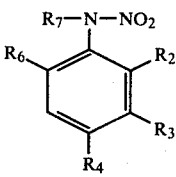 (Ij)

wherein R₂ and R₃ are hydrogen, Br, Cl, F, I, C₁-C₄ alkyl, C₁-C₄ haloalkyl, C₁-C₄ haloalkoxy, SO₂R₈, SR₈, or COR₁₀; R₃ is hydrogen, C₁-C₄ alkyl, C₁-C₄ alkoxy, NH₂, NHCOCH₃, Br, Cl, F, I, NO₂, SO₂R₈, CN or $CO_2CH_3$; $R_4$ is hydrogen, Br, Cl, F, I, $C_1$-$C_2$ alkyl, $SO_2R_8$, $COR_9$, CN, $NHCOCH_3$, $SO_2NR_{10}R_{11}$,

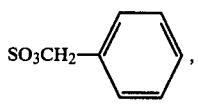

phenoxy or substituted phenoxy and the substituents are $CH_3$, $CF_3$, $CH_3O$, Br, Cl, F, I, $NO_2$ or $OCH_2CO_2C_2H_5$; $R_7$ is $C_1$-$C_{12}$ alkyl optionally substituted with halogen or CN, $C_3$-$C_4$ alkenyl, $C_3$-$C_4$ alkynyl, the methyl esters of lower alkanoic acids or the moiety

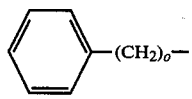

wherein o is an integer of 0,1,2 or 3, and the moiety may optionally be substituted with Br, Cl, F, I, $C_1$-$C_2$ alkyl, $C_1$-$C_2$ alkoxy, ($C_1$-$C_3$ alkyl)$_3$SiCH$_2$—, or $NO_2$; $R_8$ is $C_1$-$C_6$ alkyl, phenyl or benzyl; $R_9$ is hydrogen, hydroxyl, $C_1$-$C_3$ alkyl, $C_1$-$C_3$ alkoxy or phenyl; $R_{10}$ and $R_{11}$ are hydrogen, $C_1$-$C_4$ alkyl or phenyl; with the provisos that when; a $R_2$, $R_4$ and $R_6$ are Br then $R_7$ cannot be $CH_3$; b and when $R_2$ and $R_6$ are both Br then $R_7$ cannot be $C_1$-$CHd$ 4 alkyl, and o cannot be an integer of 1,2 or 3; c and when $R_2$ and $R_6$ are both $CH_3$ then o cannot be 3.

The novel group of compounds represented by formula Ik and of particular interest are graphically illustrated and described as follows:

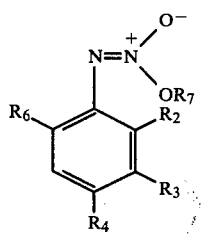 (Ik)

wherein $R_2$ and $R_6$ are hydrogen, Br, Cl, F, I, $C_1$-$C_4$ alkyl, $C_1$-$C_4$ haloalkyl, $C_1$-$C_4$ haloalkoxy, $SO_2R_8$, $SR_8$ or $COR_{10}$; $R_3$ is hydrogen, $C_1$-$C_4$ alkyl, $C_1$-$C_4$ alkoxy, $NH_2$, $NHCOCH_3$, Br, Cl, F, I, $NO_2$, $SO_2R_8$, CN or $COCH_3$; $R_4$ is hydrogen, Br, Cl, F, I, $C_1$-$C_2$ alkyl, $SO_2R_8$, $COR_9$, CN, $NHCOCH_3$, $SO_2NR_{10}R_{11}$,

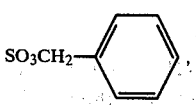

phenoxy or substituted phenoxy and the substituents are $CH_3$, $CF_3$, $CH_3O$, Br, Cl, F, I, $NO_2$ or $OCH_2CO_2C_2H_5$; $R_7$ is $C_1$-$C_{12}$ alkyl optionally substituted with halogen or CN, $C_3$-$C_4$ alkenyl, $C_3$-$C_4$ alkynyl, the methyl esters of lower alkanoic acids or the moiety

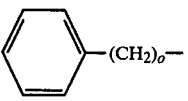

wherein o is an integer of 0,1,2 or 3, and the moiety may optionally be substituted with Br, Cl, F, I, $C_1$-$C_2$ alkyl, $C_1$-$C_2$ alkoxy, ($C_1$-$C_3$ alkyl)$_3$SiCH$_2$— or $NO_2$; $R_8$ is $C_1$-$C_6$ alkyl; phenyl or benzyl; $R_9$ is hydrogen, hydroxyl, $C_1$-$C_3$ alkyl, $C_1$-$C_3$ alkoxy or phenyl; $R_{10}$ and $R_{11}$ are hydrogen, $C_1$-$C_4$ alkyl or phenyl.

The hereinabove identified compounds of formulae I and Ia may also form a group of novel inorganic and organic salts represented by formula II and useful in the invention, graphically illustrated and described as follows:

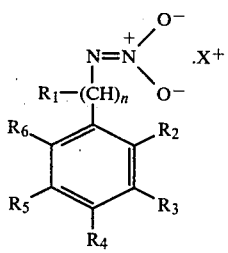 (II)

wherein n is an integer of 0 or 1; $R_1$ is hydrogen, $C_1$-$C_3$ alkyl, $C_1$-$C_3$ haloalkyl, CN, Br, Cl, F, I, $NO_2$, $SO_2R_8$, $COR_9$, phenyl or substituted phenyl and the substituents are $CH_3$, $CF_3$, $CH_3O$, Br, Cl, F, I, $NO_2$ or $OCH_2CO_2C_2H_5$; $R_2$ and $R_6$ are hydrogen, halogen, $C_1$-$C_4$ alkyl, $C_1$-$C_4$ haloalkyl, $C_1$-$C_4$ haloalkoxy, $SO_2R_8$, $SR_8$ or $COR_{10}$; $R_3$ is hydrogen, $C_1$-$C_4$ alkyl, $C_1$-$C_4$ alkoxy, $NH_2$, $NHCOCH_3$, Br, Cl, F, I, $NO_2$, $SO_2R_8$, CN or $CO_2CH_3$; $R_4$ is hydrogen, Br, Cl, F, I, $C_1$-$C_2$ alkyl, $SO_2R_8$, $COR_9$, CN, $NHCOCH_3$, $SO_2NR_{10}R_{11}$, $OCF_3$,

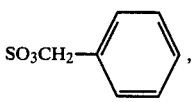

phenoxy or substituted phenoxy and the substituents are $CH_3$, $CF_3$, $CH_3O$, Br, Cl, F, I, $NO_2$ or $OCH_2CO_2C_2H_5$; $R_5$ is hydrogen, $C_1$-$C_3$ alkyl, Br, Cl, F, or I; $X^+$ is inorganic or organic;

when X is inorganic, it is alkali metals, alkaline earth metals, Co, Zn, or Ag;

when the cation $X^+$ is organic, $X^+$ is represented by formula IIIa

 (IIIa)

wherein $R_a$ is hydrogen, $C_1$-$C_{30}$ alkyl straight chain or branched [optionally mono- or disubstituted with HO—, $CH_3O_2C$—, $CH_3S$—, $C_3$-$C_{18}$alkenylaminoalkylene ($C_1$-$C_3$), $H_2N$, $(CH_3)_2N$—,

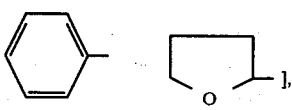

$C_3-C_6$ alkenyl, $C_3-C_6$ alkynyl, $C_3-C_6$ cycloalkyl,

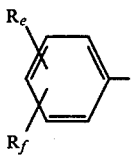

wherein $R_e$ and $R_f$ each may be H, $CH_3$ or n-$C_{16}H_{33}SO_2-$; $R_b$ is hydrogen, $C_1-C_{30}$ alkyl straight chain or branched [optionally mono- or disubstituted with HO— or

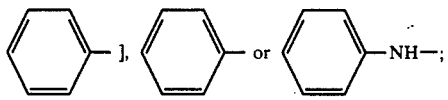

$R_c$ is hydrogen, $C_1-C_{30}$ alkyl straight chain or branched [optionally mono- or disubstituted with HO— or

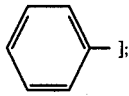

$R_d$ is hydrogen, $C_1-C_{30}$ alkyl straight chain or branched [optionally substituted with HO—, CL— or

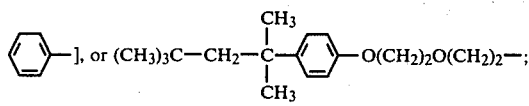

and when $R_a$ and $R_b$ are taken together with the nitrogen they are attached to they represent a moiety of

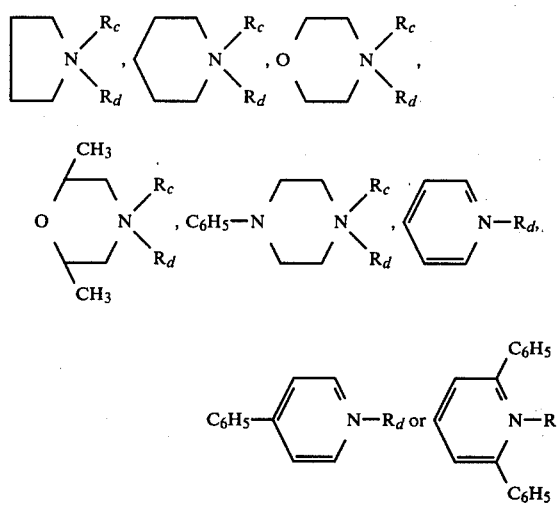

wherein $R_c$ and $R_d$ are defined as above;

organic cation X+ may also be imidazolium, pyridinium, quinolinium, dithiolium, tetrazolium or be represented by formula IIIb

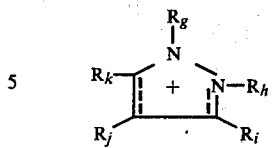
(IIIb)

wherein $R_g$ and $R_h$ each are $C_1-C_3$ alkyl; $R_j$ is hydrogen, halogen, $C_1-C_3$ alkyl or $C_1-C_3$ alkoxy; $R_i$ and $R_k$ each are hydrogen $C_1-C_6$ alkyl straight chain or branched, $C_3-C_6$ cycloalkyl,

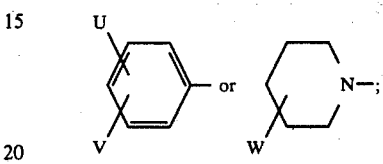

wherein U and V each are hydrogen, halogen, $C_1-C_3$ alkyl, $C_1-C_3$ alkoxy, CN or $CF_3$; W is hydrogen or $C_1-C_3$ alkyl; and each ⇌ symbol represents a single or double bond, wherein if both are single bonds then the cations are pyrazolidinium cations represented by formula IIIc

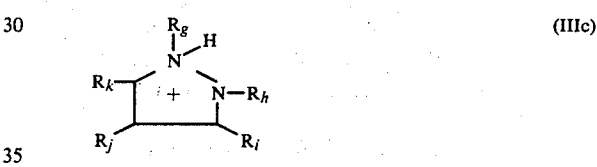
(IIIc)

wherein $R_g$ and $R_k$ are as defined above; and
X+ may also be represented by formulae IIIf and IIIg $R_1-P^+(Rm)_3$         IIIf wherein $R_1$ is $C_1-C_6$ alkyl,

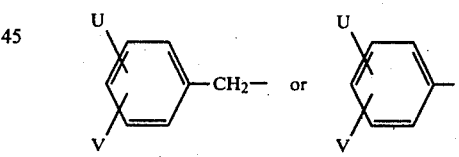

wherein U and V are as hereinabove defined; $R_m$ is $C_1-C_6$ alkyl or

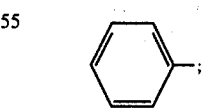

$S^+R_aR_bR_c$ (IIIg) and $I^+R_aR_b$ (IIIh), wherein $R_a$, $R_b$ and $R_c$ are as hereinabove defined; with the proviso that not less than two of $R_2$ to $R_6$ are to be substituted with groups other than hydrogen in any one of the compounds of formula II.

A group of novel salts represented by formulae II, IV and IVa in the disclosure and of special interest are graphically illustrated and described as follows:

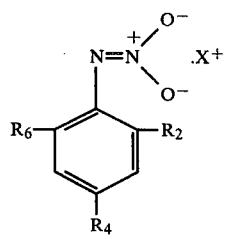

$R_2$ is Br, Cl, F, I, $C_1$–$C_4$ alkyl, $OCHF_2$, $CF_3$, $SR_8$, $SO_2R_8$ or $COR_9$; $R_4$ is Br, Cl, F, I, $CH_3$, $OCF_3$, $NHCOCH_3$, CN, $SR_8$, $SO_2R_8$, $COR_9$, phenoxy or substituted phenoxy and the substituents are $CH_3$, $CF_3$, $OCH_3$, Br, Cl, F, I or $C_1$–$C_4$ alkyl; $R_6$ is Br, Cl, F, I or $C_1$–$C_4$ alkyl; $R_8$ is $C_1$–$C_6$ alkyl, phenyl or benzyl; $R_9$ is hydrogen, hydroxyl, $C_1$–$C_3$ alkyl, $C_1$–$C_3$ alkoxy or phenyl; and cation $X^+$ is inorganic or organic, when X is inorganic, it is alkali metals, alkaline earth metals, Co, Zn, or Ag;

when the cation $X^+$ is organic, $X^+$ is represented by formula IIIa $$N^+R_aR_bR_cR_d \qquad (IIIa)$$

wherein $R_a$ is hydrogen, $C_1$–$C_{30}$ alkyl straight chain or branched [optionally mono- or disubstituted with HO—, $CH_3O_2C$—, $CH_3S$—, $C_3$–$C_{18}$alkenylaminoalkylene ($C_1$–$C_3$), $H_2N$, $(CH_3)_2N$—,

$C_3$–$C_6$ alkenyl, $C_3$–$C_6$ alkynyl, $C_3$–$C_6$ cyloalkyl,

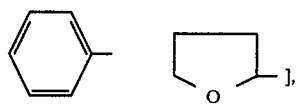

wherein $R_e$ and $R_f$ each may be H, $CH_3$ or n—$C_{16}H_{33}SO_2$—; $R_b$ is hydrogen, $C_1$–$C_{30}$ alkyl straight chain or branched [optionally mono- or disubstituted with HO— or

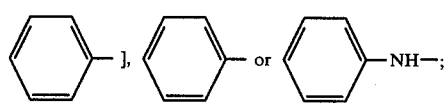

$R_c$ is hydrogen, $C_14$ $C_{30}$ alkyl straight chain or branched [optionally mono- or disubstituted with HO— or

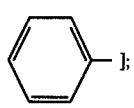

$R_d$ is hydrogen, $C_1$–$C_{30}$ alkyl straight chain or branched [optionally substituted with HO—, Cl— or

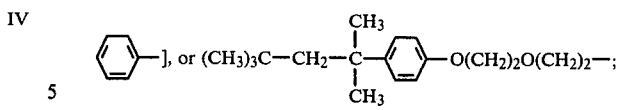

and when $R_a$ and $R_b$ are taken together with the nitrogen they are attached to they represent a moiety of

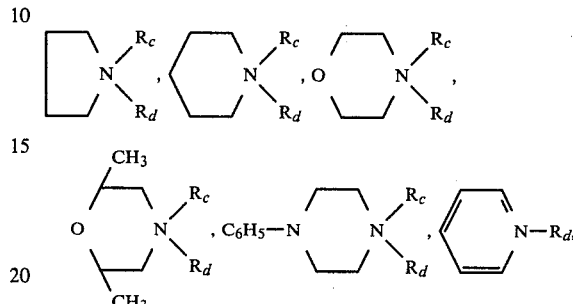

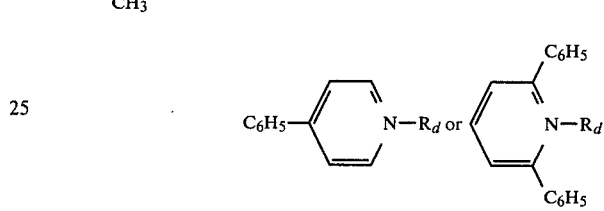

wherein $R_c$ and $R_d$ are defined as above;

organic cation $X^+$ may also be imidazolium, pyridinium, quinolinium, dithiolium, tetrazolium or be represented by formula IIIb

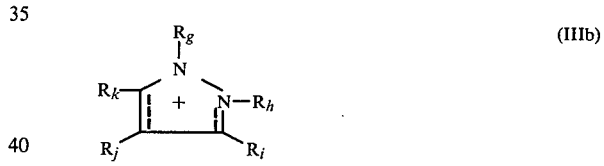

wherein $R_g$ and $R_h$ each are $C_1$–$C_3$ alkyl; $R_j$ is hydrogen, halogen, $C_1$–$C_3$ alkyl or $C_1$–$C_3$ alkoxy; $R_i$ and $R_k$ each are hydrogen $C_1$–$C_6$ alkyl straight chain or branched, $C_3$–$C_6$ cycloalkyl,

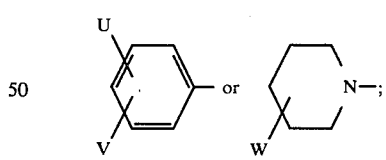

wherein U and V each are hydrogen, halogen, $C_1$–$C_3$ alkyl, $C_1$–$C_3$ alkoxy, CN or $CF_3$; W is hydrogen or $C_1$–$C_3$ alkyl; and each $=$ symbol represents a single or double bond, wherein if both are single bonds then the cations are pyrazolidinium cations represented by formula IIIc

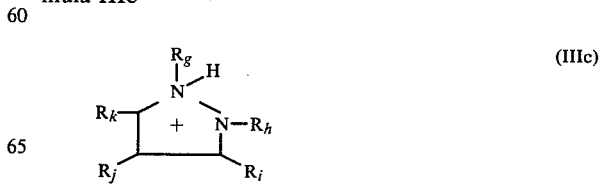

wherein $R_g$ and $R_k$ are as defined above; and

X+ may also be represented by formulae IIIf and IIIg

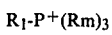 IIIf wherein $R_1$ is $C_1$–$C_6$ alkyl,

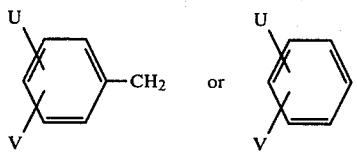

wherein U and V are as hereinabove defined; $R_m$ is $C_1$–$C_6$ alkyl or

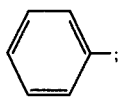

$S^+R_aR_bR_c$(IIIg) and $I^+R_aR_b$(IIIh), wherein $R_a$, $R_b$ and $R_c$ are as hereinabove defined; with the provisos that when $R_2$, $R_4$ and $R_6$ each are Br, Cl or at least one of them is $CH_3$, cation X+ cannot be $Ba^{2+}$; and when $R_2$, $R_4$ and $R_6$ are Br, Cl or mixtures thereof, X+ cannot be $Na^+$; and when $R_2$, $R_4$ and $R_6$ each are Br, X+ cannot be $K^+$, $Ag^+$, $NH_4^+$ or anilino.

Another group of novel salts represented by formula V are of interest and are graphically illustrated and described as follows:

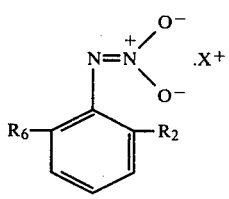 (V)

wherein $R_2$ and $R_6$ each are Br, Cl, F, I, $C_1$–$C_4$ alkyl, $C_1$–$C_4$ haloalkyl, $C_1$–$C_4$ haloalkoxy, $SR_8$, $SO_2R_8$ or $COR_{10}$; $R_8$ is $C_1$–$C_6$ alkyl, phenyl or benzyl; $R_{10}$ is hydrogen, $C_1$–$C_4$ alkyl or phenyl; X is inorganic or organic, when X is inorganic, it is alkali metals, alkaline earth metals, Co, Zn, or Ag;

when the cation X+ is organic, X+ is represented by formula IIIa

 (IIIa)

wherein $R_a$ is hydrogen, $C_1$–$C_{30}$ alkyl straight chain or branched [optionally mono- or disubstituted with HO—, $CH_3O_2C$—, $CH_3S$—, $C_3$–$C_{18}$alkenylaminoalkylene ($C_1$–$C_3$), $H_2N$, $(CH_3)_2N$—,

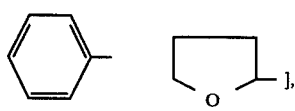

$C_3$–$C_6$ alkenyl, $C_3$–$C_6$ alkenyl, $C_3$–$C_6$ cycloalkyl,

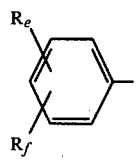

wherein $R_e$ and $R_f$ each may be H, $CH_3$ or n-$C_{16}H_{33}SO_2$—; $R_b$ is hydrogen, $C_1$–$C_{30}$ alkyl straight chain or branched [optionally mono- or disubstituted with HO— or

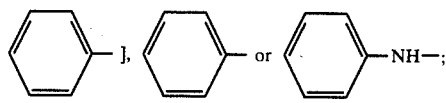

$R_c$ is hydrogen, $C_1$–$C_{30}$ alkyl straight chain or branched [optionally mono- or disubstituted with HO— or

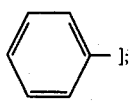

$R_d$ is hydrogen, $C_1$–$C_{30}$ alkyl straight chain or branched [optionally substituted with HO—, Cl— or

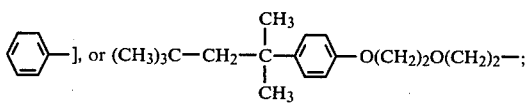

and when $R_a$ and $R_b$ are taken together with the nitrogen they are attached to they represent a moiety of

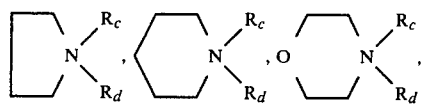

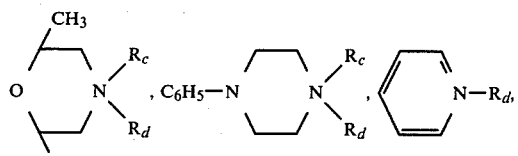

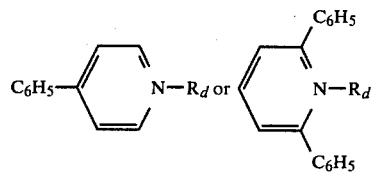

wherein $R_c$ and $R_d$ are defined as above;

organic cation X+ may also be imidazolium, pyridinium, quinolinium, dithiolium, tetrazolium or be represented by formula IIIb

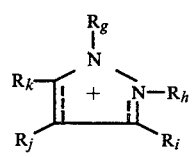 (IIIb)

wherein $R_g$ and $R_h$ each are $C_1$-$C_3$ alkyl; $R_j$ is hydrogen, halogen, $C_1$-$C_3$ alkyl or $C_1$-$C_3$ alkoxy; $R_i$ and $R_k$ each are hydrogen $C_1$-$C_6$ alkyl straight chain or branched, $C_3$-$C_6$ cycloalkyl,

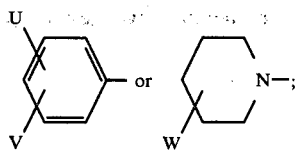

wherein U and V each are hydrogen, halogen, $C_1$-$C_3$ alkyl, $C_1$-$C_3$ alkoxy, CN or $CF_3$; W is hydrogen or $C_1$-$C_3$ alkyl; and each $=$ symbol represents a single or double bond, wherein if both are single bonds then the cations are pyrazolidinium cations represented by formula IIIc

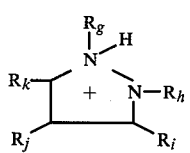 (IIIc)

wherein $R_g$ to $R_k$ are as defined above; and
$X^+$ may also be represented by formulae IIIf and IIIg

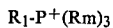 IIIf wherein $R_1$ is $C_1$-$C_6$ alkyl,

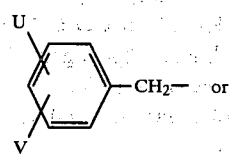

wherein U and V are as hereinabove defined; Rm is $C_1$-$C_6$ alkyl or

$S^+$-$R_a R_b R_c$ (IIIg) and $I^+$-$R_a R_b$ (IIIh), wherein $R_a$, $R_b$ and $R_c$ are as hereinabove defined; and with the proviso that when $R_2$ and $R_6$ both are Br, then $X^+$ cannot be $Na^+$, $K^+$, $Li^+$, $Ba^{++}$, $Sr^{++}$, or $NH_4^+$.

The following group of novel salts of formula (VI) and of interest are graphically illustrated and described as follows:

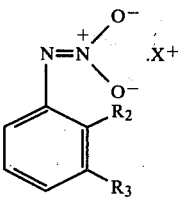 (VI)

wherein $R_2$ is Br, Cl, F, I, $C_1$-$C_4$ alkyl, $C_1$-$C_4$ haloalkyl, $C_1$-$C_4$ haloalkoxy, $SR_8$, $SO_2R_8$ or $COR_{10}$; $R_3$ is Br, Cl, F, I, $C_1$-$C_4$ alkyl, $C_1$-$C_4$ alkoxy, $NH_2$, $NHCOCH_3$, $NO_2$, $SO_2R_8$, CN or $CO_2CH_3$; $R_8$ is $C_1$-$C_6$ alkyl, phenyl or benzyl; $R_{10}$ is hydrogen, $C_1$-$C_4$ alkyl or phenyl; $X^+$ is inorganic or organic, when X is inorganic, it is alkali metals, alkaline earth metals, Co, Zn, or Ag;

when the cation $X^+$ is organic, $X^+$ is represented by formula IIIa $$N^+ R_a R_b R_c R_d \qquad \text{(IIIa)}$$

wherein $R_a$ is hydrogen, $C_1$-$C_{30}$ alkyl straight chain or branched [optionally mono- or disubstituted with HO—, $CH_3O_2C$—, $CH_3S$—, $C_3$-$C_{18}$alkenylaminoalkylene ($C_1$-$C_3$), $H_2N$, $(CH_3)_2N$—,

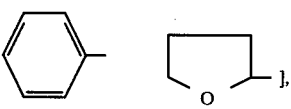

$C_3$-$C_6$ alkenyl, $C_3$-$C_6$ alkynyl, $C_3$-$C_6$ cycloalkyl,

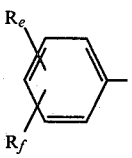

wherein $R_e$ and $R_f$ each may be H, $CH_3$ or n—$C_{16}H_{33}SO_2$—; $R_b$ is hydrogen, $C_1$-$C_{30}$ alkyl straight chain or branched [optionally mono- or disubstituted with HO— or

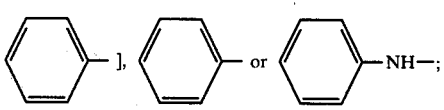

$R_c$ is hydrogen, $C_1$-$C_{30}$ alkyl straight chain or branched [optionally mono- or disubstituted with HO— or

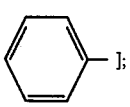

$R_d$ is hydrogen, $C_1$-$C_{30}$ alkyl straight chain or branched [optionally substituted with HO—, Cl— or

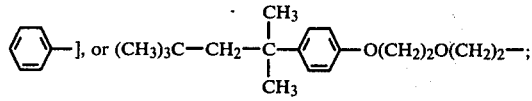, or $(CH_3)_3C-CH_2-\underset{\underset{CH_3}{|}}{\overset{\overset{CH_3}{|}}{C}}-\phantom{X}-O(CH_2)_2O(CH_2)_2-;$ and when $R_a$ and $R_b$ are taken together with the nitrogen they are attached to they represent a moiety of

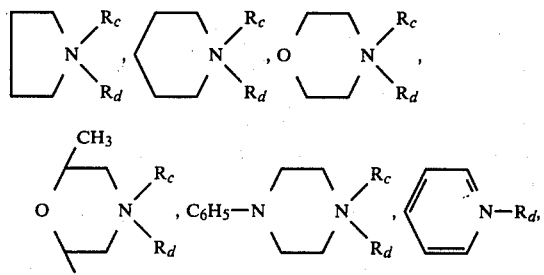

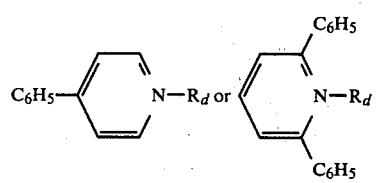

wherein $R_c$ and $R_d$ are defined as above;

organic cation $X^+$ may also be imidazolium, pyridinium, quinolinium, dithiolium, tetrazolium or be represented by formula IIIb

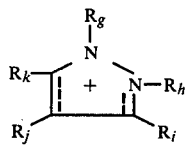 (IIIb)

wherein $R_g$ and $R_h$ each are $C_1$-$C_3$ alkyl; $R_j$ is hydrogen, halogen, $C_1$-$C_3$ alkyl or $C_1$-$C_3$ alkoxy; $R_i$ and $R_k$ each are hydrogen $C_1$-$C_6$ alkyl straight chain or branched, $C_3$-$C_6$ cycloalkyl,

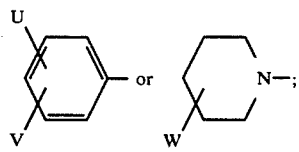

wherein U and V each are hydrogen, halogen, $C_1$-$C_3$ alkyl, $C_1$-$C_3$ alkoxy, CN or $CF_3$; W is hydrogen or $C_1$-$C_3$ alkyl; and each ⇌ symbol represents a single or double bond, wherein if both are single bonds then the cations are pyrazolidinium cations represented by formula IIIc

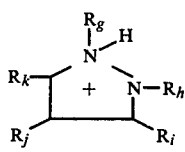 (IIIc)

wherein $R_g$ to $R_k$ are as defined above, and $X^+$ may also be represented by formulae IIIf and IIIg $R_1$-$P^+$-$(Rm)_3$           IIIf wherein $R_1$ is $C_1$-$C_6$ alkyl,

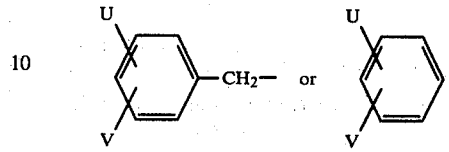

wherein U and V are as hereinabove defined; Rm is $C_1$-$C_6$ alkyl or

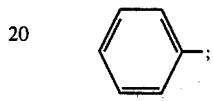

$S^+R_aR_bR_c$ (IIIg) and $I^+R_aR_b$ (IIIh), wherein $R_a$, $R_b$ and $R_c$ are as hereinabove defined; and with the proviso that when $R_2$ and $R_3$ are both $CH_3$, $X^+$ cannot be $Li^+$.

A group of novel salts represented by formula VII and useful in the invention are graphically illustrated and described as follows:

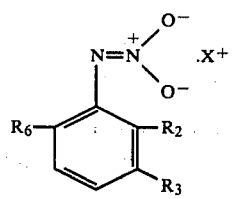 (VII)

wherein $R_2$ and $R_6$ each are Br, Cl, F, I, $C_1$-$C_4$ alkyl, $C_1$-$C_4$ haloalkyl, $C_1$-$C_4$ haloalkoxy, $SR_8$, $SO_2R_8$ or $COR_{10}$; $R_3$ is Br, Cl, F, I, $C_1$-$C_4$ alkyl, $C_1$-$C_4$ alkoxy, $NH_2$, $NHCOCH_3$, $NO_2$, $SO_2R_8$, CN or $CO_2CH_3$; $R_8$ is $C_1$-$C_6$ alkyl, phenyl or benzyl; $R_{10}$ is hydrogen, $C_1$-$C_4$ alkyl or phenyl; $X^+$ is inorganic or organic, when X is inorganic, it is alkali metals, alkaline earth metals, Co, Zn, or Ag;

when the cation $X^+$ is organic, $X^+$ is represented by formula IIIa $N^+R_aR_bR_cR_d$           (IIIa)

wherein $R_a$ is hydrogen, $C_1$-$C_{30}$ alkyl straight chain or branched [optionally mono- or disubstituted with HO—, $CH_3O_2C$—, $CH_3S$—, $C_3$-$C_{18}$alkenylaminoalkylene ($C_1$-$C_3$), $H_2N$, $(CH_3)_2N$—,

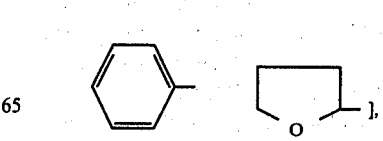

$C_3$-$C_6$ alkenyl, $C_3$-$C_6$ alkynyl, $C_3$-$C_6$ cycloalkyl,

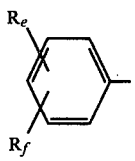

wherein $R_e$ and $R_f$ each may be H, $CH_3$ or n—$C_{16}H_{33}SO_2$—; $R_b$ is hydrogen, $C_1$-$C_{30}$ alkyl straight chain or branched [optionally mono- or disubstituted with HO— or

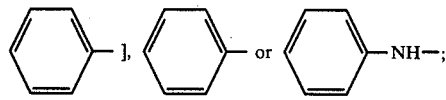

$R_c$ is hydrogen, $C_1$-$C_{30}$ alkyl straight chain or branched [optionally mono- or disubstituted with HO— or

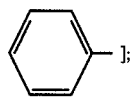

$R_d$ is hydrogen, $C_1$-$C_{30}$ alkyl straight chain or branched [optionally substituted with HO—, Cl— or

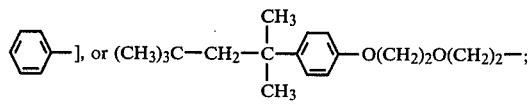

and when $R_a$ and $R_b$ are taken together with the nitrogen they are attached to they represent a moiety of

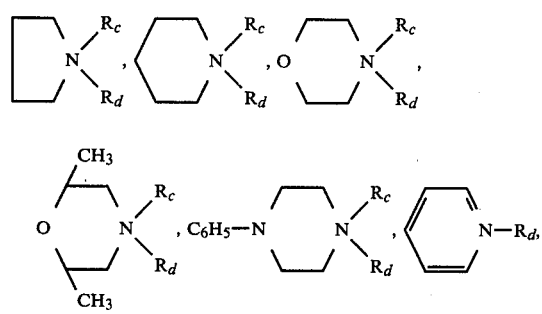

wherein $R_c$ and $R_d$ are defined as above;

organic cation X+ *may also be imidazolium, pyridinium, quinolinium, dithiolium, tetrazolium or be represented by formula IIIb*

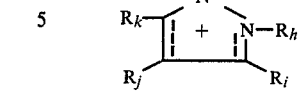
(IIIb)

wherein $R_g$ and $R_h$ each are $C_1$-$C_3$ alkyl; $R_j$ is hydrogen, halogen, $C_1$-$C_3$ alkyl or $C_1$-$C_3$ alkoxy; $R_i$ and $R_k$ each are hydrogen $C_1$-$C_6$ alkyl straight chain or branched, $C_3$-$C_6$ cycloalkyl,

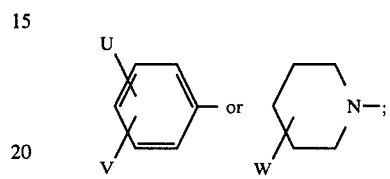

wherein U and V each are hydrogen, halogen, $C_1$-$C_3$ alkyl, $C_1$-$C_3$ alkoxy, CN or $CF_3$; W is hydrogen or $C_1$-$C_3$ alkyl; and each $=$ symbol represents a single or double bond, wherein if both are single bonds then the cations are pyrazolidinium cations represented by formula IIIc

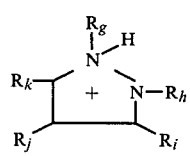
(IIIc)

wherein $R_g$ to $R_k$ are as defined above, and

X+ may also be represented by formulae IIIf and IIIg $$R_1\text{-}P^+(Rm)_3 \qquad \text{IIIf}$$

wherein $R_1$ is $C_1$-$C_6$ alkyl,

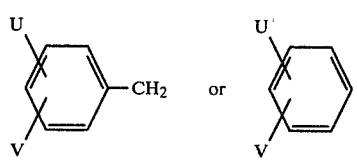

wherein U and V are as hereinabove defined, Rm is $C_1$-$C_6$ alkyl or

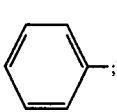

$S^+R_aR_bR_c$ (IIIg) and $I^+R_aR_b$(IIIh), wherein $R_a$, $R_b$ and $R_c$ are as hereinabove defined.

A group of novel salts represented by formula VIII and useful in the invention are graphically illustrated and described as follows:

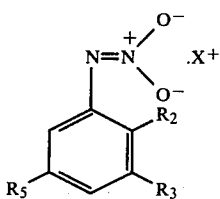 (VIII)

wherein R$_2$ is Br, Cl, F, I, C$_1$-C$_4$ alkyl, C$_1$-C$_4$ haloalkyl, C$_1$-C$_4$ haloalkoxy, SR$_8$, SO$_2$R$_8$ or COR$_{10}$; R$_3$ is Br, Cl, F, I, C$_1$-C$_4$ alkyl, C$_1$-C$_4$ alkoxy, NH$_2$, NHCOCH$_3$, NO$_2$, SO$_2$R$_8$, CN or CO$_2$CH$_3$; R$_5$ is Br, Cl, F, I or C$_1$-C$_3$ alkyl; R$_8$ is C$_1$-C$_6$ alkyl, phenyl or benzyl; R$_{10}$ is hydrogen, C$_1$-C$_4$ alkyl or phenyl; X$^+$ is inorganic or organic, when X is inorganic, it is alkali metals, alkaline earth metals, Co, Zn, or Ag;

when the cation X$^+$ is organic, X$^+$ is represented by formula IIIa $$N^+R_aR_bR_cR_d \qquad (IIIa)$$

wherein R$_a$ is hydrogen, C$_1$-C$_{30}$ alkyl straight chain or branched [optionally mono- or disubstituted with HO—, CH$_3$O$_2$C—, CH$_3$S—, C$_3$-C$_{18}$alkenylaminoalkylene (C$_1$-C$_3$), H$_2$N, (CH$_3$)$_2$N—,

C$_3$-C$_6$ alkenyl, C$_3$-C$_6$ alkynyl, C$_3$-C$_6$ cycloalkyl,

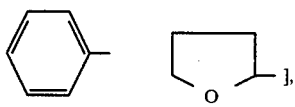

wherein R$_e$ and R$_f$ each may be H, CH$_3$ or n—C$_{16}$H$_{33}$SO$_2$—; R$_b$ is hydrogen, C$_1$-C$_{30}$ alkyl straight chain or branched [optionally mono- or disubstituted with HO— or

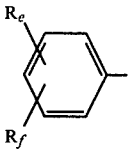

R$_c$ is hydrogen, C$_1$-C$_{30}$ alkyl straight chain or branched [optionally mono- or disubstituted with HO— or

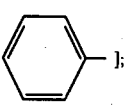

R$_d$ is hydrogen, C$_1$-C$_{30}$ alkyl straight chain or branched [optionally substituted with HO—, Cl— or

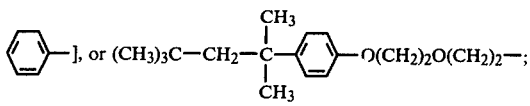

and when R$_a$ and R$_b$ are taken together with the nitrogen they are attached to they represent a moiety of

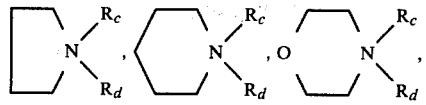

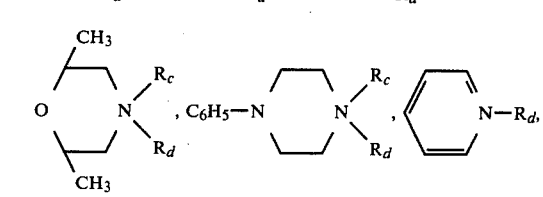

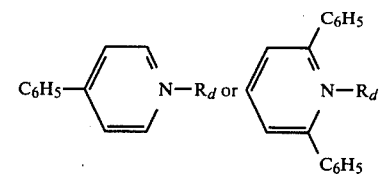

wherein R$_c$ and R$_d$ are defined as above;

organic cation X$^+$ may also be imidazolium, pyridinium, quinolinium, dithiolium, tetrazolium or be represented by formula IIIb

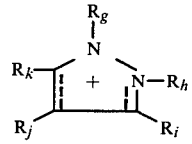 (IIIb)

wherein R$_g$ and R$_h$ each are C$_1$-C$_3$ alkyl; R$_j$ is hydrogen, halogen, C$_1$-C$_3$ alkyl or C$_1$-C$_3$ alkoxy; R$_i$ and R$_k$ each are hydrogen C$_1$-C$_6$ alkyl straight chain or branched, C$_3$-C$_6$ cycloalkyl,

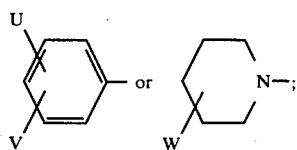

wherein U and V each are hydrogen, halogen, C$_1$-C$_3$ alkyl, C$_1$-C$_3$ alkoxy, CN or CF$_3$; W is hydrogen or C$_1$-C$_3$ alkyl; and each $=$ symbol represents a single or double bond, wherein if both are single bonds then the cations are pyrazolidinium cations represented by formula IIIc

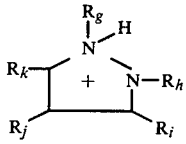 (IIIc)

wherein R$_g$ to R$_k$ are as defined above, and

X+ may also be represented by formulae IIIf and IIIg

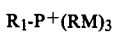  IIIf wherein $R_1$ is $C_1-C_6$ alkyl,

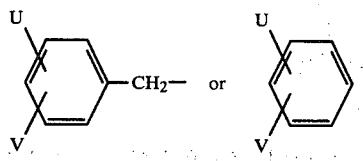

wherein U and V are as hereinabove defined; Rm is $C_1-C_6$ alkyl or

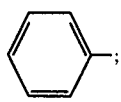;

$S^+R_aR_bR_c$ (IIIg) and $I^+R_aR_b$ (IIIh), wherein $R_a$, $R_b$ and $R_c$ are as hereinabove defined.

Another group of novel salts represented by formula IX and useful in the invention are graphically illustrated and described as follows:

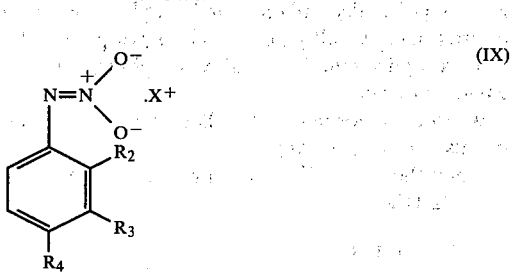 (IX)

wherein $R_2$ is Br, Cl, F, I, $C_1-C_4$ alkyl, $C_1-C_4$ haloalkyl, $C_1-C_4$ haloalkoxy, $SR_8$, $SO_2R_8$ pr $COR_{10}$; $R_3$ is Br, Cl, F, I, $C_1-C_4$ alkyl, $C_1-C_4$ alkoxy, $NH_2$, $NHCOCH_3$, $NO_2$, $SO_2R_8$, CN or $CO_2CH_3$; $R_4$ is Br, Cl, F, I, $C_1-C_2$ alkyl, $SO_2NR_{10}R_{11}$, $NHCOCH_3$, CN, $SR_8$, $SO_2R_8$, $COR_9$,

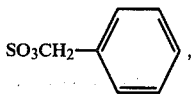, phenoxy or substituted phenoxy and the substituents are $CH_3$, $CF_3$, $OCH_3$, Br, Cl, F, I, $NO_2$ or $OCH_2CO_2C_2H_5$; $R_8$ is $C_1-C_6$ alkyl, phenyl or benzyl; $R_9$ is hydrogen, hydroxyl, $C_1-C_3$ alkyl, $C_1-C_3$ alkoxy or phenyl; $R_{10}$ and $R_{11}$ each are hydrogen, $C_1-C_4$ alkyl or phenyl; X+ is inorganic or organic, when X is inorganic, it is alkali metals, alkaline earth metals, Co, Zn, or Ag;

when the cation X+ is organic, X+ is represented by formula IIIa

 (IIIa)

wherein $R_a$ is hydrogen, $C_1-C_{30}$ alkyl straight chain or branched [optionally mono- or disubstituted with HO—, $CH_3O_2C$—, $CH_3S$—, $C_3-C_{18}$alkenylaminoalkylene ($C_1-C_3$), $H_2N$, $(CH_3)_2N$—,

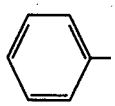 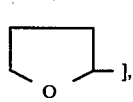], $C_3-C_6$ alkenyl, $C_3-C_6$ alkynyl, $C_3-C_6$ cycloalkyl,

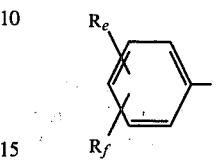

wherein $R_e$ and $R_f$ each may be H, $CH_3$ or n—$C_{16}H_{33}SO_2$—; $R_b$ is hydrogen, $C_1-C_{30}$ alkyl straight chain or branched [optionally mono- or disubstituted with HO— or

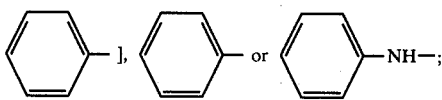;

$R_c$ is hydrogen, $C_1-C_{30}$ alkyl straight chain or branched [optionally mono- or disubstituted with HO— or

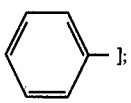;

$R_d$ is hydrogen, $C_1-C_{30}$ alkyl straight chain or branched [optionally substituted with HO—, Cl— or

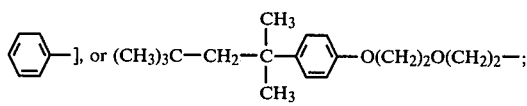;

and when $R_a$ and $R_b$ are taken together with the nitrogen they are attached to they represent a moiety of

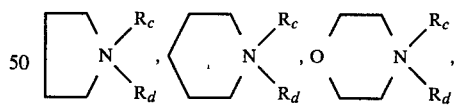

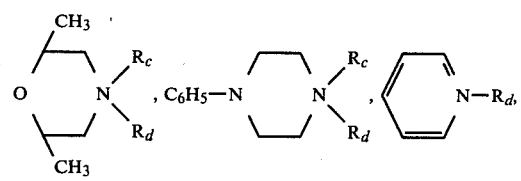

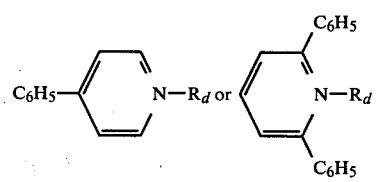

wherein $R_c$ and $R_d$ are defined as above;

organic cation X+ may also be imidazolium, pyridinium, quinolinium, dithiolium, tetrazolium or be represented by formula IIIb

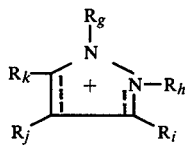
(IIIb)

wherein $R_g$ and $R_h$ each are $C_1$-$C_3$ alkyl; $R_j$ is hydrogen, halogen, $C_1$-$C_3$ alkyl or $C_1$-$C_3$ alkoxy; $R_i$ and $R_k$ each are hydrogen $C_1$-$C_6$ alkyl straight chain or branched, $C_3$-$C_6$ cycloalkyl,

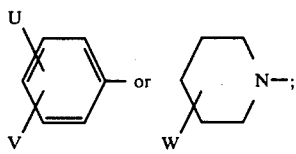

wherein U and V each are hydrogen, halogen, $C_1$-$C_3$ alkyl, $C_1$-$C_3$ alkoxy, CN or $CF_3$; W is hydrogen or $C_1$-$C_3$ alkyl; and each $\rightleftharpoons$ symol represents a single or double bond, wherein if both are single bonds then the cations are pyrazolidinium cations represented by formula IIIc

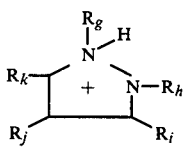
(IIIc)

wherein $R_g$ to $R_k$ are as defined above, and X+ may also be represented by formulae IIIf and IIIg $R_1$-$P^+(R_m)_3$  IIIf wherein $R_1$ is $C_1$-$C_6$ alkyl,

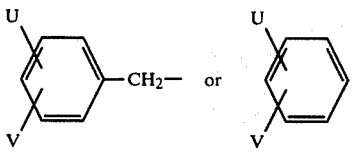

wherein U and V are as hereinabove defined; $R_m$ is $C_1$-$C_6$ alkyl or

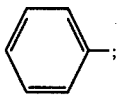;

$S^+R_aR_bR_c$(IIIg) and $I^+R_aR_b$(IIIh), wherein $R_a$, $R_b$ and $R_c$ are as hereinabove defined.

Another group of novel salts represented by formula (X) and of interest are graphically illustrated and described as follows:

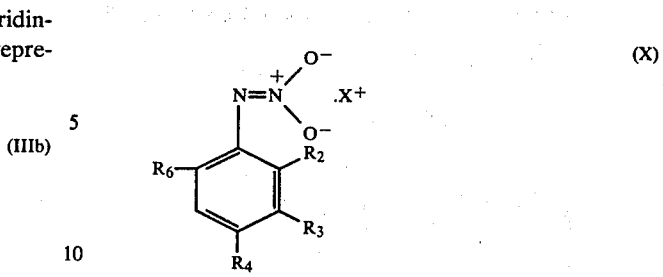
(X)

wherein $R_2$ and $R_6$ are Br, Cl, F, I, $C_1$-$C_4$ alkyl, $C_1$-$C_4$ haloalkyl, $C_1$-$C_4$ haloalkoxy, $SO_2R_8$, $SR_8$ or $COR_{10}$; $R_3$ is $C_1$-$C_4$ alkyl, $C_1$-$C_4$ alkoxy, $NH_2$, $NHCOCH_3$, Br, Cl, F, I, $NO_2$, $SO_2R_8$, CN or $CO_2CH_3$; $R_4$ is Br, Cl, F, I, $C_1$-$C_2$ alkyl, $SO_2R_8$, $COR_9$, CN, $NHCOCH_3$, $SO_2NR_{10}R_{11}$,

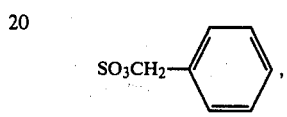

phenoxy or substituted phenoxy and the substituents are $CH_3$, $CF_3$, $CH_3O$, Br, Cl, F, I, $NO_2$ or $OCH_2CO_2C_2H_5$; $R_8$ is $C_1$-$C_6$ alkyl, phenyl or benzyl; $R_9$ is hydrogen, hydroxyl, $C_1$-$C_3$ alkyl, $C_1$-$C_3$ alkoxy or phenyl; $R_{10}$ and $R_{11}$ are hydrogen, $C_1$-$C_4$ alkyl or phenyl; X+ is inorganic or organic, when X is inorganic, it is alkali metals, alkaline earth metals, Co, Zn, or Ag;

when the cation X+ is organic, X+ is represented by formula IIIa $N^+R_aR_bR_cR_d$  (IIIa)

wherein $R_a$ is hydrogen, $C_1$-$C_{30}$ alkyl straight chain or branched [optionally mono- or disubstituted with HO—, $CH_3O_2C$—, $CH_3S$—, $C_3$-$C_{18}$alkenylaminoalkylene ($C_1$-$C_3$), $H_2N$, $(CH_3)_2N$—,

], $C_3$-$C_6$ alkenyl, $C_3$-$C_6$ alkynyl, $C_3$-$C_6$ cycloalkyl,

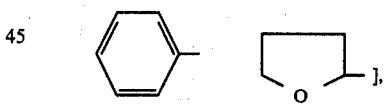

wherein $R_e$ and $R_f$ each may be H, $CH_3$ or n-$C_{16}H_{33}SO_2$—; $R_b$ is hydrogen, $C_1$-$C_{30}$ alkyl straight chain or branched [optionally mono- or disubstituted with HO— or

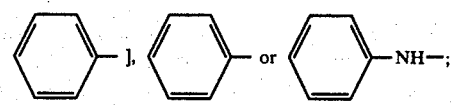;

$R_c$ is hydrogen, $C_1-C_{30}$ alkyl straight chain or branched [optionally mono- or disubstituted with HO— or

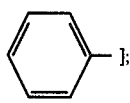];

$R_d$ is hydrogen, $C_1-C_{30}$ alkyl straight chain or branched [optionally substituted with HO—, Cl— or

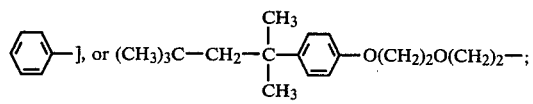

and when $R_a$ and $R_b$ are taken together with the nitrogen they are attached to they represent a moiety of

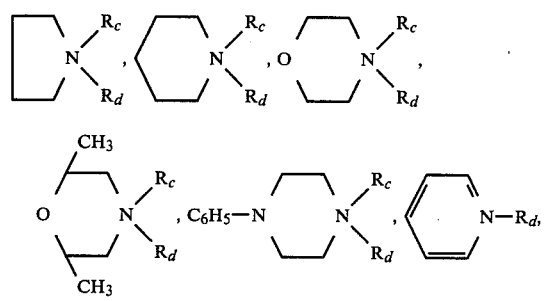

wherein $R_c$ and $R_d$ are defined as above;

organic cation $X^+$ may also be imidazolium, pyridinium, quinolinium, dithiolium, tetrazolium or be represented by formula IIIb

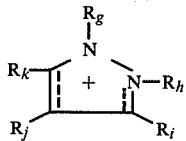 (IIIb)

wherein $R_g$ and $R_h$ each are $C_1-C_3$ alkyl; $R_j$ is hydrogen, halogen, $C_1-C_3$ alkyl or $C_1-C_3$ alkoxy; $R_i$ and $R_k$ each are hydrogen $C_1-C_6$ alkyl straight chain or branched, $C_3-C_6$ cycloalkyl,

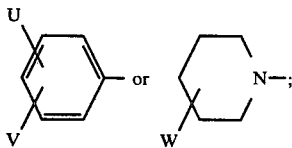

wherein U and V each are hydrogen, halogen, $C_1-C_3$ alkyl, $C_1-C_3$ alkoxy, CN or $CF_3$; W is hydrogen or $C_1-C_3$ alkyl; and each ⟶ symbol represents a single or double bond, wherein if both are single bonds then the cations are pyrazolidinium cations represented by formula IIIc

 (IIIc)

wherein $R_g$ to $R_k$ are as defined above; and
$X^+$ may also be represented by formulae IIIf and IIIg $R_1-P^+(Rm)_3$     IIIf wherein $R_1$ is $C_1-C_6$ alkyl,

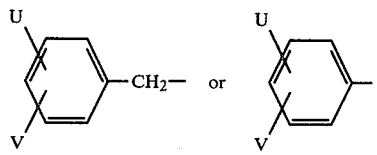

wherein U and V are as hereinabove defined; Rm is $C_1-C_6$ alkyl or

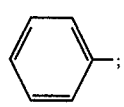;

$S^+R_aR_bR_c$(IIIg) and $I^+R_aR_b$(IIIh), wherein $R_a$, $R_b$ and $R_c$ are as hereinabove defined.

Still another group of novel salts represented by formula XI and of interest are graphically illustrated and described as follows:

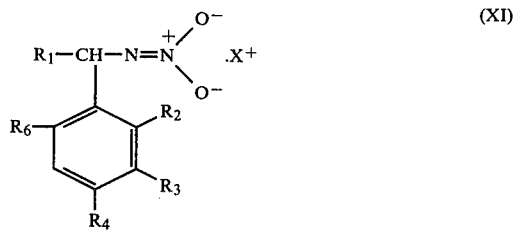 (XI)

wherein $R_1$ is hydrogen, $C_1-C_3$ alkyl, $C_1-C_3$ haloalkyl, CN, Br, Cl, F, I, $NO_2$, $SO_2R_8$, $COR_9$, phenyl or substituted phenyl and the substituents are $CH_3$, $CF_3$, $CH_3O$, $NO_2$ or $OCH_2CO_2C_2H_5$; $R_2$ and $R_6$ are hydrogen, Br, Cl, F, I, $C_1-C_4$ alkyl, $C_1-C_4$ haloalkyl, $C_1-C_4$ haloalkoxy, $SO_2R_8$, $SR_8$, $COR_{10}$; $R_3$ is hydrogen, $C_1-C_4$ alkyl, $C_1-C_4$ alkoxy, $NH_2$, $NHCOCH_3$, Br, Cl, F, I, $NO_2$, $SO_2R_8$, CN or $CO_2CH_3$; $R_4$ is hydrogen, Br, Cl, F, I, $C_1-C_2$ alkyl, $SO_2R_8$, $COR_9$, CN, $NHCOCH_3$, $SO_2NR_{10}R_{11}$,

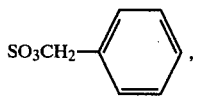, phenoxy or substituted phenoxy and the substituents are $CH_3$, $CF_3$, $CH_3O$, Br, Cl, F, I, $NO_2$ or $OCH_2CO_2C_2H_5$; $R_8$ is $C_1-C_6$ alkyl, phenyl or benzyl; $R_9$ is hydrogen, hydroxyl, $C_1$–$C_3$ alkyl, $C_1$–$C_3$ alkoxy or phenyl; $R_{10}$ and $R_{11}$ are hydrogen, $C_1$–$C_4$ alkyl or phenyl; $X^+$ is inorganic or organic, when X is inorganic, it is alkali metals, alkaline earth metals, Co, Zn, or Ag;

when the cation $X^+$ is organic, $X^+$ is represented by formula IIIa

   (IIIa)

wherein $R_a$ is hydrogen, $C_1$–$C_{30}$ alkyl straight chain or branched [optionally mono- or disubstituted with HO—, $CH_3O_2C$—, $CH_3S$—, $C_3$–$C_{18}$alkenylaminoalkylene ($C_1$–$C_3$), $H_2N$, $(CH_3)_2N$—,

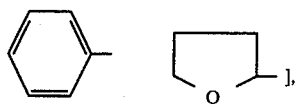

$C_3$–$C_6$ alkenyl, $C_3$–$C_6$ alkynyl, $C_3$–$C_6$ cycloalkyl,

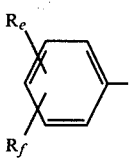

wherein $R_e$ and $R_f$ each may be H, $CH_3$ or n-$C_{16}H_{33}SO_2$—; $R_b$ is hydrogen, $C_1$–$C_{30}$ alkyl straight chain or branched [optionally mono- or disubstituted with HO— or

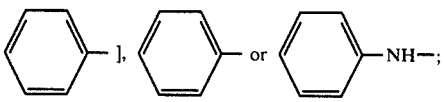

$R_c$ is hydrogen, $C_1$–$C_{30}$ alkyl straight chain or branched [optionally mono- or disubstituted with HO— or

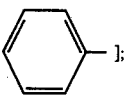

$R_d$ is hydrogen, $C_1$–$C_{30}$ alkyl straight chain or branched [optionally substituted with HO—, Cl— or

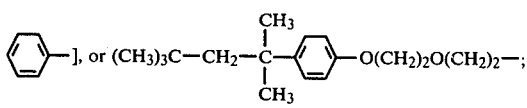

and when $R_a$ and $R_b$ are taken together with the nitrogen they are attached to they represent a moiety of

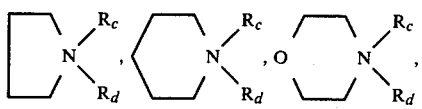

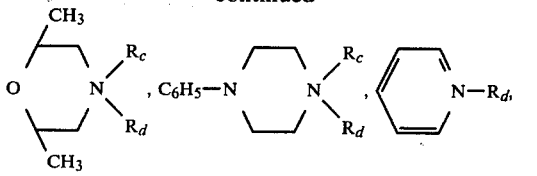

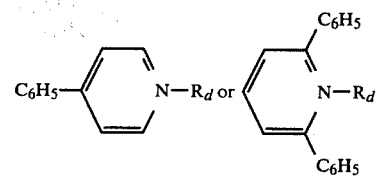

wherein $R_c$ and $R_d$ are defined as above;

organic cation $X^+$ may also be imidazolium, pyridinium, quinolinium, dithiolium, tetrazolium or be represented by formula IIIb

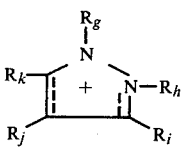   (IIIb)

wherein $R_g$ and $R_h$ each are $C_1$–$C_3$ alkyl; $R_j$ is hydrogen, halogen, $C_1$–$C_3$ alkyl or $C_1$–$C_3$ alkoxy; $R_i$ and $R_k$ each are hydrogen $C_1$–$C_6$ alkyl straight chain or branched, $C_3$–$C_6$ cycloalkyl,

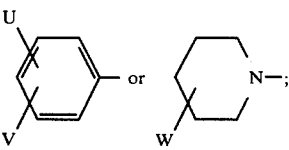

wherein U and V each are hydrogen, halogen, $C_1$–$C_3$ alkyl, $C_1$–$C_3$ alkoxy, CN or $CF_3$; W is hydrogen or $C_1$–$C_3$ alkyl; and each $=$ symbol represents a single or double bond, wherein if both are single bonds then the cations are pyrazolidinium cations represented by formula IIIc

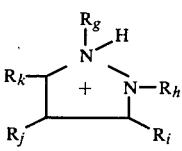   (IIIc)

wherein $R_g$ to $R_k$ are as defined above, and $X^+$ may also be represented by formulae IIIf and IIIg $R_1$-$P^+(Rm)_3$   IIIf wherein $R_1$ is $C_1$–$C_6$ alkyl,

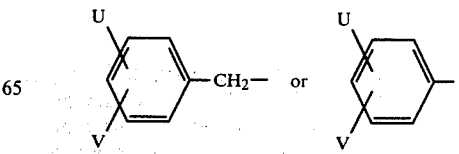

wherein U and V are as hereinabove defined; Rm is C₁–C₆ alkyl or

S⁺R_aR_bR_c(IIIa) and I⁺R_aR_b(IIIh), wherein R_a, R_b and R_c are as hereinabove defined.

The invention relates to methods for treating graminaceous crops, leguminous crops, cotton, sunflowers and herbaceous ornamental plants to increase axillary branching, improve the canopy and enhance flowering thereof. Surprisingly, application of the above-said salts to the foliage of the above-identified crops has the further advantage that said salts produce a dwarfing effect in said plants while increasing the stem stiffness thereof. They also enhance yield therefrom.

Dwarfing and/or stiffening of the stems of cotton, legumes, graminaceous crops and sunflowers is most advantageous to the farmer since lodging of these crops usually results in reduced yields of the affected crops.

Lodging, in the present application, refers to the deflection of the plant from the vertical, varying in degree from only a slight deflection to complete deflection (i.e. plants prone) caused by, in most cases, the action of wind and/or rain on the plants. This deflection is such that when the causal agent (wind, rain) is no longer present the deflection is neither immediately nor completely overcome. Moreover, where extensive or severe lodging has occurred, the crop may be difficult to harvest and the yield markedly reduced.

In practice we have found that application to the foliage of seedling plants of from about 0.06 to 2.0 kg/ha and preferably about 0.125 to 0.50 kg/ha is sufficient to achieve the several desirable and advantageous biological responses in plants described above.

Inasmuch as the salts or compounds of formula (I) of the present invention have only limited solubility in water, they are generally formulated for foliar application as wettable powders, flowable dispersions or emulsion concentrates, which are usually dispersed in water on in other, inexpensive, liquid diluents for application to the foliage of said plants as a liquid spray.

A typical wettable powder can be prepared by grinding together approximately 46% by weight of a finely divided carrier such as attapulgite, 50% by weight of the pyrazolium, pyrazolinium or pyrazolidine salt of 2,4,6-trisubstituted-N-nitroaniline, 3% by weight of the sodium salt of condensed naphthalene sulfonic acids and 1% by weight of sodium N-methyl-N-oleoyltaurate.

A typical flowable dispersion can be prepared by admixing about 42% by weight of the N-nitroaniline salt with about 3% by weight of the sodium salt of condensed naphthalene sulfonic acids, 2% by weight of finely divided bentonite and 53% by weight of water.

Emulsion concentrated may be prepared by dissolving 15% to 70% by weight of the formula (I) compound in 85% to 30% of a solvent such as N-methylpyrrolidone, lower alcohols, methylisobutylketone, 2-methoxy ethanol, propylene glycol, diethylene glycol, diethylene glycol monomethyl ether, formamide, methylformamide, and the like, and mixtures thereof. Advantageously, surfactants such as polyoxyethylated vegetable oil or an alkyl phenoxy polyoxyethylene ethanol are also incorporated in amounts of 1% to 5% by weight of said concentrate.

In accordance with this invention, the trisubstituted-N-nitroanilines (phenylnitramines) can be prepared from the corresponding substituted anilines by a variety of conventional procedures. For illustrative purposes, one such procedure is hereinbelow graphically illustrated and described as follows:

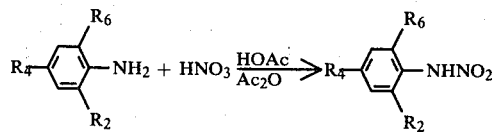

wherein R₂, R₄ and R₆ are as defined above. The above synthesis is conveniently carried out in a solvent, such as acetic acid, preferably in the presence of acetic anhydride. The product may be precipitated from the reaction mixture by the addition of ice water. Purification may be effected by conventional procedures such as recrystallization, chromatography, and the like.

The nitroanilines, wherein R₂ and/or R₆ are haloalkyl or hydroxyalkyl and R₄ is halogen, can be prepared by a two-step synthesis involving Step 1, the reaction of the appropriate haloalkyl aniline or haloalkoxyaniline with halogen (e.g. chlorine or bromine) in the presence of an acid acceptor such as sodium acetate, potassium acetate, or the like, in the presence of an inert organic solvent (e.g. tert-butanol, CCl₄, ethylene dichloride, chlorobenzene, or the like). The reaction is generally conducted at a temperature in the range of from 25° C. to 75° C., and preferably at a temperature of about 45° to 55° C. The reaction yields the corresponding 2,4,6-trisubstituted aniline, which may then be converted, in Step 2, to the corresponding 2,4,6-trisubstituted N-nitroaniline by reaction with nitric acid in the presence of a solvent, such as acetic acid, and acetic anhydride. Steps 1 and 2 can be graphically illustrated as follows:

Step 1

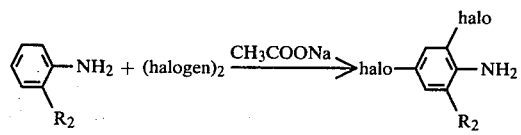

or

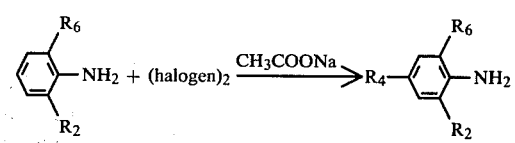

wherein R₂ and R₆ are haloalkyl or haloalkoxy, and R₄ is chlorine or bromine.

Step 2

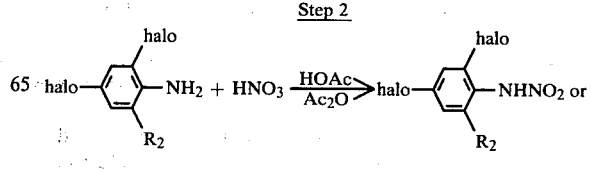

-continued

Step 2

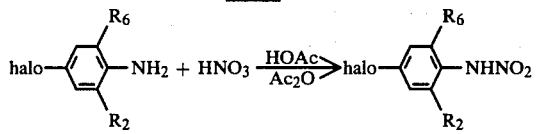

The formula (II) salts of the substituted -N-nitroaniline compounds can be conveniently prepared from the substituted nitroaniline compounds by one or more procedures, hereinafter referred to as Methods A,B,C,D or E.

Methods for the preparation of salts of 2,4,6-trisubstituted N-nitroanilines

Method A

The N-nitroaniline is dissolved in dilute aqueous sodium or potassium hydroxide and filtered. To this solution is added one molar equivalent of the appropriate salt and dissolved in water. In most cases the product separates as a solid, and is removed by filtration and purified by recrystallization. Whenever no precipitation occurs or the product separates as an oil, an extraction with methylene chloride is performed. Concentration of this extract yields the product which may be further purified by recrystallization.

Method B

A solution of the N-nitroaniline in anhydrous ether is treated with a solution of one equivalent of the appropriate nitrogen base in ether. The desired product is removed by filtration and purified by washing and recrystallization. Precipitation of the product may be promoted by the addition of petroleum ether.

Method C

To a methanolic suspension of the silver salt of the N-nitroaniline is added one equivalent of the halide salt of the appropriate amine dissolved in methanol. The mixture is stirred at 25° C. for one hour. The precipitated silver halide is removed by filtration, the product is recovered by evaporating the methanolic solution and purified by recrystallization.

Method D

An aqueous solution of the sodium salt of the N-nitroaniline is saturated with a large excess of the desired metal salt until solids remain undissolved. After stirring for one hour, the solids are removed by filtration and recrystallized or washed with a suitable solvent, and dried.

Method E

A methylene chloride solution of the free N-nitroaniline is treated with a three-fold excess of an aqueous solution of the appropriate metal hydroxide, acetate or carbonate. If precipitation occurs, the product is removed by filtration and recrystallized. Otherwise, the aqueous layer is separated and evaporated to dryness. The residue is treated with ethyl acetate and filtered. Removal of the ethyl acetate affords the product which may be recrystallized, if necessary.

Formula (I) compounds wherein $R_7$ is a substituent other than hydrogen may be conveniently prepared as follows:

The appropriately substituted formula (I) compound ($R_7$=hydrogen) is reacted in with an alcoholic solution of 1 equivalent of sodium hydroxide in the presence of a lower alcohol such as methanol, and the thus formed sodium salt is isolated by evaporating the reaction mixture to dryness. Next, the sodium salt is dissolved in dimethyl sulfoxide (DMSO) and treated with the appropriate alkyl halide at a temperature range from about 20° C. to about 30° C., preferably 25° C. for a period of time sufficient to essentially complete the reaction. The reaction mixture is then poured into water, the product extracted with a water immiscible solvent such as ether and recovered from said extract by standard laboratory procedures. The above reaction sequence may be graphically illustrated as follows:

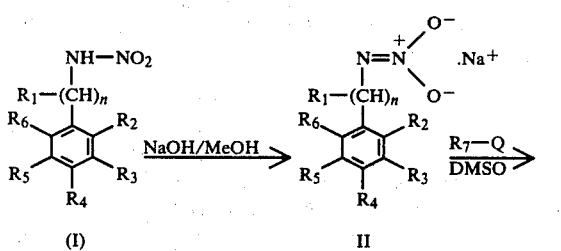

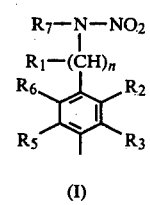

Wherein in the above reaction sequence Q is halogen, n, R, to $R_7$ are as hereinabove defined except that in the $R_7$-Q formula $R_7$ cannot be hydrogen.

Formula (Ia) phenylnitramines may be prepared by the following route:

A formula II silver salt is suspended in ether under an inert atmosphere such as $N_2$, and reacted with 1:1 equivalent of the appropriate $R_7$-Q compound at a temperature range of from about 20° C. to about 30° C. and preferably 25° C. for a period of time sufficient to essentially complete the reaction. The thus obtained O-alkyl derivative of formula (Ia) structure is isolated and purified by standard laboratory procedures. The above reaction sequence may be graphically illustrated as follows:

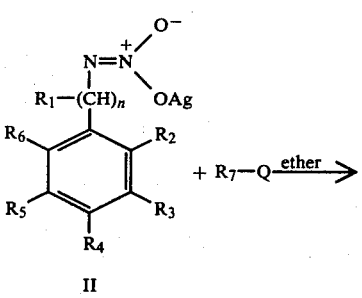

-continued

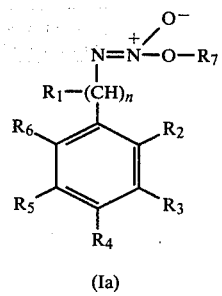

(Ia)

It is recognized of course, that in the course of the preparation of formula (I) compounds wherein $R_7$ is other than hydrogen formula (Ia) compounds are also formed, and vice versa.

Formula (I) compounds wherein n is 1 and $R_7$ is hydrogen may be conveniently prepared as follows:

A solution of the appropriate benzyl halide or mesylate and ammonium nitrourethane is heated in the presence of dry dimethyl sulfoxide at about 80° C. for about 4 hours or a period of time sufficient to essentially complete the reaction. The reaction mixture is then cooled down, poured in water extracted with a water immiscible organic solvent such as ether and the solution dried over anhydrous magnesium sulfate. Next, anhydrous ammonia gas is bubbled through the solution. The precipitated material is then isolated, dissolved in water and precipitated from the aqueous solution with a dilute acid. The thus obtained product is then isolated by standard laboratory methods and further purified, if so desired. The above reaction sequence may be graphically illustrated as follows:

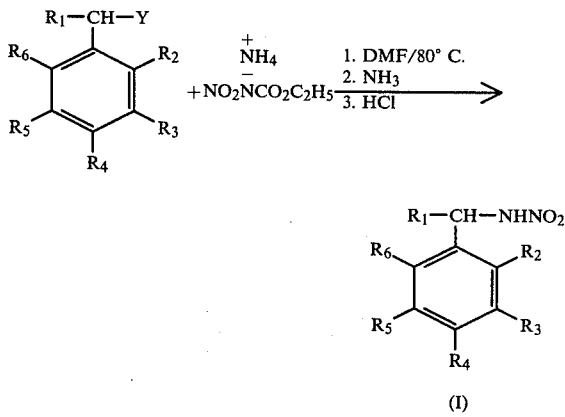

Wherein $R_1$ to $R_6$ are as hereinabove defined, Y is Br, Cl or $CH_3SO_3$.

The intermediate substituted anilines may also be N-nitrated to yield the corresponding N-nitroanilines as follows:

Diisopropylamine is lithiated with an equimolar amount of n-butyllithium in an inert solvent such as ether at about $-75°$ to $-80°$ C. Next a solution of the appropriately substituted aniline is added to the above mixture at about $-60°$ C., the reaction mixture warmed to about 0° C. and methyl nitrate added. The reaction mixture is allowed to warm slowly to room temperature and the product product isolated by standard laboratory procedures.

Surprisingly, it has also been found that the formula I compounds of this invention are effective for reducing the relative stem growth of broadleaf plants and for increasing the stem stiffness thereof, particularly for broadleaf agronomic crops such as sunflowers, when said compounds are applied preemergence to soil in which seeds of said plants have been sown. When used in this manner said formula I compounds are generally applied at rates of from 0.125 to 2.0 and preferably 0.25 to 0.75 kg/ha.

The invention is further illustrated by the Examples set forth below which are not intended to be limiting on the invention.

EXAMPLE 1

Methods for the preparation of salts of 2,4,6-trisubstituted N-nitroanilines

Method A

The N-nitroaniline is dissolved in dilute aqueous sodium or potassium hydroxide and filtered. To this solution is added one molar equivalent of the appropriate salt and dissolved in water. In most cases the product separates as a solid, and is removed by filtration and purified by recrystallization. Whenever no precipitation occurs or the product separates as an oil, an extraction with methylene chloride is performed. Concentration of this extract yields the product which may be further purified by recrystallization.

Method B

A solution of the N-nitroaniline in anhydrous ether is treated with a solution of one equivalent of the appropriate nitrogen base in ether. The desired product is removed by filtration and purified by washing and recrystallization. Precipitation of the product may be promoted by the addition of petroleum ether.

Method C

To a methanolic suspension of the silver salt of the N-nitroaniline is added one equivalent of the halide salt of the appropriate amine dissolved in methanol. The mixture is stirred at 25° C. for one hour. The precipitated silver halide is removed by filtration, the product recovered by evaporating the methanolic solution and purified by recrystallization.

Method D

An aqueous solution of the sodium salt of the N-nitroaniline is saturated with a large excess of the desired metal salt until solids remain undissolved. After stirring for one hour, the solids are removed by filtration and recrystallized or washed with a suitable solvent, and dried.

Method E

A methylene chloride solution of the free N-nitroaniline is treated with a three-fold excess of an aqueous solution of the appropriate metal hydroxide, acetate or carbonate. If precipitation occurs, the product is removed by filtration and recrystallized. Otherwise, the aqueous layer is separated and evaporated to dryness. The residue is treated with ethyl acetate and filtered. Removal of the ethyl acetate affords the product which may be recrystallized, if necessary.

By the above methods a number of compounds are prepared, these are listed in Tables appended hereto.

TABLE I

Inorganic salts of 2,4,6-tribromo-N—aci-nitroaniline and other 2,4,6-trisubstituted N—aci-nitroanilines

| No | X+ | Analysis Calculated | Found | M.P. (°C.) | Method |
|---|---|---|---|---|---|
| 1 | Na+ | C 16.64<br>H 1.40<br>N 6.47 | C 16.74<br>H 1.31<br>N 6.40 | 260 (dec) | E |
| 2 | K+ | C 16.72<br>H 0.94<br>N 6.50 | C 17.19<br>H 0.74<br>N 6.26 | >230 | E |
| 3 | Li+ | H 1.61<br>N 7.03<br>Br 60.12<br>Li 1.74 | H 1.46<br>N 6.90<br>Br 60.43<br>Li 1.59 | 284–288 (dec) | E |
| 4 | Ca2+ | C 16.78<br>H 1.40<br>N 6.52<br>Br 55.82 | C 16.29<br>H 1.08<br>N 6.34<br>Br 56.03 | 240 (dec) | D |
| 5 | Mg2+ | C 16.37<br>H 1.83<br>N 6.37<br>Mg 2.76 | C 16.62<br>H 2.45<br>N 5.71<br>Mg 3.27 | 129–135 (dec) | E |
| 6 | Ba2+ | C 15.65<br>H 0.88<br>N 6.08<br>Ba 14.91 | C 15.37<br>H 0.86<br>N 6.07<br>Ba 14.96 | 202–208 | D |
| 7 | Sr2+ | | | 216–219 (dec) | D |

| No | M+ | Analysis Calculated | Found | M.P. (°C.) | Method |
|---|---|---|---|---|---|
| 8 | Co2+ | N 6.65<br>Co 6.99 | N 6.36<br>Co 6.79 | 172–176 (dec) | C |
| 9 | Zn2+ | C 17.73 | C 18.16 | 110–130 | D |
| 10 | Ag+ | | | 176–190 (dec) | D |

TABLE Ia

Inorganic salts of 2,4,6 trisubstituted formual (II) compounds of structure

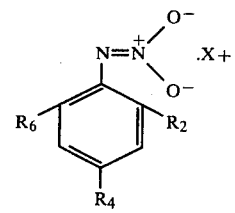

| No | R2 | R4 | R6 | X+ | Analysis Calculated | Found | M.P. (°C.) | Method |
|---|---|---|---|---|---|---|---|---|
| 1 | CO2C2H5 | Br | Br | K+ | C 25.72<br>H 2.13<br>N 6.60 | C 25.32<br>H 2.02<br>N 6.40 | 232–234 (dec) | E |
| 2 | Br | Br | I | Na+ | | | | |
| 3 | Cl | I | Cl | Na+ | | | | |
| 4 | CF3 | Br | Br | Na+ | C 20.81<br>H 1.00<br>N 6.94<br>Br 39.56<br>F 14.40<br>Na 5.70 | C 21.05<br>N 67.48<br>Br 39.47<br>F 14.13<br>Na 5.87 | 223–226 (dec) | E |
| 5 | CH3 | CH3 | CH3 | Na+ | | | | |
| 6 | Cl | Cl | Cl | Na+ | | | | |
| 7 | Cl | Cl | Br | Na+ | | | | |
| 8 | Br | CN | Br | Na+ | | | >250 | E |
| 9 | Br | CH3 | Br | Na+ | | | >230 | E |

TABLE Ib

Sodium salts of formula II compounds of structure

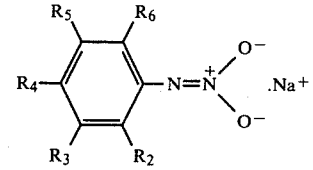

| No. | R2 | R3 | R4 | R5 | R6 | mp °C. |
|---|---|---|---|---|---|---|
| 1 | Br | Br | | Br | Br | 200 (dec) |
| 2 | Br | | | | C2H5 | >250 |
| 3 | CH3 | | Br | | CH3 | 190–200 (dec) |
| 4 | Br | | CH3 | | Br | >260 |
| 5 | CH3 | | | | CH3 | gum |
| 6 | C2H5 | | | | C2H5 | gum |
| 7 | Br | | | | | 74–75 |
| 8 | Br | | | | Br | >200 |
| 9 | Cl | Cl | | | | 260 (dec) |
| 10 | Br | | Br | | C2H5 | 250 (dec) |
| 11 | Br | | C2H5 | | Br | 252 (dec) |
| 12 | Cl | | I | | Cl | >250 |
| 13 | | | CH3SO2 | | | >300 |
| 14 | | | COC6H5 | | | 254–255 |
| 15 | COC6H5 | | | | | 89–91 |

TABLE Ic

Primary amine salts of 2,4,6-tribromo-N—aci-nitroaniline

| No | X+ | Analysis Calculated | Found | M.P. (°C.) | Method |
|---|---|---|---|---|---|
| 1 | NH4+ | C 18.39<br>H 1.54 | C 18.43<br>H 1.54 | 164 | B |

TABLE Ic-continued

| | Primary amine salts of 2,4,6-tribromo-N—aci-nitroaniline | | | | |
|---|---|---|---|---|---|
| | | Analysis | | M.P. | |
| No | X+ | Calculated | Found | (°C.) | Method |
| 2 | $CH_3NH_3^+$ | N 10.72<br>C 20.71<br>H 1.99<br>N 10.35<br>Br 59.07 | N 10.72<br>C 20.80<br>H 1.97<br>N 10.35<br>Br 59.07 | 157–164 | B |
| 3 | $C_2H_5NH_3^+$ | | | 140–141 (dec) | B |
| 4 | $n\text{-}C_3H_7NH_3^+$ | | | 153 (dec) | B |
| 5 | $i\text{-}C_3H_7NH_3^+$ | | | | |
| 6 | $n\text{-}C_4H_9NH_3^+$ | | | | |
| 7 | $sec\text{-}C_4H_9NH_3^+$ | | | 137–138 (dec) | B |
| 8 | $i\text{-}C_4H_9NH_3^+$ | | | | |
| 9 | $t\text{-}C_4H_9NH_3$ | | | 178–180<br>(slow dec) | |
| 10 | $n\text{-}C_5H_{11}NH_3^+$ | | | 131–132 | |
| 11 | $n\text{-}C_6H_{13}NH_3^+$ | | | | |
| 12 | $n\text{-}C_8H_{17}NH_3^+$ | C 33.36<br>H 4.40<br>N 8.34<br>Br 47.56 | C 33.58<br>H 4.58<br>N 8.34<br>Br 47.52 | 78–81 | B |
| 13 | $n\text{-}C_{12}H_{25}NH_3^+$ | C 38.59<br>H 5.40<br>N 7.50<br>Br 42.30 | C 38.80<br>H 5.40<br>N 7.35<br>Br 42.20 | 91–92 | B |
| 14 | $n\text{-}C_{14}H_{29}NH_3^+$ | | | | |
| 15 | $n\text{-}C_{16}H_{33}NH_3^+$ | | | | |
| 16 | $n\text{-}C_{18}H_{35}NH_3^+$ | C 44.73<br>H 6.57<br>N 6.52<br>Br 37.21 | C 45.08<br>H 6.65<br>N 6.71<br>Br 37.57 | 75–77 | B |
| 17 | $n\text{-}C_{18}H_{37}NH_3^+$ | | | 76–77 | B |
| 18 | $n\text{-}C_{20}H_{42}NH_3^+$ | | | 79–80 | B |
| 19 | $n\text{-}C_{22}H_{45}NH_3^+$ | | | 74–76 | B |
| 20 | $n\text{-}C_{30}H_{62}NH_3^+$ | | | | |
| 21 | $H_2C=CH-CH_2NH_3^+$ | | | 145–146 | A |
| 22 | $HC\equiv C-CH_2-NH_3^+$ | | | 136–138 (dec) | B |
| 23 | $HOCH_2CH_2NH_3^+$ | C 22.04<br>H 2.31<br>N 9.57<br>Br 55.00 | C 22.08<br>H 2.38<br>N 9.64<br>Br 55.05 | 168–169 | B |
| 24 | $(CH_3)_2CH_2CH_2CHNH_3^+$<br>$\quad\quad\quad\quad\vert$<br>L— $\quad$ $CO_2CH_3$ | C 30.02<br>H 3.49<br>N 8.08<br>Br 46.10 | C 30.26<br>H 3.52<br>N 7.99<br>Br 46.21 | 129–131 | B |
| 25 | $CH_3S(CH_2)_3NH_3^+$ | | | 102–103 (dec) | |
| 26 | $C_8H_{17}CH=CH-C_8H_{16}-NHC_3H_6NH_3^+$ | N 6.77 | N 6.73 | 90–96 | B |
| 27 | $C_8H_{17}CH=CH-CH_2-CH=CH-C_5H_{10}NH_3^+$ | H 5.98<br>N 6.56 | H 6.44<br>N 6.37 | Wax | B |
| 28 | $C_8H_{17}CH=CH-C_8H_{16}NH_3^+$ | | | 74 | A |
| 29 |  | | | 170–175<br>(dec) | B |
| 30 |  | | | | |
| 31 |  | C 30.80<br>H 2.15<br>N 8.98 | C 30.72<br>H 2.07<br>N 8.83 | 78–85 | B |
| 32 | 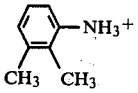 | | | 86–87 | B |
| 33 | 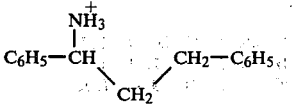 | | | | |

TABLE Ic-continued

Primary amine salts of 2,4,6-tribromo-N—aci-nitroaniline

| No | X+ | Analysis Calculated | Analysis Found | M.P. (°C.) | Method |
|---|---|---|---|---|---|
| 34 | C₆H₅—CH(NH₃⁺)—CH₂—CH(NH₂)—CH₂—C₆H₅ | | | | |
| 35 | C₆H₅—CH(NH₃⁺)—CH₂—C₆H₅ | | | | |
| 36 | C₆H₅—CH(NH₃⁺)—CH=CH—C₆H₅ | | | | |
| 37 | 4-(n-C₁₆H₃₃SO₂)C₆H₄NH₃⁺ | | | | |
| 38 | (tetrahydrofuran-2-yl)—CH₂—NH₃⁺ | | | 154–155 | B |
| 39 | (CH₃)₂N—NH₃⁺ | | | | |

TABLE Id

Tallowamine salts of miscellaneous N—aci-nitroanilines of

[structure: substituted phenyl with R2, R3, R4, R5, R6 substituents, N=N⁺(O⁻)(O⁻)·C₁₂H₃₅NH₃⁺]

| No | R₂ | R₃ | R₄ | R₅ | R₆ | Analysis Calculated | Analysis Found | M.P. °C. |
|---|---|---|---|---|---|---|---|---|
| 1 | Br | | | | C₂H₅ | C 60.93 H 9.05 N 8.20 | C 60.72 H 9.60 N 8.35 | gum |
| 2 | CH₃ | | Br | | CH₃ | C 60.90 H 9.04 N 8.25 Br 15.58 | C 60.90 H 9.25 N 8.29 Br 15.52 | gum |
| 3 | C₂H₅ | | | | CH(CHC₂H₅) | C 73.57 H 11.32 N 8.58 | C 73.01 H 11.83 N 8.77 | gum |
| 4 | Br | Br | Br | | Br | | | 110–112 |
| 5 | CH₃ | | | | CH₃ | C 71.67 H 11.34 N 9.65 | C 71.58 H 11.61 N 9.64 | gum |
| 6 | C₂H₅ | | | | C₂H₅ | C 72.52 H 11.52 N 9.06 | C 72.20 H 11.61 N 9.02 | gum |
| 7 | Br | | | | Br | H 7.68 N 7.43 | H 7.29 N 7.43 | wax |
| 8 | C₂H₅ | | | | CH(CH₃)₂ | C 73.21 N 8.83 | C 73.22 N 8.48 | gum |
| 9 | CH₃ | | | | CH(CH₃)₂ | C 73.21 N 8.83 | C 73.22 N 8.48 | gum |
| 10 | CH₃ | | | | C(CH₃)₃ | H 11.23 N 8.33 | H 11.53 N 9.07 | gum |
| 11 | Cl | I | Cl | | | | | 70–72 |
| 12 | Br | | Br | | | | | 25–30 |

TABLE Ie

Secondary amine salts of 2,4,6-tribromo-N—aci-nitroaniline

| No | X+ | Analysis Calculated | Analysis Found | M.P. (°C.) | Method |
|---|---|---|---|---|---|
| 1 | (CH₃)₂NH₂⁺ | | | 164.5–165.5 (dec) | |
| 2 | (C₂H₅)₂NH₂⁺ | | | 156–160 | B |
| 3 | (n-C₃H₇)₂NH₂⁺ | | | | |
| 4 | [(CH₃)₂CH]₂NH₂⁺ | C 30.28 H 3.81 N 8.83 | C 30.63 H 3.94 N 8.75 | 164–171 | B |
| 5 | (n-C₄H₉)₂NH₂⁺ | | | 166–169 (dec) | B |
| 6 | (C₁₈H₃₇)₂NH₂⁺ | | | | |
| 7 | (HOCH₂CH₂)₂NH₂⁺ | | | 158–159 (dec) | B |
| 8 | (C₆H₅—CH₂)₂NH₂⁺ | C 41.98 H 3.17 N 7.34 Br 41.91 | C 41.27 H 3.24 N 7.28 Br 42.16 | 168–169 (dec) | B |
| 9 | C₆H₅—NH₂⁺(CH₃) | | | | |
| 10 | C₆H₅—NH₂⁺(C₄H₉—t) | | | 155–158 | B |
| 11 | cyclohexyl-NH₂⁺ | | | 161–163 (dec) | B |
| 12 | morpholinyl-NH₂⁺ | C 26.60 H 2.62 N 9.10 | C 26.10 H 2.62 N 9.04 | 157–158 (dec) | |

TABLE Ie-continued

Secondary amine salts of 2,4,6-tribromo-N—aci-nitroaniline

| No | X+ | Analysis Calculated | Found | M.P. (°C.) | Method |
|---|---|---|---|---|---|
| 13 | 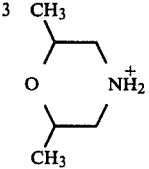 | | | 156–158 (dec) | B |

TABLE If

Secondary amine salts of various di-and trisubstituted N—aci-nitroanilines

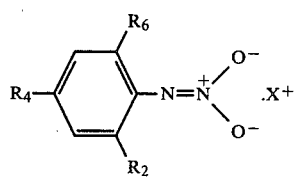

| No | R$_2$ | R$_4$ | R$_6$ | X+ | Analysis Calculated | Found | M.P. (°C.) | Method |
|---|---|---|---|---|---|---|---|---|
| 1 | Br | F | F | [(CH$_3$)$_2$CH]$_2$NH$_2$ | C 40.92<br>H 4.58<br>N 11.93<br>Br 27.69<br>F 10.79 | C 40.66<br>H 5.12<br>N 11.84<br>Br 27.43<br>F 10.66 | 156–162 | B |
| 2 | Br | Br | i-Pr | [(CH$_3$)$_2$CH]$_2$NH$_2$ | C 41.11<br>H 5.52<br>N 9.59 | C 40.98<br>H 5.56<br>N 9.56 | 144–157 | B |
| 3 | F | F | F | [(CH$_3$)$_2$CH]$_2$NH$_2$ | C 49.14<br>H 6.19<br>N 14.33<br>F 19.14 | C 49.35<br>H 6.26<br>N 14.27<br>F 19.29 | 148–161 | B |
| 4 | Br | i-Pr | Br | [(CH$_3$)$_2$CH]$_2$NH$_2$ | C 41.02<br>H 5.74<br>N 9.57<br>Br 36.39 | C 41.06<br>H 5.42<br>N 9.62<br>Br 36.66 | 168–175 | B |
| 5 | Br | Br | OCH$_3$ | [(CH$_3$)$_2$CH]$_2$NH$_2$ | C 36.55<br>H 4.96<br>N 9.84 | C 37.11<br>H 5.51<br>N 10.15 | 139–145 | B |
| 6 | Br | Br | SO$_2$CHF$_2$ | [(CH$_3$)$_2$CH]$_2$NH$_2$ | N 3.75<br>F 7.43 | N 3.54<br>F 7.38 | 162–164 | B |
| 7 | Br | OCH$_3$ | Br | [(CH$_3$)$_2$CH]$_2$NH$_2$ | C 36.55<br>H 4.96<br>N 9.84<br>Br 37.42 | C 37.06<br>H 5.03<br>N 9.68<br>Br 36.24 | 148–150 | B |
| 8 | I | I | Cl | [(CH$_3$)$_2$CH]$_2$NH$_2$ | C 27.42<br>H 3.45<br>N 8.0<br>Cl 7.43 | C 27.53<br>H 3.52<br>N 7.91<br>Cl 7.38 | 182–183 | B |
| 9 | Br | Br | SO$_2$F | [(CH$_3$)$_2$CH]$_2$NH$_2$ | | | 118 | B |
| 10 | Br | H | Br | (HOCH$_2$CH$_2$)$_2$NH$_2^+$ | | | 115–118 | |

TABLE Ig

Tertiary amine salts with 2,4,6-tribromo-N—aci-nitroaniline

| No | X+ | Analysis Calculated | Found | M.P. (°C.) | Method |
|---|---|---|---|---|---|
| 1 | (CH$_3$)$_3$NH$^+$ | | | 138–140 dec >160 | |
| 2 | (C$_2$H$_5$)$_3$NH$^+$ | C 30.28<br>H 3.81<br>N 8.83 | C 30.33<br>H 3.82<br>N 8.81 | 128–135 (dec) | B |
| 3 | (n-C$_3$H$_7$)$_3$NH$^+$ | | | | B |
| 4 | (HOC$_2$H$_4$)$_3$NH$^+$ | C 27.50 | C 28.39 | 79–81 | B |

TABLE Ig-continued

Tertiary amine salts with 2,4,6-tribromo-N—aci-nitroaniline

| No | X+ | Analysis Calculated | Found | M.P. (°C.) | Method |
|---|---|---|---|---|---|
| | | H 3.46<br>N 8.02 | H 3.85<br>N 7.86 | | |
| 5 | 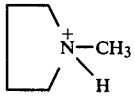 | | | 107–110 | B |
| 6 | 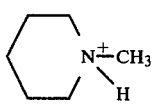 | | | 150–155 | B |
| 7 | 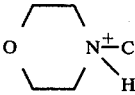 | | | 127–134 | B |
| 8 | 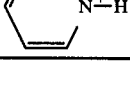 | | | 105–108 | B |

TABLE Ih

Quaternary amine salts of 2,4,6-tribromo-N—aci-nitroaniline

| No | X+ | Analysis Calculated | Analysis Found | M.P. (°C.) | Method |
|---|---|---|---|---|---|
| 1 | (CH₃)₄N⁺ | C 26.28<br>H 3.31<br>N 9.19 | C 26.47<br>H 3.19<br>N 9.40 | 212–214 (dec) | A |
| 2 | (C₂H₅)₄N⁺ | C 33.35<br>H 4.40<br>N 8.34 | C 33.51<br>H 4.31<br>N 8.50 | 126–129 (dec) | A |
| 3 | (n-C₃H₇)₄N⁺ | | | | |
| 4 | (n-C₄H₉)₄N⁺ | C 42.87<br>H 6.21<br>N 6.82 | C 42.83<br>H 6.38<br>N 6.67 | 102–106 | |
| 5 | (n-C₁₀H₂₃)₃N⁺CH₃ | | | oil | A |
| 6 | n-C₁₆H₃₃—N⁺(CH₃)₃ | | | | |
| 7 | ClCH₂CH₂N⁺(CH₃)₃ | C 26.60<br>H 3.05<br>N 8.46<br>Br 48.30 | C 27.05<br>H 3.05<br>N 8.34<br>Br 47.70 | 124–125 | C |
| 8 | HO—CH₂CH₂N⁺(CH₃)₃ | | | 177 (dec) | C |
| 9 | N-methyl-N-methyl piperidinium | C 31.99<br>H 3.72<br>N 8.61<br>Br 49.10 | C 32.06<br>H 3.75<br>N 8.57<br>Br 50.58 | 160–161 | C |
| 10 | N,N-dimethyl morpholinium | | | 193–194 (dec) | C |
| 11 | C₆H₅CH₂—N⁺(C₂H₅)₃ | C 40.31<br>H 4.27<br>N 7.42<br>Br 42.35 | C 40.44<br>H 4.27<br>N 7.43<br>Br 42.67 | 102–104 | A |
| 12 | N-cetylpyridinium (N⁺—C₁₆H₃₃-n) | C 47.80<br>H 5.94<br>N 6.19 | C 47.52<br>H 5.47<br>N 6.14 | 99–100 | A |
| 13 | 4-phenyl-N-methylpyridinium | | | 196–198 | A |
| 14 | 2,6-diphenyl-N-methylpyridinium | | | 150–151 | |
| 15 | C₆H₅—N(piperazine)⁺N(CH₃)₂ | | | 183–184 (dec) | C |
| 16 | (CH₃)₃CCH₂C(CH₃)₂—C₆H₄—O(CH₂)₂O—(CH₂)₂N⁺(CH₃)₂—CH₂C₆H₅ | H 5.64<br>N 5.34<br>Br 30.48 | H 5.62<br>N 5.39<br>Br 31.06 | 110–112 | A |

TABLE Ii

Miscellaneous salts of 2,4,6-tribromo-N—aci-nitroaniline

| No | X⁺ | M.P. °C. | Method |
|---|---|---|---|
| 1 | (C₆H₅)₃S⁺ | 142–149 (dec) | C |

TABLE Ii-continued
Miscellaneous salts of 2,4,6-tribromo-N—aci-nitroaniline

| No | X+ | M.P. °C. | Method |
|---|---|---|---|
| 2 | 1,3-dimethyl-2,4-diphenyl-imidazolium (CH₃—N, N—CH₃, C₆H₅, C₆H₅ with + on ring) | 165–166 (dec) | A |
| 3 | 1-methyl-2,6-diphenyl-pyridinium (C₆H₅, C₆H₅, N-CH₃, +) | 150–151 | A |
| 4 | 2,5-diphenyl-1,3-dithiolium (C₆H₅, S, S, C₆H₅) | 154–159 | A |
| 5 | 1-methoxy-4-phenyl-pyridinium (phenyl-pyridinium-N—OCH₃, +) | 118–121 | A |
| 6 | 1,1,4,4-tetramethyl-piperazinium (CH₃—N+, +N, CH₃, CH₃, CH₃) | 180–184 | C |
| 7 | C₈H₁₇CH=CH—C₈H₁₆—N⁺H(CH₃)(CH₃) | 40–45 | B |
| 8 | ⁺NH₃OH | | A |
| 9 | n-C₁₂H₂₅N⁺H(CH₃)₂ | 82 | A |
| 10 | (CH₃)₃N⁺—CH₂CH(OH)CH₂COOH | 141–151 (dec) | C |
| 11 | proline t-butyl ester (N⁺H₂, COOC(CH₃)₃) | 48–53 (hygroscopic) | B |
| 12 | (cyclohexyl)₂N⁺H₂ | 189–192 (dec) | B |
| 13 | (phenyl)₂I⁺ | 160 (dec) | B |
| 14 | benzamidinium (C₆H₅—C(=NH)—N⁺H₃) | 194–195 (dec) | A |
| 15 | (CH₃OCH₂CH₂)₂N⁺H₂ | 77–80 | B |
| 16 | (CH₃)₃N⁺(CH₂)₃N(CH₃)₂ | 113 | C |
| 17 | NH₂N⁺H₂CH₃ | 110–112 | B |
| 18 | NH₂N⁺H₃ | 131–132 | B |
| 19 | cyclopentyl-N⁺H₃ | 160–162 (dec) | B |
| 20 | cyclopropyl-N⁺H₃ | 138–140 (dec) | B |
| 21 | 1-methyl-4-oxopiperidinium (O=...N⁺H—CH₃) | 80 (dec) | B |
| 22 | C₆H₅—CH₂—CH(CO₂CH₃)—N⁺H₃ | 80–84 | B |
| 23 | 1,3-dimethyl-2,4-diphenyl-4,5-dihydro-imidazolium (CH₃, CH₃, N, C₆H₅, +, N, C₆H₅) | 145 | A |
| 24 | (C₆H₅)₃P⁺—CH₃ | 150–152 | A |
| 25 | (2,4-dichlorobenzyl)-P⁺(C₄H₉)₃ | 124–126 | A |
| 26 | H₂N(CH₂)₃N⁺H₃ | | |
| 27 | H₂N(CH₂)₂N⁺H₃ | | |
| 28 | n-C₁₈H₃₇N⁺(CH₃)₃ | | |
| 29 | piperidine-N-C(=O)-O-(2,5-dimethyl-4-isopropyl-phenyl)-N⁺(CH₃)₃ | | |

TABLE Ij
Salts of Formula:

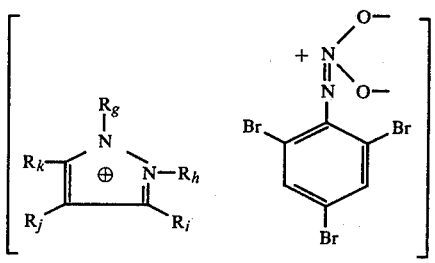

| No | $R_g$ | $R_h$ | $R_i$ | $R_j$ | $R_k$ | Analysis Calculated | Found | M.P. (°C.) |
|---|---|---|---|---|---|---|---|---|
| 1 | $CH_3$ | $CH_3$ | $C_6H_5$ | H | $C_6H_5$ | C 44.33<br>H 3.07<br>N 8.99<br>Br 38.47 | C 44.65<br>H 3.21<br>N 8.80<br>Br 38.44 | 145–146 (dec) |
| 2 | $CH_3$ | $CH_3$ | $C_6H_5$ | $OCH_3$ | $C_6H_5$ | C 44.13<br>H 3.24<br>N 8.58 | C 44.11<br>H 3.45<br>N 8.42 | 41–44 |
| 3 | $CH_3$ | $CH_3$ | 4-F—$C_6H_4$— | H | $C_6H_5$ | C 41.91<br>H 3.06<br>N 8.50<br>Br 36.37<br>F 2.88 | C 42.02<br>H 3.12<br>N 8.52<br>Br 36.41<br>F 2.93 | 91–92 |
| 4 | $CH_3$ | $CH_3$ | 3-methylpiperidin-1-yl | H | $C_6H_5$ | C 42.88<br>H 4.07<br>N 10.87<br>Br 37.21 | C 43.12<br>H 4.11<br>N 10.91<br>Br 36.89 | 122–124 |
| 5 | $CH_3$ | $CH_3$ | cyclohexyl | H | $C_6H_5$ | C 43.90<br>H 4.01<br>N 8.09<br>Br 38.10 | C 43.94<br>H 4.14<br>N 8.84<br>Br 37.96 | 153–154 |
| 6 | $CH_3$ | $CH_3$ | $C_6H_5$ | $CH_3$ | $C_6H_5$ | C 45.24<br>H 3.32<br>N 8.79 | C 45.48<br>H 3.41<br>N 8.93 | 146–148 |
| 7 | $C_2H_5$ | $CH_3$ | $C_6H_5$ | H | $C_6H_5$ | | | 139–140 (dec) |
| 8 | $CH_3$ | $CH_3$ | p-Cl—$C_6H_4$— | H | $C_6H_5$ | | | |
| 9 | $CH_3$ | $CH_3$ | 2,3-dimethylphenyl | H | $C_6H_5$ | | | |
| 10 | $CH_3$ | $CH_3$ | 3,5-dimethylphenyl | H | $C_6H_5$ | | | |
| 11 | $CH_3$ | $CH_3$ | 4-methylphenyl | H | $C_6H_5$ | | | |
| 12 | $CH_3$ | $CH_3$ | 2-methoxyphenyl | H | $C_6H_5$ | | | |
| 13 | $CH_3$ | $CH_3$ | 3-methoxyphenyl | H | $C_6H_5$ | | | |
| 14 | $CH_3$ | $CH_3$ | 4-methoxyphenyl | H | $C_6H_5$ | | | |

TABLE Ij-continued

Salts of Formula:

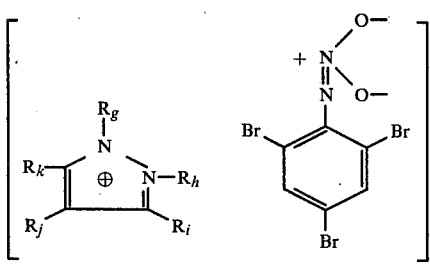

| No | $R_g$ | $R_h$ | $R_i$ | $R_j$ | $R_k$ | Analysis Calculated | Found | M.P. (°C.) |
|---|---|---|---|---|---|---|---|---|
| 15 | $CH_3$ | $CH_3$ | $C_6H_5$ | F | $C_6H_5$ | | | |
| 16 | $CH_3$ | $CH_3$ | $C_6H_5$ | Cl | $C_6H_5$ | | | |
| 17 | $CH_3$ | $CH_3$ | $C_6H_5$ | Br | $C_6H_5$ | | | |
| 18 | $CH_3$ | $CH_3$ | cyclohexyl | H | cyclohexyl | | | |
| 19 | $CH_3$ | $CH_3$ | piperidino | H | $C_6H_5$ | | | |
| 20 | $CH_3$ | $CH_3$ | H | H | H | | | |
| 21 | $CH_3$ | $CH_3$ | $CH_3$ | $CH_3$ | $CH_3$ | | | |
| 22 | $CH_3$ | $CH_3$ | Cl | H | $C_6H_5$ | | | |
| 23 | $CH_3$ | $CH_3$ | Br | Br | Br | | | |

TABLE Ik

Pyraislium salts of formula

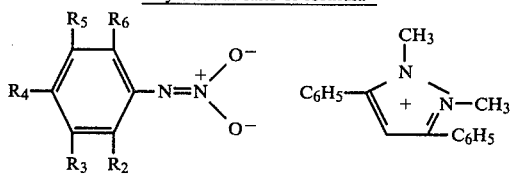

| No | $R_2$ | $R_3$ | $R_4$ | $R_5$ | $R_6$ | Analysis Calculated | Found | M.P. °C. | Method |
|---|---|---|---|---|---|---|---|---|---|
| 1 | Br | | Br | | $SO_2C_6H_5$ | | | 63–75 (dec) | |
| 2 | Cl | Cl | | | | | | 122–123 | |
| 3 | $C_2H_5$ | | | | $CH(CH_3)_2$ | C 72.23 H 7.14 N 12.03 | C 72.03 H 7.41 N 11.61 | hygroscopic gum | A |
| 4 | $CH_3$ | | | | $CH(CH_3)_2$ | C 69.06 H 7.08 N 11.93 | C 69.37 H 7.09 N 11.67 | hygroscopic gum | A |
| 5 | $CH_3$ | | | | $C(CH_3)_3$ | C 69.54 H 7.29 N 11.58 | C 69.58 H 6.81 N 11.74 | hygroscopic gum | A |
| 6 | Cl | | I | | Cl | | | 128–131 (dec) | A |
| 7 | Br | $CH_3$ | Br | | Br | | | 180–182 (dec) | A |
| 8 | Br | | $OCF_3$ | | Br | | | gum | |
| 9 | Br | | $SO_2C_6H_5$ | | Br | | | 110–115 | |
| 10 | Br | | $COCH_3$ | | Br | | | 143–144 | A |
| 11 | Br | | Br | | $COCH_3$ | | | 129–129.5 | |
| 12 | Br | Cl | $CH_3$ | | Br | | | 143–144 | |
| 13 | Br | | Br | Cl | Br | | | 175–176 | |
| 14 | I | | $CH_3$ | | $CH_3$ | | | 142.5–144 | |
| 15 | Br | $CH_3$ | $CH_3$ | | Br | | | 156–157 | |

TABLE Ik-continued

Pyraislium salts of formula

| No | $R_2$ | $R_3$ | $R_4$ | $R_5$ | $R_6$ | Analysis Calculated | Analysis Found | M.P. °C. | Method |
|---|---|---|---|---|---|---|---|---|---|
| 16 | Br | Cl | Br |  | Cl |  |  | (dec) 193 |  |
| 17 | Br |  | F |  | F |  |  | (dec) 111–114 |  |
| 18 | Br |  | CN |  | Br |  |  | 62 |  |
| 19 | $CH_3$ | $CH_3$ |  |  | Br |  |  | 123.5–126.5 |  |
| 20 | Cl | Cl |  |  | Br |  |  | 118–129 |  |
| 21 | Br | Br |  |  | Br |  |  |  |  |
| 22 | Br | Br |  | Br | Br |  |  | 164–164.5 |  |
| 23 | Br |  |  |  | $C_2H_5$ | C 59.77 H 5.22 N 11.15 | C 59.86 H 5.14 N 11.12 | hygroscopic gum |  |
| 24 | $C_2H_5$ |  |  |  | $\overset{CH_3}{\underset{}{CHC_2H_5}}$ |  |  | hygroscopic gum |  |
| 25 | $CH_3$ |  | Br |  | $CH_3$ | C 57.70 H 5.42 N 10.77 | C 57.38 H 5.13 N 10.49 | hygroscopic gum |  |
| 26 | Br | F | Br |  | Br |  |  | 175–179 (dec) |  |
| 27 | $CH_3$ |  |  |  | $CH_3$ |  |  | 143–145 | A |
| 28 | Br |  | $CH_3$ |  | Br |  |  | 178–179 | A |
| 29 | $C_2H_5$ |  |  |  | $C_2H_5$ | C 70.41 H 7.00 N 12.17 | C 70.41 H 7.14 N 12.10 | gum | A |
| 30 | Br |  |  |  |  |  |  | 109–110.5 |  |
| 31 | Br |  |  |  | Br |  |  | 130–132.5 | B |
| 32 | Br |  | $SO_2N(CH_3)_2$ |  | Br |  |  | 65–78 |  |
| 33 | Br |  | $SO_2OCH_2C_6H_5$ |  | Br |  |  |  |  |
| 34 | Br |  | $O\text{—}C_6H_5$ |  | Br |  |  |  |  |
| 35 | Br |  | $NHCOCH_3$ |  | Br |  |  | 173–179 |  |
| 36 | Br | Br |  |  |  |  |  |  |  |
| 37 | Br | $SO_2CH_3$ | Br |  | Br |  |  |  |  |
| 38 | Br |  |  |  | I |  |  |  |  |
| 39 | I |  |  |  | I |  |  |  |  |
| 40 | Br |  |  |  | $CH_3$ |  |  |  |  |
| 41 | I |  |  |  | $CH_3$ |  |  |  |  |
| 42 | F |  |  |  | Br |  |  |  |  |
| 43 | F |  |  |  | F |  |  |  |  |
| 44 | F |  |  |  | I |  |  |  |  |
| 45 | Cl |  |  |  | I |  |  |  |  |
| 46 | Cl |  |  |  | Br |  |  | gum |  |
| 47 | Br |  |  |  | $CH(CH_3)_2$ |  |  |  |  |
| 48 | Br |  |  | Br |  |  |  | 95–97 |  |
| 49 |  |  | $SO_2CH_3$ |  |  |  |  | 108–110 |  |
| 50 | Br |  | Br |  | $SO_2C_4H_9$ |  |  |  |  |
| 51 | I | I |  | I |  |  |  |  |  |
| 52 | Br | Br |  | Br |  |  |  | gum |  |
| 53 | Br |  | $SO_2CH_3$ |  |  |  |  | 77–84 (dec) |  |
| 54 | $C_2H_5$ |  | Br |  | $C_2H_5$ |  |  | 104–105 |  |
| 55 | Br |  | $CH_3$ |  | $CH_3$ |  |  | 133–135 |  |
| 56 | Cl |  | I |  | I |  |  | 180–182 (dec) |  |
| 57 | Br |  | I |  | I |  |  | 129–131 |  |
| 58 | I |  | I |  | I |  |  | 148–150 (dec) |  |

TABLE Il

Salts of Formula:

[structure shown]

| R₂ | R₄ | R₆ | M.P. |
|---|---|---|---|
| Br | Br | Br | 89–92 |

TABLE Im

Salts of Formula:

[structure shown]

| R₂ | R₄ | R₆ | M.P. |
|---|---|---|---|
| Br | Br | Br | 150–152 |

TABLE Io

Salts of Formula:

[structure shown]

| No | R₂ | R₄ | R₆ | Analysis Calculated | Found | M.P. (°C.) |
|---|---|---|---|---|---|---|
| 1 | CF₃ | Br | Br | C 45.86 | C 46.16 | 126–127 (dec) |
|   |   |   |   | H 3.36 | H 3.19 |   |
|   |   |   |   | N 8.89 | N 9.01 |   |
|   |   |   |   | F 9.04 | F 9.23 |   |
| 2 | Br | CF₃ | Br | C 47.08 | C 47.24 | 140–142 (dec) |
|   |   |   |   | H 3.13 | H 3.20 |   |
|   |   |   |   | N 9.15 | N 9.08 |   |
|   |   |   |   | F 9.31 | F 9.46 |   |
|   |   |   |   | Br 26.11 | Br 26.11 |   |
| 3 | Cl | Cl | Cl | C 55.39 | C 55.69 | 105–106 |
|   |   |   |   | H 4.04 | H 3.92 |   |
|   |   |   |   | N 11.23 | N 11.02 |   |
| 4 | I | Br | Br | C 41.22 | C 41.51 | 142–143 (dec) |
|   |   |   |   | H 2.86 | H 3.00 |   |
|   |   |   |   | N 8.36 | N 8.35 |   |
|   |   |   |   | Br 23.85 | Br 23.56 |   |
| 5 | CH₃ | CH₃ | CH₃ | C 69.55 | C 69.19 | 88–91 (dec) |
|   |   |   |   | H 6.86 | H 6.83 |   |
|   |   |   |   | N 12.30 | N 12.06 |   |
| 6 | Br | Cl | Br | C 47.73 | C 47.51 | 128–132 |
|   |   |   |   | H 3.31 | H 3.35 |   |

TABLE Io-continued

Salts of Formula:

[structure shown]

| No | R₂ | R₄ | R₆ | Analysis Calculated | Found | M.P. (°C.) |
|---|---|---|---|---|---|---|
|   |   |   |   | N 9.68 | N 9.66 |   |

EXAMPLE 2

Preparation of 2,4,6-tribromo-N-nitro-N-(2-propynyl) aniline 2,4,6-tribromo-N-nitroaniline (5.0 g; 0.01334 mol) is reacted with a methanolic solution of sodium hydroxide (0.53 g; 0.01324 mol) in the presence of methanol (60 ml). The solvent is then removed, and the residue dried. The thus obtained sodium salt is dissolved in dimethyl sulfoxide (DMSO) and reacted with 3-bromopropyne (1.52 g; 0.0147 mol) at 25° C. The reaction mixture is stirred 16 hours and then poured into water. The title product is extracted with ether (3×125 ml), the combined extract washed with water, dilute sodium hydroxide, water and brine. The ethereal solution is then dried over magnesium sulfate and the solution concentrated to afford the product, mp. 58°–58.5° C.

By the above method, a number of N-substituted phenylnitramines are prepared. These are listed in Table II below.

TABLE II

N—substituted phenylnitramines

| No | R₁ | R₂ | R₃ | R₄ | R₅ | R₆ | M.P. °C. |
|---|---|---|---|---|---|---|---|
| 1 | —CH₂CH=CH₂ | Br |   | Br |   | Br | oil |
| 2 | CH₂—⟨C₆H₄⟩—NO₂ | Br |   | Br |   | Br | 153–156 |
| 3 | CH₂CO₂CH₃ | Br |   | Br |   | Br | 122 |
| 4 | CH₂CH₂CO₂CH₃ | Br |   | Br |   | Br | 82–83 |
| 5 | CH₂C≡CH | Br |   |   |   | Br | 75–77 |
| 6 | CH₂CN | Br |   | Br |   | Br | 85–87 |
| 7 | CH₃<br>\|<br>CH—C₆H₅ | Br |   | Br |   | Br | 135–138 |
| 8 | CH₂C₆H₅ |   |   | Br |   | Br | 84–86 |
| 9 | CH₂C₆H₅ | Br |   | Br |   | Br | 72– |

TABLE II-continued

N—substituted phenylnitramines $$R_1\text{—}N\text{—}NO_2$$

(phenyl ring with $R_2, R_3, R_4, R_5, R_6$ substituents)

| No | $R_1$ | $R_2$ | $R_3$ | $R_4$ | $R_5$ | $R_6$ | M.P. °C. |
|---|---|---|---|---|---|---|---|
| 10 | $CH_3$ | Br | | | | Br | 73 125–127 |
| 11 | $CH(C_2H_5)_2$ | $NO_2$ | $CH_3$ | $CH(CH)_2$ | | $NO_2$ | 126–126.5 |
| 12 | $CH(C_2H_5)_2$ | $NO_2$ | $CH_3$ | $CH_3$ | | $NO_2$ | 75.5–77 |
| 13 | $CH_3$ | Br | Br | | | Br | 94.5–95 |
| 14 | $n\text{-}C_{12}H_{25}$ | Br | Br | | | Br | Liquid |

EXAMPLE 3

Preparation of (2-Propynyloxy) (2,4,6-tribromophenyl) diimide-1-oxide

A suspension of the silver salt of 2,4,6-tribromophenylnitramine (4.82 g; 0.01 mol) in ether is reacted with 3-bromopropyne (1.3 g; 0.011 mol) under a nitrogen atmosphere at 25° C. After 16 hours the mixture is filtered through a layer of celite, the ether solution is washed with water, dilute sodium hydroxide and again with water and then dried over anhydrous magnesium sulfate. The solvent is then removed under vacuum, the residue dissolved in methylene chloride and filtered through a layer of alumina. The filtrate is concentrated and crystallized from petroleum ether. Thin layer chromatography (silica gel; hexane:CH$_2$Cl$_2$ in a 1:1 ratio) and NMR indicate the product to be a 83 to 17 percent mixture of the O and N substituted products.

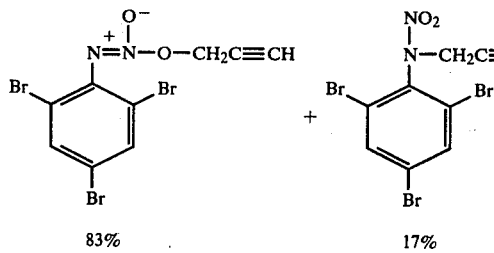

83%     17%

Substituting methyl iodide or n-dodecyl bromide for 3-bromopropyne-1 in the above reaction, the corresponding O-methyl and O-n-dodecyl analogs are obtained, respectively.

Similarly reacting the silver salt of 2,6-dibromophenylnitramine with methyl iodide affords the corresponding O-methyl compound.

EXAMPLE 4

Preparation of substituted benzylnitramines

A solution of the appropriate benzyl halide or mesylate (0.03 mol) and ammonium nitrourethane in dry dimethylformamide (50 ml) is heated at 80° C. for four hours. The reaction mixture is cooled and poured into ice water, and then extracted three times with ether. The combined extracts are washed with water and dried over anhydrous magnesium sulfate. Next, anhydrous ammonia gas is passed into the solution for 30 minutes. The precipitated material is isolated, washed in the ether and then dissolved in water (100 ml). The aqueous solution is stirred vigorously and its pH adjusted to 5. The precipitated product is filtered, washed with water and dried. If desired, the product may be recrystallized from a mixture of hexane:toluene (1:1).

The thus prepared products are shown in Table III below.

TABLE III

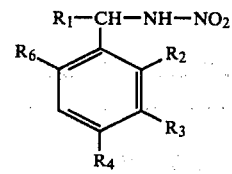

| No | $R_2$ | $R_3$ | $R_4$ | $R_6$ | $R_1$ | M.P. °C. |
|---|---|---|---|---|---|---|
| 1 | Cl | H | H | Cl | H | 121–122.5 |
| 2 | H | H | Cl | H | H | 90–91 |
| 3 | Cl | Cl | H | Cl | H | 71–72 |
| 4 | $CH_3$ | H | H | $CH_3$ | H | 93 |
| 5 | CL | H | H | Cl | $CH_3$ | 99–101 |
| 6 | Cl | H | Cl | H | H | 72–75 |
| 7 | $CF_3$ | H | H | Br | H | |
| 8 | Br | H | H | Br | H | |
| 9 | Br | H | H | Cl | H | |
| 10 | F | H | H | F | H | |
| 11 | Br | H | H | Br | $CH_3$ | |
| 12 | $CF_3$ | H | H | Br | $CH_3$ | |
| 13 | Br | H | H | Br | F | |
| 14 | Br | H | H | Br | $CF_3$ | |
| 15 | Br | H | H | Br | $C_6H_5$ | |
| 16 | Cl | H | H | Cl | $CF_3$ | |
| 17 | Cl | H | H | Cl | CN | |
| 18 | Cl | H | H | Cl | CN | |
| 19 | Cl | H | H | Cl | $SO_2CH_3$ | |

EXAMPLE 5

Preparation of Miscellaneous Salts of Substituted Benzylnitramines

By the methods of Example 1, a number of salts of various benzylnitramines are prepared. These are shown in Table IV below.

TABLE IV $$\text{R}_4\text{-}\underset{\underset{\text{R}_3}{}}{\underset{\text{R}_2}{}}\text{C}_6\text{H}_2(\text{R}_6)\text{-CH}(\text{R}_1)\text{-CH=N}^+(\text{O}^-)_2 \ \ X^+$$

| No | $R_2$ | $R_3$ | $R_4$ | $R_6$ | $R_1$ | $X^+$ | M.P. °C. |
|---|---|---|---|---|---|---|---|
| 1 | $CH_3$ | H | H | $CH_3$ | H | $\overset{+}{N}H_4$ | 93–93 |
| 2 | Cl | H | Cl | H | H | $\overset{+}{N}H_4$ | 120–122 |
| 3 | Cl | H | H | Cl | $CH_3$ | $C_6H_5\overset{+}{C}H\overset{}{N}H_3$ / $CH_3$ | 165–172 |
| 4 | H | H | Cl | H | H | $\overset{+}{N}H_4$ | 103–125 |
| 5 | Cl | H | H | Cl | H | $\overset{+}{N}H_4$ | |
| 6 | Cl | H | H | Cl | H | $Na^+$ | >260 |
| 7 | Cl | H | H | Cl | $CH_3$ | $Na^+$ | >300 |
| 8 | Cl | H | H | Cl | $CH_3$ | $NH_4^+$ | |
| 9 | Br | H | H | Br | H | $Na^+$ | |
| 10 | Cl | H | H | Cl | $CF_3$ | $Na^+$ | |
| 11 | Cl | H | H | Cl | $CH_3$ | 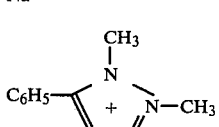 | |
| 12 | Cl | H | H | Cl | H | 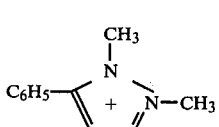 | |
| 13 | Cl | H | H | Cl | H | $C_{18}H_{35}\overset{+}{N}H_3$ | |
| 14 | Br | H | H | Br | $CH_3$ | $Na^+$ | |
| 15 | Br | H | H | Br | $CF_3$ | H | 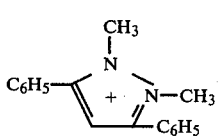 |

EXAMPLE 6

Lithium diisopopylamide mediated N-nitration of anilines

A solution of diisopropylamine (0.20 mol) in diethylether (300 ml) is cooled to −75° C. under $N_2$ and lithiated with n-butyllithium (0.20 ml of a 1.6 M solution hexane). The solution is allowed to warm slowly to 0° C. over four hours, then is cooled down to −60° C. A solution of the appropriate aniline (0.10 mol) in ether (300 ml) is added dropwise and the reaction mixture is allowed to warm to 0° C. over one hour. Cooling the reaction mixture back to −60° C. is followed by the addition (dropwise) of methyl nitrate (0.10 mol). The reaction mixture is allowed to warm to ambient temperature overnight, and poured onto 300 ml water. The aqueous layer is washed with ether, cooled in an ice bath, and acidified dropwise with concentrated hydrochloric acid. The mixture is extracted with ether, the combined ether extracts are washed successively with cold 5% HCl, water and brine. Removal of the solvent under vacuum affords the product.

By the above method and other methods known in the art, a number of N-nitroanilines are prepared, and are shown in Table V below.

TABLE V

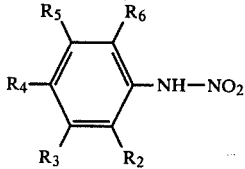

| No | $R_2$ | $R_3$ | $R_4$ | $R_5$ | $R_6$ | M.P. °C. |
|---|---|---|---|---|---|---|
| 1 | Br | | Br | Cl | $CH_3$ | 140 (dec) |
| 2 | $CH_3$ | $CH_3$ | | | Br | 94–94.5 |
| 3 | $CH_3$ | | $CH_3$ | | I | 93–98 |
| 4 | Br | | Br | | $SO_2C_6H_5$ | 116–117 |
| 5 | Br | Cl | $CH_3$ | | Br | 137.5–138 |
| 6 | Br | Cl | Br | | Cl | 126 (dec) |
| 7 | Br | $CH_3$ | $CH_3$ | | Br | 123.5–124 |
| 8 | Br | | $COC_6H_5$ | | Br | 134.5–135 |
| 9 | Br | | CN | | Br | 139–139.5 |
| 10 | Br | Br | | Br | Br | 140–154 (dec) |
| 11 | $C_2H_5$ | | Br | | $CH(CH_3)_2$ | 113–115 (dec) |
| 12 | $C_2H_5$ | | Br | | $\underset{CHC_2H_5}{\overset{CH_3}{\mid}}$ | 118–122 (dec) |
| 13 | Br | | Br | | $C_2H_5$ | 92–98 |
| 14 | Cl | | Cl | | I | 119–122 |
| 15 | Br | | Br | | $CH_3$ | 106–108 |
| 16 | $CH(CH_3)_2$ | | Br | | $CH_3$ | 70–80 |
| 17 | Br | | $C_2H_5$ | | Br | 66–80 |
| 18 | Br | | | | $C_2H_5$ | 40–50 |
| 19 | $CH_3$ | | Br | | $C(CH_3)_3$ | 85–90 |
| 20 | $C_2H_5$ | | | | $\underset{CH-C_2H_5}{\overset{CH_3}{\mid}}$ | gum |
| 21 | Br | F | Br | | Br | 128–129 |
| 22 | Cl | | Cl | | I | 120–122 |
| 23 | Br | | $CH_3$ | | Br | 122–123 |
| 24 | Br | | | | | 61–62 |
| 25 | $CF_3$ | | | Br | | 75–77 |
| 26 | Br | | | | Br | 108–111 (dec) |
| 27 | $CH_3$ | | | | $CH_3$ | 104.5–105 (dec) |
| 28 | Cl | Cl | | | | 58–60 |
| 29 | $CH_3$ | | Br | | $CH_3$ | 127.5–129 |
| 30 | $CH_3$ | | | | $C(CH_3)_3$ | oil |
| 31 | $CH_3$ | | | | $CH(CH_3)_2$ | oil |
| 32 | $C_2H_5$ | | | | $CH(CH_3)_2$ | |
| 33 | $C_2H_5$ | | | | $C_2H_5$ | 71.5–73.5 |
| 34 | Br | | | Br | | 94–95.5 |
| 35 | I | I | | I | | |
| 36 | Br | Br | | Br | | 112.5–114 (dec) |
| 37 | Br | Br | | | Br | |
| 38 | Cl | Cl | Br | | | 98–100 |
| 39 | Cl | Cl | | | Br | 84–86 |
| 40 | $CH_3$ | | 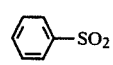 | | | |
| 41 | Br | | 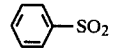 | | | |
| 42 | Br | | $SO_3CH_2C_6H_5$ | | Br | |
| 43 | Br | $NHCOCH_3$ | Br | | Br | |
| 44 | $CF_3$ | | | | Br | |
| 45 | Br | | | | I | |
| 46 | I | | | | I | |
| 47 | I | | | | Cl | |
| 48 | I | | | | Br | |
| 49 | I | | I | | I | 140–141.5 |
| 50 | Br | | Br | | $C_4H_9SO_2$ | 137 (dec) |
| 51 | Br | | $CH_3SO_2$ | | Br | 161–161.5 |
| 52 | Br | | $CH_3CO$ | | Br | 124–124.5 |

TABLE V-continued

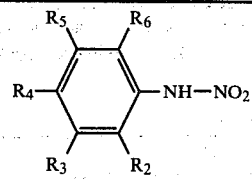

| No | R2 | R3 | R4 | R5 | R6 | M.P. °C. |
|---|---|---|---|---|---|---|
| 53 | CH3CO | | Br | | Br | |
| 54 | Br | | SO2N(CH3)2 | | Br | 143–144 |
| 55 | Br | | NHCOCH3 | | Br | 168 (dec) |
| 56 | | | ⟨C6H5⟩—SO2 | | | 183–184 (dec) |
| 57 | Br | | ⟨C6H5⟩—S— | | Br | |
| 58 | Br | | ⟨C6H5⟩—SO2 | | Br | 145 (dec) |
| 59 | C2H5 | | Br | | C2H5 | 66–67 |
| 60 | Br | | I | | I | 118.5–121 |
| 61 | Br | | CH3 | | CH3 | 103–105 |
| 62 | Cl | | I | | I | 118–119 |
| 63 | CH3S | | Br | | Br | |

EXAMPLE 7

Evaluation of 2,4,6-trisubstituted-N-nitroaniline salts as Dwarfing and Stem Stiffening agents for Barley In the following tests, test compounds are dissolved or dispersed in acetone-water (1:1) mixtures at the final concentration corresponding to the kg/ha rates indicated in the table below. The solution also contains 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2-propanol.

The plant species used in these tests are barley (*Hordeum vulgare*), (Mexico) and soybean (*Glycine max-*)Adelphia.

The solution or dispersion of the compound under test is sprayed at a rate of 747 l/ha with a moving nozzle along an overhead stationary track. The spray nozzle moves at a constant speed over the plants.

The plants are grown in plastic pots, and are well established at the time of treatment. The seedlings of barley are 10 to 20 cm in height, while the seedlings of soybeans are at the second to third trifoliate stage. Plants are watered prior to treatment and then sprayed to provide the kg/ha rate of test compound desired. After spraying the plants are placed on greenhouse benches and watered and fertilized in accordance with normal greenhouse procedures.

Three weeks after spraying the plants are measured and harvested. Harvesting is done at the boot stage. All treatments are replicated six times and comparisons are made against untreated controls. Data obtained are reported in Table VI below as percent reduction in plant height over untreated controls.

TABLE VI

Evaluation of test compounds as Barley dwarfing agents

| Compound | Rate kg/ha | % Reduction in Plant Height over untreated controls |
|---|---|---|
| 1,2-Dimethyl-3,5-diphenyl-pyrazolium salt with 2,4,6-tribromo-N—aci-nitroaniline | 1.5 / 0.50 / 0.17 | 15 / 8.7 / 37.8 |
| 4-Methoxy-1,2-dimethyl-3,5-diphenylpyrazolium salt with 2,4,6-tribromo-N—aci-nitroaniline | 2.24 / 0.56 / 0.11 | >60 / >20 <35 / >10 <15 |

TABLE VIa

Evaluation of test compounds for Dwarfing of Barley

| Compound | Kg/ha Rate | % Reduction in Plant Height over untreated controls |
|---|---|---|
| 2,4,6-Tribromo-N—nitroaniline, potassium salt | 1.5 / 0.50 / 0.17 | 2.0 / 11.8 / 2.7 |
| 2,4,6-Tribromo-N—nitroaniline, sodium salt 0.17 | 1.5 / 0.50 / 6.2 | 13.0 / 13.0 |
| 2,4,6-Tribromo-N—nitroaniline with octylamine (1:1) | 1.5 / 0.50 / 0.17 | 11.1 / 13.0 / 10.5 |
| 2,4,6-Tribromo-N—nitroaniline with ammonia (1:1) | 1.5 / 0.50 | 15.3 / 16.3 |
| 2,4,6-Tribromo-N—nitroaniline tetrabutyl, ammonium salt | 1.5 / 0.50 / 0.17 | 15.8 / — / 10.5 |
| (2-Chloroethyl)trimethyl ammonium salt with 2,4,6-tribromo-N—aci-nitroaniline | 1.5 / 0.50 / 0.17 | 28.1 / 16.5 / 23.1 |
| 2,4,6-Tribromo-N—nitroaniline with methylamine (1:1) | 2.24 / 0.56 / 0.11 | >50 / >50 / 10 |
| 4-Methoxy-1,2-dimethyl-3,5-diphenylpyrazolium salt with | 2.24 / 0.56 | >60 / >20 <35 |

TABLE VIa-continued

Evaluation of test compounds for Dwarfing of Barley

| Compound | Kg/ha Rate | % Reduction in Plant Height over untreated controls |
|---|---|---|
| 2,4,6-tribromo-N—aci-nitroaniline | 0.11 | >10 <15 |
| 2,4,6-Tribromo-N—nitro-aniline, magnesium salt | 2.0 | >10 <15 |
| | 1.0 | >10 <15 |
| | 0.5 | >10 <15 |
| 2,4,6-Tribromo-N—nitro-aniline, Calcium salt | 2.0 | >10 <15 |
| | 1.0 | >10 <15 |
| | 0.5 | >10 <15 |

TABLE VIb

Evaluation of test compounds as Dwarfing agents and stem stiffening agents for soybeans

| Compound | Rate Kg/ha | % Reduction in Plant Height over untreated controls |
|---|---|---|
| 2,4,6-Tribromo-N—nitro-aniline, sodium salt | 0.25 | >40 |
| | 0.125 | >35 |
| 2,4,6-Tribromo-N—nitro-aniline, potassium salt | 0.50 | >30 |
| | 0.25 | >5 |
| | 0.125 | >5 |
| 2,4,6-Tribromo-N—nitro-aniline, magnesium salt | 2.0 | >10 <15 |
| | 1.0 | >10 <15 |
| | 0.5 | >20 <35 |
| 2,4,6-Tribromo-N—nitro-aniline, calcium salt | 2.0 | >10 <15 |
| | 1.0 | >10 <15 |
| | 0.5 | >10 <15 |
| 2,4,6-Tribromo-N—nitro-aniline with ammonia (1:1) | 2.0 | >60 |
| | 0.5 | >60 |
| | 0.1 | >10 <15 |
| 2,4,6-Tribromo-N—nitro-aniline with methylamine (1:1) | 2.0 | >60 |
| | 0.5 | >60 |
| | 0.1 | >10 <15 |
| (2-Chloroethyl)trimethyl ammonium salt with 2,4,6-Tribromo-N—aci-nitroaniline | 2.0 | >60 |
| | 0.5 | >60 |
| | 0.1 | normal |
| Tetrabutylammonium salt with 2,4,6-tribromo-N—nitro-aniline | 0.5 | >50 |
| | 0.25 | >35 |
| | 0.125 | >25 |
| Benzyltriethylammonium salt with 2,4,6-tribromo-N—aci-nitroaniline | 0.5 | >50 |
| | 0.25 | >35 |
| | 0.125 | >25 |
| 1-Hexadecylpyridinium salt with 2,4,6-tribromo-N—aci-nitroaniline | 0.5 | >50 |
| | 0.25 | >35 |
| | 0.125 | >35 |
| 1,1-Dimethylpiperidinium salt with 2,4,6-tribromo-N—aci-nitroaniline | 0.5 | >50 |
| | 0.25 | >35 |
| | 0.125 | >25 |
| Dibenzylamine(1:1)with 2,4,6-tribromo-N—nitroaniline | 0.5 | >50 |
| | 0.25 | >35 |
| | 0.125 | >25 |
| Dodecylamine with 2,4,6-tribromo-N—nitroaniline | 0.5 | >35 |
| | 0.25 | >25 |
| | 0.125 | >15 |
| Methyltriphenyl phosphonium salt with 2,4,6-tribromo-N—aci-nitroaniline | 0.5 | >50 |
| | 0.25 | >35 |
| | 0.125 | >25 |
| Tributyl(2,4-dichloro-benzyl)phosphonium salt with aniline | 0.5 | >50 |
| | 0.25 | >25 |
| | 0.125 | >8 |
| 1,2-Dimethyl-3,5,diphenyl-pyrazolium salt with 2,4,6-tribromo-N—aci-nitroaniline | 0.5 | >20 <35 |
| | 0.25 | >10 <15 |
| | 0.125 | normal |
| 4-Methoxy-1,2-dimethyl-3,5-diphenylpyrazolium salt with 2,4,6-tribromo-N—aci-nitroaniline | 0.5 | >35 |
| | 0.25 | >35 |
| | 0.125 | >10 |
| 3-(p-Fluorophenyl)-1,2-dimethyl-5-phenylpyrazolium salt with 2,4,6-tribromo-N—aci-nitroaniline | 0.5 | >25 |
| | 0.25 | >25 |
| | 0.125 | >20 |

TABLE VIb-continued

Evaluation of test compounds as Dwarfing agents and stem stiffening agents for soybeans

| Compound | Rate Kg/ha | % Reduction in Plant Height over untreated controls |
|---|---|---|
| 1,2-Dimethyl-3-(methylpiperi-dino)-5-phenylpyrazolium salt with 2,4,6-tribromo-N—aci-nitroaniline | 0.5 | >25 |
| | 0.25 | >25 |
| | 0.125 | >20 |
| 1,2-Dimethyl-3,5-diphenyl-pyrazolium salt with 4,6-dibromo-α,α,α-trifluoro-N—aci-nitro-o-toluidine | 0.5 | >40 |
| | 0.25 | >40 |
| | 0.125 | >20 |
| 1,2-Dimethyl-3,5-diphenyl-pyrazolium salt with 2,6-dibromo-α,α,α-trifluoro-N—aci-nitro-o-toluidine | 0.5 | >20 |
| | 0.25 | >15 |
| | 0.125 | >10 |
| 1,2-Dimethyl-3,5-diphenyl-pyrazolium salt with 2,4,6-trichloro-N—aci-nitro-aniline | 0.5 | >25 |
| | 0.25 | >15 |
| | 0.125 | >10 |
| 1,2-Dimethyl-3,5-diphenyl-pyrazolium salt with 2,4-dibromo-6-iodo-N—aci-nitroaniline | 0.5 | >25 |
| | 0.25 | >15 |
| | 0.125 | >10 |
| cis-1,2-Dimethyl-3,5-diphenyl-pyrazolidinium salt with 2,4,6-tribromo-N—nitroaniline | 0.5 | >60 |
| | 0.25 | >30 |
| | 0.125 | >20 |
| 1,2-Dimethyl-3,5-diphenyl-pyrazolium salt with 2,4,6-Trimethyl-N—aci-nitroaniline | 0.5 | >10 |
| | 0.25 | >5 |
| | 0.125 | slight increase |
| 3-Cyclohexyl-1,2-dimethyl-5-phenylpyrazolium salt with 2,4,6-tribromo-N—aci-nitro-aniline | 0.5 | >40 |
| | 0.25 | >20 |
| | 0.125 | >10 |
| 1,2-Dimethyl-3,5-diphenyl-pyrazolium salt with 2,6-dibromo-4-chloro-N—aci-nitroaniline | 0.5 | >40 |
| | 0.25 | >30 |
| | 0.125 | >25 |

EXAMPLE 8

Evaluation of test compounds for Increasing axillary Branching and improving the canopy of Broad leaf plants using Soybeans (*Glycine max*) Adelphia variety as the plant species In these tests seedling soybean plants approximately three weeks old, and grown in plastic pots to the 2nd to 3rd trifoliate stage, are sprayed with solutions or dispersions of test compound prepared as described in Example 7 above. The same spraying apparatus, described in Example 7 above, is used and after spraying the plants are placed on greenhouse benches and watered and fertilized. Three weeks after treatment the plants are examined to determine what effect the application of test compound has had on the axillary branching and canopy development of the treated plants.

Increased axillary branching and improved canopy are biological responses which are highly advantageous in the growing of ornamental plants. These responses also have advantage in many crops since increased branching may result in the greater production of fruit, while improved canopy tends to shade and suppress the growth of undesirable weeds that compete with the crops for sunlight, water and plant nutrients. Data obtained are reported in table VII below where axillary branching and canopy are reported as percent increase over untreated controls.

TABLE VII

Evaluation of test compounds for increasing axillary branching and improving the canopy of treated broad leaf plants using soybeans (var. Adelphia) as the plant species

| Compound | Rate kg/ha | % Increase in axillary branching over untreated controls | % Increase in Plant Canopy over untreated controls |
|---|---|---|---|
| 1,2-Dimethyl-3,5-diphenyl- | 0.5 | >10 <15 | >10 <15 |
| pyrazolium salt with 2,4,6- | 0.25 | >10 <15 | >20 <35 |
| tribromo-N—aci nitroaniline | 0.125 | >10 <15 | >10 <15 |
| 4-Methoxy-1,2-dimethyl-3,5- | 0.5 | >10 <15 | >20 <35 |
| diphenylpyrazolium salt with | 0.25 | normal | >20 <35 |
| 2,4,6-Tribromo-N—aci-nitroaniline | 0.125 | normal | normal |
| 3-(p-Fluorophenyl)-1,2-dimethyl-3,5- | 0.5 | normal | >10 <15 |
| diphenylpyrazolium salt with | 0.25 | >10 <15 | >10 <15 |
| 2,4,6-tribromo-N—aci-nitroaniline | 0.125 | normal | normal |
| 1,2-Dimethyl-3,5-diphenylpyrazolium | 0.5 | >10 <15 | >10 <15 |
| salt with 4,6-dibromo-α,α,α-tri- | 0.25 | >10 <15 | >10 <15 |
| fluoro-N—aci-o-toluidine | 0.125 | >10 <15 | >20 <35 |
| 1,2-Dimethyl-3,5-diphenylpyrazolium | 0.5 | >20 <35 | >20 <35 |
| salt with 2,4-dibromo-6-iodo-N— | 0.25 | >20 <35 | >20 <35 |
| aci-nitroaniline | 0.125 | >10 <15 | >10 <15 |
| 1,2-Dimethyl-3,5-diphenylpyrazolium | 0.5 | >10 <15 | >10 <15 |
| salt with 2,4,6-trimethyl-N—aci- | 0.25 | >10 <15 | >10 <15 |
| nitroaniline | 0.125 | normal | normal |
| 3-Cyclohexyl-1,2-dimethyl- | 0.5 | >10 <15 | slight reduction |
| 5-phenylpyrazolium salt | 0.25 | >10 <15 | >10 <15 |
| with 2,4,6-tribromo-N— | 0.125 | >10 <15 | >10 <15 |
| aci-nitroaniline | | | |
| 1,2-Dimethyl-3,5-diphenyl- | 0.5 | >10 <15 | >10 <15 |
| pyrazolium salt with 2,6- | 0.25 | >10 <15 | >10 <15 |
| dibromo-4-chloro-N—aci- | 0.125 | >10 <15 | normal |
| nitroaniline | | | |
| 2,4,6-Tribromo-N—nitroaniline, | 0.50 | >20 <35 | >10 <15 |
| sodium salt | 0.25 | >20 <35 | >20 <35 |
| | 0.125 | >20 <35 | >20 <35 |
| 2,4,6-Tribromo-N—nitroaniline, | 0.50 | >20 <35 | normal |
| potassium salt | 0.25 | normal | >10 <15 |
| | 0.125 | normal | >10 <15 |
| (2-chloroethyl)trimethyl | 0.50 | >20 <35 | >20 <35 |
| ammonium salt with 2,4,6- | 0.25 | >10 <15 | >10 <15 |
| tribromo-N—aci-nitroaniline | 0.125 | normal | >10 <15 |
| 2,4,6-tribromo-N—nitroaniline | 0.50 | >10 <15 | Injury |
| with ammonia (1:1) | 0.25 | >10 <15 | >20 <35 |
| | 0.125 | >20 <35 | >20 <35 |
| 2,4,6-Tribromo-N—nitroaniline, | 0.50 | >10 <15 | slight reduction |
| diisopropylamine (1:1)salt | 0.25 | >10 <15 | >10 <15 |
| | 0.125 | >10 <15 | >10 <15 |
| 2,4,6-Tribromo-N—nitroaniline, | 0.50 | >10 <15 | slight reduction |
| triethylamine (1:1)salt | 0.25 | >20 <35 | slight reduction |
| | 0.125 | normal | >10 <15 |
| 2,4,6-Tribromo-N—nitroaniline, | 0.50 | >10 <15 | slight reduction |
| octylamine salt | 0.25 | >10 <15 | >10 <15 |
| | 0.125 | normal | >10 <15 |
| 2,4,6-tribromo-N—nitroaniline, | 0.50 | >10 <15 | >10 <15 |
| tetrabutylammonium salt | 0.25 | >20 <35 | >20 <35 |
| | 0.125 | >20 <35 | >20 <35 |
| 2,4,6-Tribromo-N—nitroaniline | 0.5 | >10 <15 | >20 <35 |
| with dibenzylamine | 0.25 | normal | >10 <15 |
| | 0.125 | normal | normal |
| 2,4,6-Tribromo-N—nitroaniline | 0.5 | >20 <35 | >10 <15 |
| with dodecylamine | 0.25 | >10 <15 | >10 <15 |
| | 0.125 | normal | normal |
| Benzyltriethyl ammonium salt | 0.5 | >10 <15 | >10 <15 |
| with 2,4,6-tribromo-N—aci- | 0.25 | normal | >10 <15 |
| nitroaniline | 0.125 | normal | normal |
| 1,1-Dimethylpiperidinium salt | 0.5 | >10 <15 | >20 <35 |
| with 2,4,6-tribromo-N—aci- | 0.25 | normal | >10 <15 |
| nitroaniline | 0.125 | normal | normal |
| 2,4,6-Tribromo-N—aci-nitro- | 0.5 | >20 <35 | moderate reduction |
| aniline calcium salt (2:1) | 0.25 | >20 <35 | slight reduction |
| | 0.125 | >20 <35 | >10 <15 |
| 2,4,6-Tribromo-N—aci-nitro- | 0.5 | >20 <35 | moderate reduction |
| aniline, magnesium salt (2:1) | 0.25 | >20 <35 | moderate reduction |
| | 0.125 | >10 <15 | >10 <15 |
| 2,4,6-Tribromo-N—nitro | 0.5 | >20 <35 | moderate reduction |
| aniline with cis 1,2-dimethyl- | 0.25 | >20 <35 | moderate reduction |
| 3,5-diphenylpyrazolidine | 0.125 | >10 <15 | >20 <35 |
| Tributyl(2,4-dichlorobenzyl) | 0.5 | >20 <35 | moderate reduction |
| phosphonium salt with 2,4,6- | 0.25 | >10 <15 | >10 <15 |
| tribromo-N—aci-nitroaniline | 0.125 | normal | normal |
| 1-Hexadecylpyridinium salt | 0.5 | normal | >10 <15 |
| with 2,4,6-tribromo-N—aci- | 0.25 | normal | >10 <15 |

TABLE VII-continued

Evaluation of test compounds for increasing axillary branching and improving the canopy of treated broad leaf plants using soybeans (var. Adelphia) as the plant species

| Compound | Rate kg/ha | % Increase in axillary branching over untreated controls | % Increase in Plant Canopy over untreated controls |
|---|---|---|---|
| nitroaniline | 0.125 | normal | normal |
| Methyltriphenylphosphonium salt with 2,4,6-tribromo-N—aci-nitroaniline | 0.5 | >10 <15 | >20 <35 |
|  | 0.25 | normal | >10 <15 |
|  | 0.125 | normal | normal |
| Methylamine salt with 2,4,6-tribromo-N—aci-nitroaniline | 0.5 | normal | >10 <15 |
|  | 0.25 | normal | >10 <15 |
|  | 0.125 | normal | normal |

EXAMPLE 9

Evaluation of Test Compounds To Determine Their Effectiveness for Increasing Flowering of Plants Using Soybeans (*Glycine max*) Var. Adelphia As The Plant Species In the following tests seedling soybean plants growing in plastic cups are sprayed with aqueous-acetone solutions or dispersions of test compounds when they have reached the 2nd to 3rd trifoliate stage. Test solutions or dispersions are prepared with 0.25 v/v Colloidal BIOFILM ® surfactant and sufficient test compound to provide the plants with 0.5, 0.25, 0.125 or 0.06 kg/ha of said compound when the test solutions are sprayed on said plants from an overhead sprayer delivering 747 l/ha of solution.

After spraying the plants are placed on greenhouse benches and watered and fertilized. Three weeks after spraying the plants are examined and the amount of flowering determined for all plants. Data obtained are reported in the table below as percent increase in flowering over untreated controls.

From the data reported in Table VIII below it can be seen that the compounds of the present invention applied at rates of from 0.06 to 0.25 kg/ha enhance flowering of treated plant more than 10% over untreated controls. This response is particularly desirable for treatment of flowering varieties of ornamental plants as well as agronomic crops.

TABLE VIII

Evaluation of test compounds to determine their effectiveness for increasing flowering of the treated plants

| Compound | Rate kg/ha | % Increase in Flowering over untreated controls |
|---|---|---|
| 1,2-Dimethyl-3,5-diphenyl-pyrazolium salt with 2,4,6-tribromo-N—aci-nitroaniline | 0.25 | >10 <15 |
|  | 0.125 | >20 <35 |
|  | 0.06 | >10 <15 |
| 4-Methoxy-1,2-dimethyl-3,5-diphenylpyrazolium salt with 2,4,6-tribromo-N—aci-nitroaniline | 0.5 | Moderate Reduction |
|  | 0.25 | >10 <15 |
|  | 0.125 | >10 <15 |
| 1,2-Dimethyl-3-(3-methylpiperidino)-5-phenyl salt with 2,4,6-tribromo-N—aci-nitroaniline | 0.5 | Slight Reduction |
|  | 0.25 | >10 <15 |
|  | 0.125 | >10 <15 |
| 1,2-Dimethyl-3,5-diphenylpyrazolium salt with 2,4-dibromo-6-iodo-N—aci-nitroaniline | 0.5 | normal |
|  | 0.25 | >10 <15 |
|  | 0.125 | >10 <15 |
| 2,4,6-Tribromo-N—nitroaniline with dibenzylamine | 0.5 | >10 <15 |
|  | 0.25 | >20 <35 |
|  | 0.125 | normal |
| 2,4,6-tribromo-N—nitroaniline with dodecylamine | 0.5 | >20 <35 |
|  | 0.25 | >10 <15 |
|  | 0.125 | normal |

TABLE VIII-continued

Evaluation of test compounds to determine their effectiveness for increasing flowering of the treated plants

| Compound | Rate kg/ha | % Increase in Flowering over untreated controls |
|---|---|---|
| 1,1-Dimethylpiperidinium salt with 2,4,6-tribromo-N—aci-nitroaniline | 0.5 | >20 <35 |
|  | 0.25 | >10 <15 |
|  | 0.125 | normal |
| Methyltriphenylphosphonium salt with 2,4,6-tribromo-N—aci-nitroaniline | 0.5 | >10 <15 |
|  | 0.25 | >10 <15 |
|  | 0.125 | normal |
| 2,4,6-Tribromo-N—nitroaniline, tetrabutylammonium salt | 0.5 | Moderate Reduction |
|  | 0.25 | >20 <35 |
|  | 0.125 | >20 <35 |
| 2,4,6-Tribromo-N—nitroaniline, sodium salt | 0.5 | normal |
|  | 0.25 | >10 <15 |
|  | 0.125 | >10 <15 |
| 2,4,6-Tribromo-N—nitroaniline, potassium salt | 0.5 | normal |
|  | 0.25 | >10 <15 |
|  | 0.125 | >10 <15 |
| (2-Chloroethyl)trimethyl ammonium salt with 2,4,6-tribromo-N—aci-nitroaniline | 0.5 | >10 <15 |
|  | 0.25 | normal |
|  | 0.125 | >10 <15 |
| 2,4,6-Tribromo-N—nitroaniline with ammonia (1:1) | 0.5 | Moderate Reduction |
|  | 0.25 | >10 <15 |
|  | 0.125 | >20 <35 |

EXAMPLE 10

Evaluation of Test Compounds for Enhancing Crop Yield On Cotton

In this experiment cotton plants (*Gossypium hirsutum* var. "Stoneville") are grown in 20×15 cm fibre pots to the 6th to 7th true leaf stage. They are then sprayed with test solutions or dispersions prepared in water-acetone mixtures containing (1) 0.25% v/v of colloidal Biofilm ® surfactant which is a mixture of alkyl aryl polyethoxyethanol, free and combined fatty acids, glycol ethers, dialkylbenzene carboxylate and 2-propanol, and (2) sufficient test compound to provide 1.5, 0.75 or 0.25 kg/ha thereof when applied to said plants from an overhead sprayer designed to deliver 747 l/ha with a moving nozzle over a stationary track. The spray nozzle moves at a constant speed over the test species.

After spraying the plants are placed on greenhouse benches and watered and fertilized in accordance with conventional greenhouse practices. Periodically, the plants are examined, measured, and the number of flower, buds and bolls determined for each plant. Data obtained are reported in table IX below as percent increase in flowers, buds and bolls over untreated controls.

TABLE IX

Evaluation of 1,2-Dimethyl-3,5-diphenylpyrazolium salt with 2,4,6-Tribromo-N—aci-nitroaniline for Cotton Yield Enhancement
(TREATED AT 6 TO 7TH TRUE LEAF STAGE)

| Days After Treatment | Rate (Kg/Ha) | % Height Reduction | % Increase of Visible Flowers and Buds |
|---|---|---|---|
| 33 | 0.25 | — | 29.3 |
|  | 0.75 | 10.1 | 42.8 |
|  | 1.50 | 21.8 | — |
| 42 |  |  |  |
|  | 0.25 | — | 25.9 |
|  | 0.75 | 9.3 | 9.3 |
|  | 1.50 | 7.5 | — |
| 54 |  |  |  |
|  | 0.25 | — | 9.2 |
|  | 0.75 | 9.2 | 33.2 |
|  | 1.50 | 15.0 | 9.6 |

| Days After Treatment | Rate (Kg/Ha) | Flower Buds | % Increase Open Flowers | Bolls |
|---|---|---|---|---|
| 54 | 0.25 | 25.6 | 21.3 | 62.5 |
|  | 0.75 | 25.6 | 32.8 | 41.3 |
|  | 1.50 | — | 29.5 | — |

EXAMPLE 11

Evaluation of Test Compounds for Enhancing Crop Yield In Sunflowers

In this experiment the procedure of Example 7 was repeated excepting that the crop used was sunflowers, *Helianthus annuus* DO164 variety, the plants were sprayed three weeks after planting and at the two leaf stage treatments were made at 0.25, 0.125 and 0.0625 kg/ha of test compound.

The plants were held for 63 days after treatment when the number and weight of flowers was determined and recorded. Data obtained are reported in Table X below.

TABLE X

Evaluation of 1,2-Dimethyl-3,5-diphenylpyrazolium salt with 2,4,6-Tribromo-N—aci-nitroaniline for sunflower yield enhancement
(TREATED AT 2 TRUE LEAF STAGE)

| Days After Treatment | Rate (Kg/Ha) | % Height Reduction | Average Flower Number | % Increase of Flower Weights |
|---|---|---|---|---|
| 63 |  |  |  |  |
|  | 0.0625 | — | 2.1 | 45.5 |
|  | 0.125 | — | 3.8 | 3.7 |
|  | 0.250 | 54.8 | 9.5 | 24.0 |

These data are especially significant since they demonstrate the uniqueness of the pyrazolium salts of the trisubstituted-N-nitroaniline compounds in producing multiple flowering of sunflowers.

EXAMPLE 12

Evaluation of Test Compounds for Enhancing Crop Yield On Soybeans

The procedure of Example 7 was repeated excepting that soybeans (var. Adelphia) were used as the crop plant and plants were treated at the 2nd to 3rd trifoliate stage and held on greenhouse benches for three weeks after treatment. Three weeks after treatment all plants were examined and the number of developed pods counted. Data obtained are reported in Table XI below.

TABLE XI

Evaluation of 1,2-Dimethyl-3,5-diphenylpyrazolium salt with 2,4,6-tribromo-N—aci-nitroaniline for soybean yield enhancement
(TREATED AT 2ND TO 3RD TRIFOLIATE)

| Days After Treatment | Rate (Ka/ha) | % Increase in Pods over untreated controls |
|---|---|---|
| 21 | 0.50 | >10 |
|  | 0.25 | >10 |
|  | 0.125 | >10 |
|  | 0.063 | >10 |

EXAMPLE 13

Evaluation of the Antilodging Effects of Certain N-Nitroanilines and Salts Thereof on Barley In this experiment the procedure of Example 7 is repeated excepting that the crop used was barley (*Hordeum vulgare*, var. Georgie; European lodging prone variety). The plants are treated at the 3-4 leaf stage. Plants are watered prior to treatment and then sprayed to provide the kg/ha rate of test compound desired. After spraying the plants are placed on greenhouse benches and watered and fertilized in accordance with normal greenhouse procedures.

Three weeks after spraying the plants are measured and harvested. All treatments are replicated six times and companions are made against untreated controls. The data obtained are averaged and reported in Table XII below.

The following rating system is used:
5 = No increase over controls
4 = Slight increase over controls
3 = Moderate, significant increase over controls.

TABLE XII

Evaluation of the antilodging effects of substituted N—nitroanilines in barley

| Compound | Rate kg/ha | Phytotoxicity | Height in cm | Tiller formation | Stem stiffness | Weight in g Fresh | Weight in g Dry |
|---|---|---|---|---|---|---|---|
| Control | — | 5 | 53.1 | 5 | 5 | 49.1 | 5.2 |
| 2,6-Dibromo-N—nitroaniline | 1.0 | 5 | 48.3 | 3 | 4 | 55.8 | 5.4 |
|  | 0.5 | 5 | 53.0 | 3 | 4 | 67.5 | 6.9 |
|  | 0.25 | 5 | 50.5 | 4 | 4 | 58.3 | 6.2 |
| 2,6-Dibromo-N—fluoro-N—nitroaniline | 1.0 | 5 | 45.2 | 4 | 5 | 49.2 | — |
|  | 0.5 | 5 | 51.0 | 5 | 5 | 52.6 | — |
|  | 0.25 | 5 | 52.0 | 4 | 4 | 57.8 | 6.0 |
| 1,2-Dibromo-3,5-diphenyl-pyrazolium salt with 2,6-dibromo-N—aci-nitroaniline | 1.0 | 5 | 52.3 | 3 | 3 | 60.4 | 5.9 |
|  | 0.5 | 5 | 53.3 | 5 | 4 | 60.7 | 6.7 |
|  | 0.25 | 5 | 58.2 | 5 | 4 | 59.2 | 6.9 |
| Tallowamine compound with 2,6-dibromo-N—nitroaniline | 1.0 | 5 | 48.7 | 4 | 4 | 55.9 | — |
|  | 0.5 | 5 | 48.5 | 4 | 4 | 60.1 | 7.5 |
|  | 0.25 | 5 | 54.7 | 5 | 4 | 62.3 | 6.8 |
| Sodium salt of 2,6-dibromo-N— | 1.0 | 5 | 47.0 | 3 | 3 | 55.5 | — |

TABLE XII-continued

Evaluation of the antilodging effects of substituted N—nitroanilines in barley

| Compound | Rate kg/ha | Phyto-toxicity | Height in cm | Tiller formation | Stem stiffness | Weight in g Fresh | Dry |
|---|---|---|---|---|---|---|---|
| nitroaniline | 0.5 | 5 | 47.2 | 3 | 4 | 57.6 | 6.4 |
|  | 0.25 | 5 | 50.2 | 4 | 4 | 55.6 | — |
| 2,4-Dibromo-N—nitroaniline | 1.0 | 5 | 53.3 | 5 | 5 | 46.4 | — |
|  | 0.5 | 5 | 56.0 | 5 | 5 | 56.3 | 6.7 |
|  | 0.25 | 5 | 54.7 | 4 | 3 | 63.5 | 7.8 |
| 2-Bromo-4-cyano-N—nitroaniline | 1.0 | 5 | 53.2 | 5 | 5 | 60.9 | 7.0 |
|  | 0.5 | 5 | 53.3 | 4 | 5 | 59.2 | 7.0 |
|  | 0.25 | 5 | 53.0 | 4 | 5 | 62.2 | 7.4 |
| 2-Iodo-4,6-dimethyl-N—nitro-aniline | 1.0 | 5 | 53.5 | 5 | 5 | 58.0 | 6.2 |
|  | 0.5 | 5 | 52.5 | 5 | 5 | 52.7 | — |
|  | 0.25 | 5 | 52.7 | 5 | 5 | 54.1 | — |
| 1,2-Dimethyl-3,5-diphenylpyrazolium salt with 2,3-dichloro-N—aci-nitroaniline | 1.0 | 5 | 55.5 | 5 | 5 | 57.3 | 6.0 |
|  | 0.5 | 5 | 54.7 | 5 | 5 | 52.6 | — |
|  | 0.25 | 5 | 56.3 | 5 | 5 | 51.2 | — |
| Sodium salt with 2,3-dichloro-N—nitroaniline | 1.0 | 5 | 52.2 | 5 | 5 | 57.5 | 6.0 |
|  | 0.5 | 5 | 53.8 | 5 | 5 | 58.7 | 7.1 |
|  | 0.25 | 5 | 53.3 | 5 | 5 | 60.9 | 8.2 |
| Tallowamine compound with 2-ethyl-6-isopropyl-N—nitro-aniline | 1.0 | 5 | 45.7 | 4 | 4 | 52.4 | — |
|  | 0.5 | 5 | 41.7 | 4 | 4 | 47.1 | — |
|  | 0.25 | 5 | 45.0 | 4 | 4 | 49.2 | — |
| 1,2-Dimethyl-3,5-diphenyl-pyrazolium salt with 2-Bromo-N—aci-nitroaniline | 1.0 | 5 | 50.0 | 5 | 5 | 47.4 | — |
|  | 0.5 | 5 | 50.6 | 5 | 5 | 53.5 | — |
|  | 0.25 | 5 | 52.5 | 4 | 4 | 51.0 | — |
| 2-Ethyl-6-isopropyl-N—nitro-aniline | 1.0 | 5 | 51.0 | 4 | 4 | 56.5 | 5.4 |
|  | 0.5 | 5 | 48.7 | 3 | 4 | 59.3 | 5.9 |
|  | 0.25 | 5 | 47.7 | 4 | 4 | 50.5 | — |

We claim:

1. A salt of a substituted N-nitroaniline represented by the structural formula

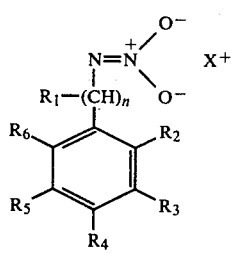

wherein n is an integer of 0 or 1; $R_1$ is hydrogen or methyl; $R_2$ and $R_6$ are halogen, $C_1$-$C_2$ alkyl, $CF_3$; $SO_2R_8$ or $SR_8$ wherein $R_8$ is $C_1$-$C_6$ alkyl, phenyl, or benzyl and with the proviso that only one of $R_2$ and $R_6$ may be F, $CF_3$, $SCH_3$, $C_2H_5$ or $SO_2C_6H_5$; $R_3$ is hydrogen; $R_4$ is hydrogen, Br, F, I, $CH_3$, $COC_6H_5$, CN or $SO_2N(CH_3)_2$; $R_5$ is hydrogen; $X^+$ is organic and represented by structural formula IIIe

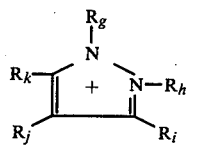

wherein $R_g$ and $R_h$ is each methyl or ethyl; $R_i$ and $R_k$ are phenyl or cyclohexyl; and $R_j$ is hydrogen or $OCH_3$.

2. The compound according to claim 1, 1,2-dimethyl-3,5-diphenylpyrazolium salt with 2,4,6-tribromo-N-aci-nitroaniline.

3. The compound according to claim 1, 1,2-dimethyl-3,5-diphenylpyrazolium salt with 2,6-dibromo-N-aci-nitroaniline.

4. A compound according to claim 1, wherein $R_2$ is F, Cl, Br, I, or $CF_3$; $R_6$ is Cl, Br or I; $R_4$ is Br, I or hydrogen; and $R_1$, $X^+$, $R_g$, $R_h$, $R_i$, $R_j$ and $R_k$ are as described in claim 1.

5. A compound according to claim 1, 1,2-dimethyl-3,5-diphenylpyrazolium salt with 2-bromo-6-iodo-N-aci-nitro aniline.

6. A compound according to claim 1, 1,2-dimethyl-3,5-diphenylpyrazolium salt with 2-bromo-4,6-diiodo-N-aci-nitroaniline.

7. A compound according to claim 1, 1,2-dimethyl-3,5-diphenylpyrazolium salt with 2-chloro-4,6-diiodo-N-aci-nitroaniline.

8. A compound according to claim 1, 1,2-dimethyl-3,5-diphenylpyrazolium salt with 2,6-dichloro-α-methyl-N-aci-nitrobenzylamino.

9. A compound according to claim 1, 1,2-dimethyl-3,5-diphenylpyrazolium salt with 2,4,6-triiodo-N-aci-nitroaniline.

10. A compound according to claim 1, 1-ethyl-2-methyl-3,5-diphenylpyrazolium salt with 2,4,6-tribromo-N-aci-nitroaniline.

11. A compound according to claim 1, 1,2-dimethyl-3,5-diphenylpyrazolium salt with 2,4-dibromo-α-α-α-trifluoro-N-aci-o-toluidine.

12. A compound according to claim 1, 1,2-dimethyl-3,5-diphenylpyrazolium salt with 2,4-dibromo-6-iodo-N-aci-nitroaniline.

* * * * *